US011413032B2

(12) United States Patent
Running et al.

(10) Patent No.: US 11,413,032 B2
(45) Date of Patent: Aug. 16, 2022

(54) SURGICAL ANCHORING DEVICE, DEPLOYMENT DEVICE, AND METHOD OF USE

(71) Applicant: Embody, Inc., Norfolk, VA (US)

(72) Inventors: Isaac Running, Bozeman, MT (US); Robert J. Ball, West Olive, MI (US); Douglas Snell, South Portland, ME (US); R. Sean Churchill, Mequon, WI (US)

(73) Assignee: Embody, Inc., Norfolk, VA (US)

( * ) Notice: Subject to any disclaimer, the term of this patent is extended or adjusted under 35 U.S.C. 154(b) by 0 days.

(21) Appl. No.: 17/174,057

(22) Filed: Feb. 11, 2021

(65) Prior Publication Data

US 2021/0275161 A1 Sep. 9, 2021

Related U.S. Application Data

(60) Provisional application No. 62/972,718, filed on Feb. 11, 2020, provisional application No. 62/972,722, filed on Feb. 11, 2020.

(51) Int. Cl.
*A61B 17/04* (2006.01)

(52) U.S. Cl.
CPC .. *A61B 17/0401* (2013.01); *A61B 2017/0412* (2013.01); *A61B 2017/0427* (2013.01); *A61B 2017/0464* (2013.01)

(58) Field of Classification Search
CPC . A61B 17/064; A61B 17/0642; A61B 17/068; A61B 17/0682; A61B 17/0401;

(Continued)

(56) References Cited

U.S. PATENT DOCUMENTS

| 4,570,623 A | 2/1986 | Ellison et al. |
| 4,635,637 A | 1/1987 | Schreiber |

(Continued)

FOREIGN PATENT DOCUMENTS

| EP | 0991359 | 12/2010 |
| EP | 1761176 | 9/2016 |

(Continued)

OTHER PUBLICATIONS

International Search Report and Written Opinion dated Jul. 14, 2021 in PCT/US2021/176680.

(Continued)

*Primary Examiner* — Dianne Dornbusch
(74) *Attorney, Agent, or Firm* — Plumsea Law Group, LLC

(57) ABSTRACT

A surgical anchoring device may include a first beam and a second beam each extending along a longitudinal direction; and a connecting member bridging a first proximal portion of the first beam to a second proximal portion of the second beam such that the first beam is substantially aligned with the second beam. In addition, the anchoring device may include a first barb protruding from a medial side of the first beam, wherein the first barb extends diagonally in a generally proximal direction; and a second barb protruding from a medial side of the second beam, wherein the second barb extends diagonally in a generally proximal direction. The first barb may include a proximal facing surface that is separated from the first beam by a recess.

20 Claims, 40 Drawing Sheets

(58) Field of Classification Search
CPC .... A61B 2017/0646; A61B 2017/0647; A61B 2017/0419; A61B 2017/0412; A61B 2017/0427; A61B 2017/0429; A61B 2017/0437; A61B 2017/0464; A61B 17/08; A61B 17/083; A61B 2017/0641; A61B 2017/0645; A61B 2017/081; A61B 2017/0409

See application file for complete search history.

(56) References Cited

U.S. PATENT DOCUMENTS

| | | |
|---|---|---|
| 5,089,009 A | 2/1992 | Green |
| 5,195,542 A | 3/1993 | Gazielly et al. |
| 5,269,783 A | 12/1993 | Sander |
| 5,318,589 A | 6/1994 | Lichtman |
| 5,342,376 A | 8/1994 | Ruff |
| 5,374,268 A | 12/1994 | Sander |
| 5,441,508 A | 8/1995 | Gazielly et al. |
| 5,584,849 A | 12/1996 | Yoon |
| 5,643,319 A | 7/1997 | Green et al. |
| 5,662,655 A | 9/1997 | Laboureau et al. |
| 5,947,999 A | 9/1999 | Groiso |
| 5,997,552 A | 12/1999 | Person et al. |
| 6,059,787 A | 5/2000 | Allen |
| 6,179,872 B1 | 1/2001 | Bell et al. |
| 6,190,401 B1 | 2/2001 | Green et al. |
| 6,270,517 B1 | 8/2001 | Brotz |
| 6,348,054 B1 | 2/2002 | Allen |
| 6,387,113 B1 | 5/2002 | Hawkins et al. |
| 6,554,852 B1 | 4/2003 | Oberlander |
| 6,599,310 B2 | 7/2003 | Leung et al. |
| 6,666,872 B2 | 12/2003 | Barreiro et al. |
| 6,726,705 B2 | 4/2004 | Peterson et al. |
| 6,755,863 B2 | 6/2004 | Ferree |
| 6,783,531 B2 | 8/2004 | Allen |
| 6,852,330 B2 | 2/2005 | Bowman et al. |
| 7,112,214 B2 | 9/2006 | Peterson et al. |
| 7,153,312 B1 | 12/2006 | Torrie et al. |
| 7,175,648 B2 | 2/2007 | Nakao |
| 7,547,326 B2 | 6/2009 | Bhatnagar et al. |
| 7,559,941 B2 | 7/2009 | Zannis et al. |
| 7,601,165 B2 | 10/2009 | Stone |
| 7,632,313 B2 | 12/2009 | Bhatnagar et al. |
| 7,658,751 B2 | 2/2010 | Stone et al. |
| 7,686,200 B2 | 3/2010 | Peterson |
| 7,749,250 B2 | 7/2010 | Stone et al. |
| 7,803,395 B2 | 9/2010 | Datta et al. |
| D625,417 S | 10/2010 | Fox et al. |
| 7,819,918 B2 | 10/2010 | Malaviya et al. |
| 7,887,551 B2 | 2/2011 | Bojarski et al. |
| 7,909,851 B2 | 3/2011 | Stone et al. |
| 7,963,972 B2 | 6/2011 | Foerster et al. |
| 7,967,841 B2 | 6/2011 | Yuan et al. |
| 8,066,736 B2 | 11/2011 | Peterson et al. |
| 8,070,818 B2 | 12/2011 | Bhatnagar et al. |
| 8,080,260 B2 | 12/2011 | Derwin et al. |
| 8,084,428 B2 | 12/2011 | Spector et al. |
| 8,088,130 B2 | 1/2012 | Kaiser et al. |
| 8,092,529 B2 | 1/2012 | Malaviya et al. |
| 8,118,836 B2 | 2/2012 | Denham et al. |
| 8,128,658 B2 | 3/2012 | Kaiser et al. |
| 8,273,105 B2 | 9/2012 | Cohen et al. |
| 8,361,113 B2 | 1/2013 | Stone et al. |
| 8,454,653 B2 | 6/2013 | Hadba et al. |
| 8,585,773 B1 | 11/2013 | Kucklick |
| 8,668,718 B2 | 3/2014 | Euteneuer et al. |
| 8,702,718 B2 | 4/2014 | Bhatnagar et al. |
| D705,930 S | 5/2014 | Cheney |
| 8,734,485 B2 | 5/2014 | Leung et al. |
| 8,734,486 B2 | 5/2014 | Leung et al. |
| D706,927 S | 6/2014 | Cheney et al. |
| D707,357 S | 6/2014 | Cheney et al. |
| 8,739,389 B2 | 6/2014 | Cohen et al. |
| 8,753,359 B2 | 6/2014 | Levin et al. |
| 8,763,878 B2 | 7/2014 | Euteneuer et al. |
| 8,821,507 B2 | 9/2014 | Axelson, Jr. et al. |
| 8,821,536 B2 | 9/2014 | Euteneuer et al. |
| 8,821,537 B2 | 9/2014 | Euteneuer et al. |
| 8,840,642 B2 | 9/2014 | Euteneuer et al. |
| 8,864,780 B2 | 10/2014 | Euteneuer et al. |
| 8,888,810 B2 | 11/2014 | Hadba et al. |
| 8,888,811 B2 | 11/2014 | Levin et al. |
| 8,906,045 B2 | 12/2014 | Levin et al. |
| 8,920,464 B2 | 12/2014 | Euteneuer et al. |
| 8,936,619 B2 | 1/2015 | Odermatt et al. |
| 9,005,224 B2 | 4/2015 | Euteneuer et al. |
| 9,017,331 B2 | 4/2015 | Fox |
| 9,027,819 B2 | 5/2015 | Euteneuer et al. |
| 9,033,201 B2 | 5/2015 | Euteneuer |
| 9,089,379 B2 | 7/2015 | Sack et al. |
| 9,095,337 B2 | 8/2015 | Euteneuer et al. |
| 9,101,460 B2 | 8/2015 | Euteneuer et al. |
| 9,107,726 B2 | 8/2015 | Levin et al. |
| 9,113,977 B2 | 8/2015 | Euteneuer et al. |
| 9,179,910 B2 | 11/2015 | Euteneuer et al. |
| 9,179,961 B2 | 11/2015 | Euteneuer et al. |
| D744,646 S * | 12/2015 | Nering .......... D24/145 |
| 9,198,704 B2 | 12/2015 | Sack et al. |
| 9,198,750 B2 | 12/2015 | Van Kampen et al. |
| 9,198,751 B2 | 12/2015 | Euteneuer et al. |
| 9,204,940 B2 | 12/2015 | Euteneuer et al. |
| 9,259,220 B2 | 2/2016 | Euteneuer et al. |
| 9,314,331 B2 | 4/2016 | Euteneuer et al. |
| 9,339,268 B2 | 5/2016 | Fox |
| 9,393,002 B2 | 7/2016 | Iceman et al. |
| 9,393,103 B2 | 7/2016 | Van Kampen et al. |
| 9,393,104 B2 | 7/2016 | Van Kampen et al. |
| 9,433,456 B2 | 9/2016 | Yeh et al. |
| 9,463,009 B2 | 10/2016 | Sack et al. |
| D780,311 S | 2/2017 | Cheney et al. |
| 9,572,615 B2 | 2/2017 | Sack et al. |
| 9,642,891 B2 | 5/2017 | Hart et al. |
| 9,655,709 B2 | 5/2017 | Kelly et al. |
| 9,675,346 B2 | 6/2017 | Euteneuer et al. |
| 9,675,395 B2 | 6/2017 | Averous et al. |
| 9,687,227 B2 | 6/2017 | Marczyk et al. |
| 9,713,467 B2 | 7/2017 | Cohen et al. |
| 9,743,926 B2 | 8/2017 | Fox |
| 9,743,970 B2 | 8/2017 | Euteneuer et al. |
| 9,788,832 B2 | 10/2017 | Hadba et al. |
| D804,666 S * | 12/2017 | Guo .......... D24/145 |
| 9,855,036 B2 | 1/2018 | Palmer et al. |
| 9,872,679 B2 | 1/2018 | Perkins et al. |
| 9,878,141 B2 | 1/2018 | Kucklick |
| 9,931,119 B2 | 4/2018 | Euteneuer et al. |
| 9,987,027 B2 * | 6/2018 | Ben-Ami .......... A61B 17/22031 |
| 9,993,247 B2 | 6/2018 | Euteneuer |
| 10,010,320 B2 | 7/2018 | Wahl |
| 10,016,198 B2 | 7/2018 | Morgan et al. |
| 10,052,103 B2 | 8/2018 | Wahl |
| 10,064,618 B2 | 9/2018 | Allen |
| 10,064,619 B2 | 9/2018 | Palmer et al. |
| 10,085,785 B2 | 10/2018 | Euteneuer et al. |
| 10,105,134 B2 | 10/2018 | Biedermann et al. |
| 10,105,210 B2 | 10/2018 | Van Kampen et al. |
| 10,123,796 B2 | 11/2018 | Westling et al. |
| 10,123,866 B2 | 11/2018 | Van Kampen et al. |
| 10,166,021 B2 | 1/2019 | Wilke et al. |
| 10,172,703 B2 | 1/2019 | Adams et al. |
| 10,195,016 B2 | 2/2019 | Euteneuer et al. |
| 10,226,325 B2 | 3/2019 | Euteneuer et al. |
| 10,245,138 B2 | 4/2019 | Euteneuer et al. |
| 10,258,459 B2 | 4/2019 | Zenz-Olson |
| 10,265,156 B2 | 4/2019 | Van Kampen |
| 10,278,801 B2 | 5/2019 | Kucklick |
| 10,292,743 B2 | 5/2019 | Taylor et al. |
| 10,307,238 B2 | 6/2019 | Kucklick |
| 10,314,689 B2 | 6/2019 | Zenz-Olson et al. |
| 10,336,001 B2 | 7/2019 | Perkins et al. |
| 10,376,352 B2 | 8/2019 | Kelly et al. |
| 10,413,397 B2 | 9/2019 | Euteneuer et al. |
| 10,426,464 B2 | 10/2019 | Euteneuer et al. |
| 10,449,031 B2 | 10/2019 | Euteneuer et al. |

(56) References Cited

U.S. PATENT DOCUMENTS

| | | |
|---|---|---|
| 10,512,459 B2 | 12/2019 | Fox |
| 10,568,622 B2 | 2/2020 | Euteneuer et al. |
| 10,568,627 B2 | 2/2020 | Guo et al. |
| 10,610,218 B2 | 4/2020 | Palmer et al. |
| 10,610,221 B2 | 4/2020 | Wahl |
| 10,610,222 B2 | 4/2020 | Wahl |
| 10,653,415 B2 | 5/2020 | Euteneuer et al. |
| 10,660,686 B2 | 5/2020 | Sack et al. |
| 10,675,016 B2 | 6/2020 | Coleman |
| 10,695,155 B2 | 6/2020 | Levin et al. |
| D895,113 S | 9/2020 | Blair et al. |
| 10,765,423 B2 | 9/2020 | Coleman |
| 10,806,565 B2 | 10/2020 | Euteneuer et al. |
| 10,813,742 B2 | 10/2020 | Adams et al. |
| 10,820,981 B2 | 11/2020 | Ravenscroft et al. |
| 10,835,235 B2 | 11/2020 | Coleman |
| 10,835,368 B2 | 11/2020 | Zenz-Olson et al. |
| 10,864,072 B2 | 12/2020 | Van Kampen et al. |
| 10,874,503 B2 | 12/2020 | Zenz-Olson et al. |
| 2002/0127265 A1 | 9/2002 | Bowman et al. |
| 2004/0138705 A1* | 7/2004 | Heino ............ A61B 17/064 606/219 |
| 2005/0113938 A1 | 5/2005 | Jamiolkowski et al. |
| 2006/0029633 A1 | 2/2006 | Kaiser et al. |
| 2006/0247641 A1 | 11/2006 | Re et al. |
| 2007/0156174 A1 | 7/2007 | Kaiser et al. |
| 2007/0162030 A1 | 7/2007 | Aranyi et al. |
| 2007/0190108 A1 | 8/2007 | Datta et al. |
| 2007/0288023 A1 | 12/2007 | Pellegrino et al. |
| 2008/0051809 A1 | 2/2008 | Verheist et al. |
| 2009/0156986 A1 | 6/2009 | Trenhaile |
| 2009/0156997 A1 | 6/2009 | Trenhaile |
| 2009/0182375 A1 | 7/2009 | Isse et al. |
| 2009/0312791 A1 | 12/2009 | Lindh, Sr. et al. |
| 2010/0146770 A1 | 6/2010 | Morency et al. |
| 2010/0191332 A1 | 7/2010 | Euteneuer et al. |
| 2010/0211098 A1* | 8/2010 | Hadba ............ A61B 17/064 606/232 |
| 2010/0256675 A1 | 10/2010 | Romans |
| 2010/0292715 A1* | 11/2010 | Nering ............ A61B 17/0682 606/151 |
| 2010/0312250 A1* | 12/2010 | Euteneuer ........ A61F 2/30749 606/99 |
| 2012/0071566 A1 | 3/2012 | Kelly et al. |
| 2012/0109188 A1* | 5/2012 | Viola ............ A61B 17/064 606/213 |
| 2012/0211543 A1* | 8/2012 | Euteneuer ........ A61F 2/0063 227/175.1 |
| 2012/0265219 A1 | 10/2012 | Rushdy et al. |
| 2013/0153627 A1* | 6/2013 | Euteneuer ........ A61B 17/08 227/175.1 |
| 2013/0153628 A1* | 6/2013 | Euteneuer ........ A61B 17/17 227/175.1 |
| 2013/0158554 A1* | 6/2013 | Euteneuer ........ A61B 17/08 606/75 |
| 2013/0184716 A1 | 7/2013 | Euteneuer et al. |
| 2014/0276968 A1* | 9/2014 | Miksza ............ A61B 17/064 606/139 |
| 2015/0157310 A1* | 6/2015 | Coillard-Lavirotte ........ A61B 17/0401 606/232 |
| 2015/0313592 A1 | 11/2015 | Coillard-Lavirotte et al. |
| 2015/0327975 A1 | 11/2015 | Euteneuer et al. |
| 2017/0065276 A1 | 3/2017 | Weiner et al. |
| 2017/0202920 A1 | 7/2017 | Hart et al. |
| 2017/0252036 A1 | 9/2017 | Palmer et al. |
| 2018/0153551 A1* | 6/2018 | Guo ............ A61B 17/10 |
| 2018/0256162 A1 | 9/2018 | Euteneuer |
| 2018/0271521 A1 | 9/2018 | Wahl |
| 2018/0360914 A1 | 12/2018 | Hart et al. |
| 2019/0015145 A1 | 1/2019 | Euteneuer et al. |
| 2019/0029802 A1 | 1/2019 | Van Kampen et al. |
| 2019/0038395 A1 | 2/2019 | Van Kampen |
| 2019/0059883 A1* | 2/2019 | Westling ............ A61B 17/10 |
| 2019/0069892 A1 | 3/2019 | Biedermann et al. |
| 2019/0110885 A1 | 4/2019 | Zenz-Olson et al. |
| 2019/0175328 A1 | 7/2019 | Zenz-Olson et al. |
| 2019/0209287 A1 | 7/2019 | Zenz-Olson |
| 2019/0231404 A1 | 8/2019 | Taylor et al. |
| 2019/0254802 A1 | 8/2019 | Kucklick |
| 2019/0274675 A1 | 9/2019 | Coleman |
| 2019/0274814 A1 | 9/2019 | Euteneuer et al. |
| 2019/0282352 A1 | 9/2019 | Kucklick |
| 2019/0350608 A1 | 11/2019 | Kucklick |
| 2019/0388215 A1 | 12/2019 | Euteneuer et al. |
| 2020/0000462 A1 | 1/2020 | Euteneuer et al. |
| 2020/0170780 A1 | 6/2020 | Euteneuer et al. |
| 2020/0197003 A1 | 6/2020 | Euteneuer et al. |
| 2020/0197005 A1* | 6/2020 | Daniel ............ A61B 17/8811 |
| 2020/0214700 A1 | 7/2020 | Biedermann et al. |
| 2020/0214701 A1 | 7/2020 | Wahl |
| 2020/0237366 A1 | 7/2020 | Wahl |
| 2020/0237499 A1 | 7/2020 | Zenz-Olson et al. |

FOREIGN PATENT DOCUMENTS

| | | |
|---|---|---|
| FR | 2800595 | 1/2002 |
| WO | 2009086172 | 7/2009 |
| WO | 2014043610 | 3/2014 |

OTHER PUBLICATIONS

Rotator Cuff Failure, UW Orthopaedics and Sports Medicine, Seattle, Jan. 25, 2005. (Available at; https://orthop.washington.edu/patient-care/articles/shoulder/rotator-cuff-failure.html).
Ethicon Stratafix product catalog 2018.
Covidien V-loc product catalog 2021.
Quill product catalog 2007-2014.

* cited by examiner

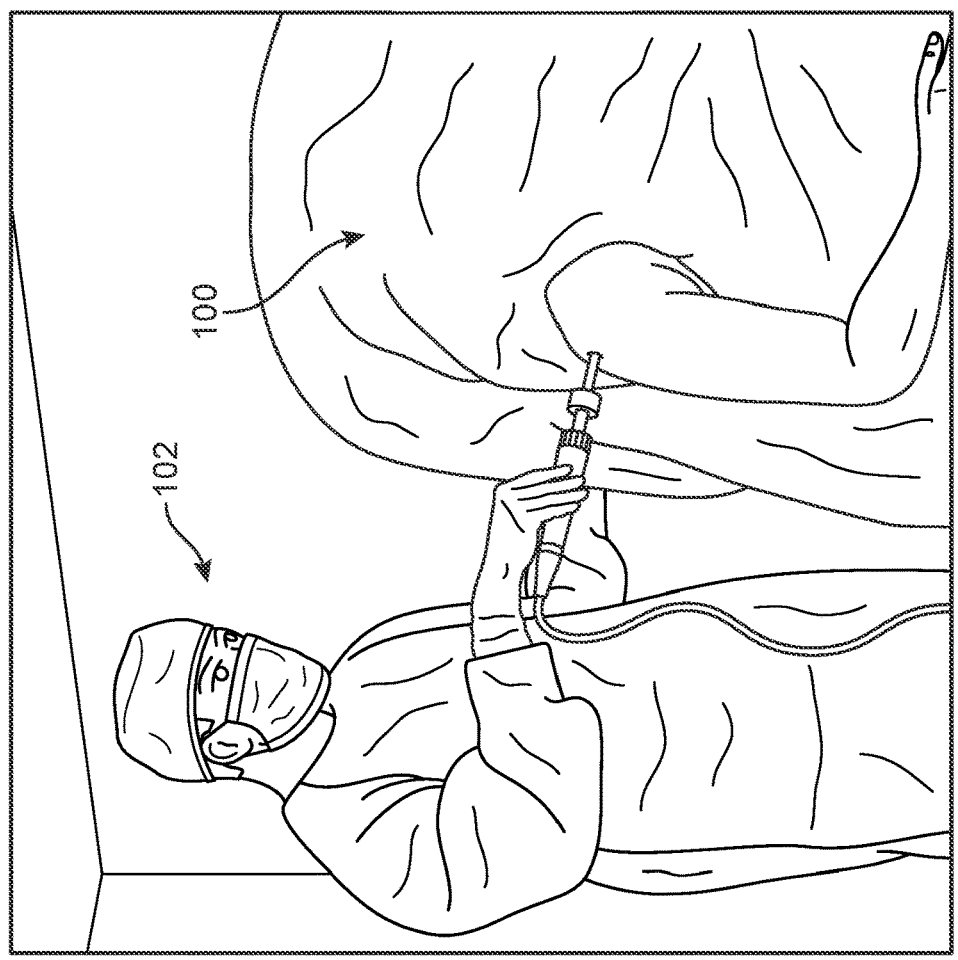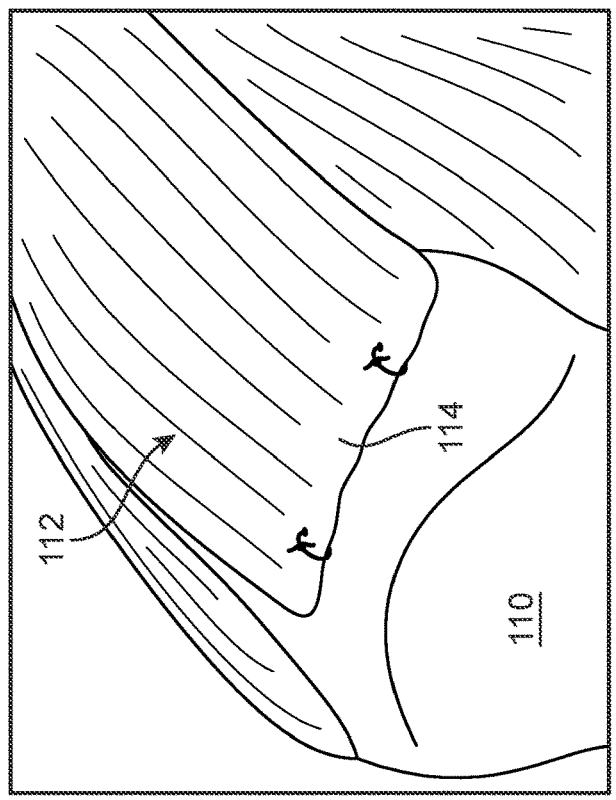
FIG. 1

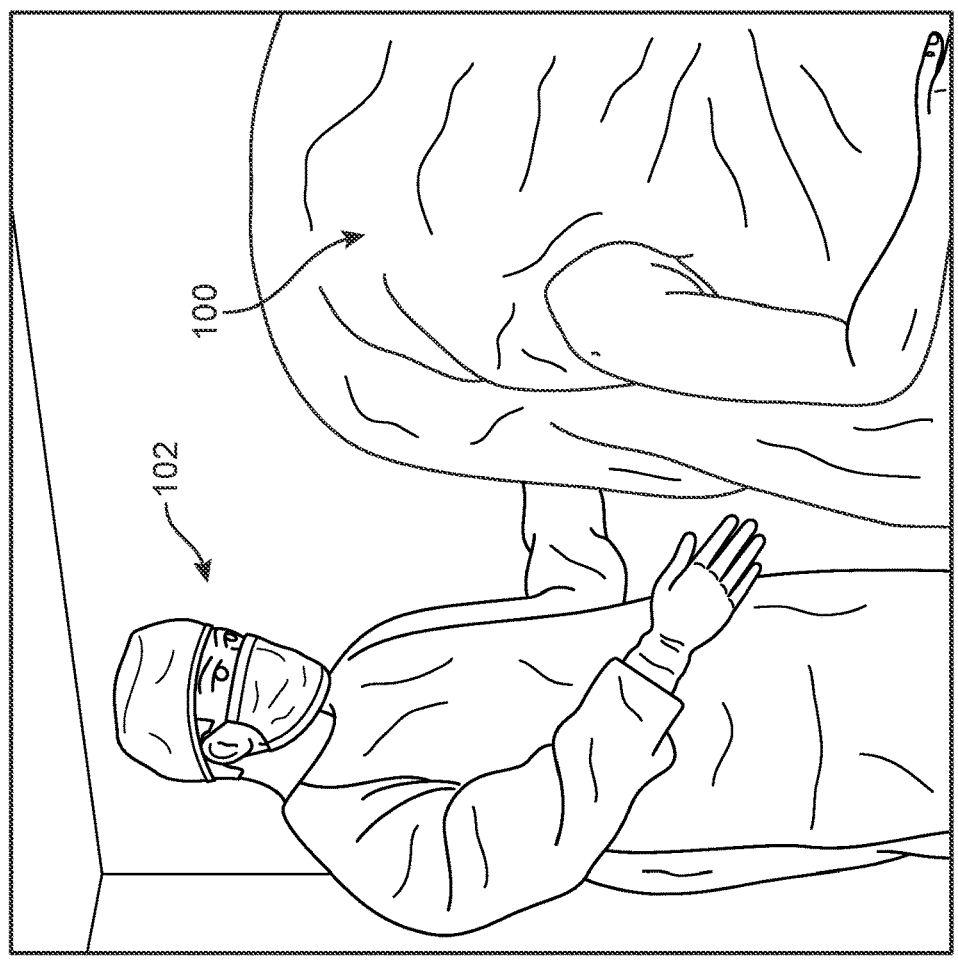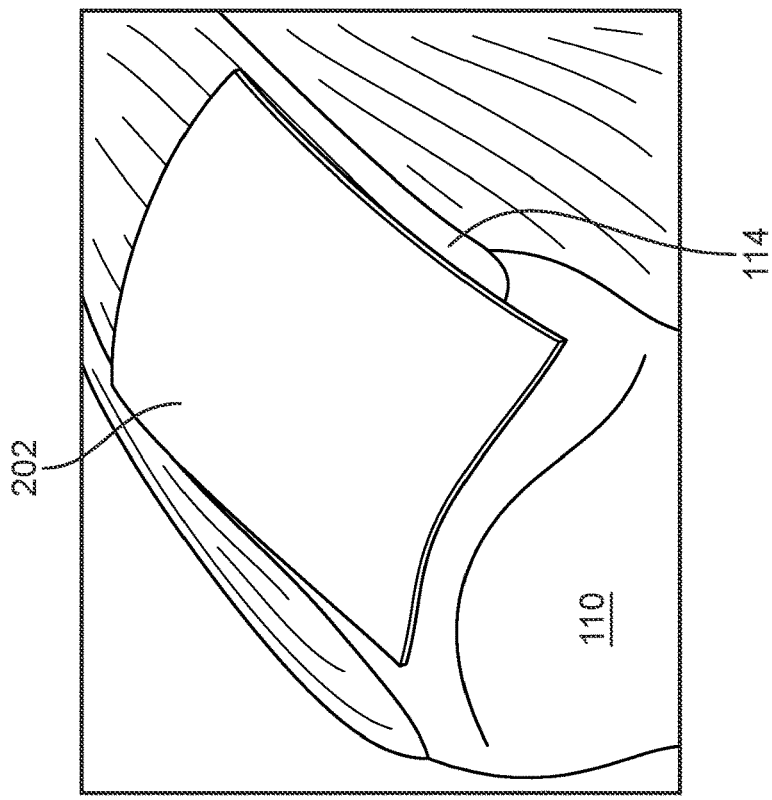
FIG. 2

SURGICAL ANCHORING DEVICE, DEPLOYMENT DEVICE, AND METHOD OF USE

CROSS-SECTION TO RELATED APPLICATIONS

This application claims the benefit of U.S. Provisional Patent Application No. 62/972,718, filed on Feb. 11, 2020, and titled "Anchoring Device for Tissue and Method of Insertion," the entire disclosure of which is hereby incorporated by reference, and U.S. Provisional Patent Application No. 62/972,722, filed on Feb. 11, 2020, and titled "Deployment Device for Inserting Anchors into Tissue," the entire disclosure of which is hereby incorporated by reference.

BACKGROUND

The present embodiments relate generally to medical devices, and in particular to medical devices used to repair tissue.

Rotator cuff repair is a surgical procedure performed to repair torn (or partially torn) tendons in the shoulder. This procedure can be done with large incisions or with arthroscopic techniques. To repair a torn tendon (such as the supraspinatus tendon), a surgeon may use anchors and sutures to reattach the tendon to the humerus bone. The repaired area may then be covered with a graft to facilitate healing.

Currently, grafts may be applied using anchors to fix the graft to the underlying tendon and/or bone. The anchors may cause inflammation. Additionally, the anchors are implanted by inserting a device through one or more openings at the top of the shoulder, which can make it difficult to access all of the desired joint spaces.

There is a need in the art for a system and method that addresses the shortcomings discussed above.

SUMMARY

In one aspect, the present disclosure is directed to a surgical anchoring device. The anchoring device may include a first beam and a second beam each extending along a longitudinal direction and a connecting member bridging a first proximal portion of the first beam to a second proximal portion of the second beam such that the first beam is substantially aligned with the second beam. In addition, the anchoring device may include a first barb protruding from a medial side of the first beam, wherein the first barb extends diagonally in a generally proximal direction. The first barb may include a proximal facing surface that is separated from the first beam by a recess.

In another aspect, the present disclosure is directed to a surgical anchoring device. The anchoring device may include a first beam and a second beam bridged by a connecting member. The anchoring device may further include a first set of barbs protruding from the first beam, the first set of barbs including a first barb and a second barb; and a second set of barbs protruding from the second beam, the second set of barbs including a third barb and a fourth barb. At least one of the barbs may include a tip portion corresponding to an intersection of a proximal surface, a first side surface, a second side surface, and a distal ridge surface.

In another aspect, the present disclosure is directed to method of implanting a surgical anchoring device. The method may include providing a deployment device loaded with a first anchoring device comprising a frame structure including a first beam and a second beam bridged together by a connecting member and having a retention portion proximate a distal end of the first anchoring device configured to resist withdrawal of the anchoring device from tissue. The deployment device may further include at least one pair of needle members, including a first needle member and a second needle member configured to receive the first beam and the second beam of the first anchoring device, at least one anchor engaging rod configured to engage with the first anchoring device when disposed within the needle members; and at least one pushing member configured engage the pair of needle members and the anchor engaging rod. The method may include actuating the at least one pushing member, thereby translating the pair of needles and the first anchoring device from a first position within the deployment device to a second position extending from the distal end of the deployment device. The method may also include retracting the needle members independent of the anchor engaging rod such that the anchor engaging rod maintains the anchoring device in the second position, thereby releasing the anchoring device from the needle members.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

FIG. 1 is a schematic view of a step in a procedure for repairing a rotator cuff tendon, according to an embodiment;

FIG. 2 is a schematic view of a step of applying a graft to a portion of a rotator cuff tendon to facilitate healing, according to an embodiment;

DETAILED DESCRIPTION

Figure 3:
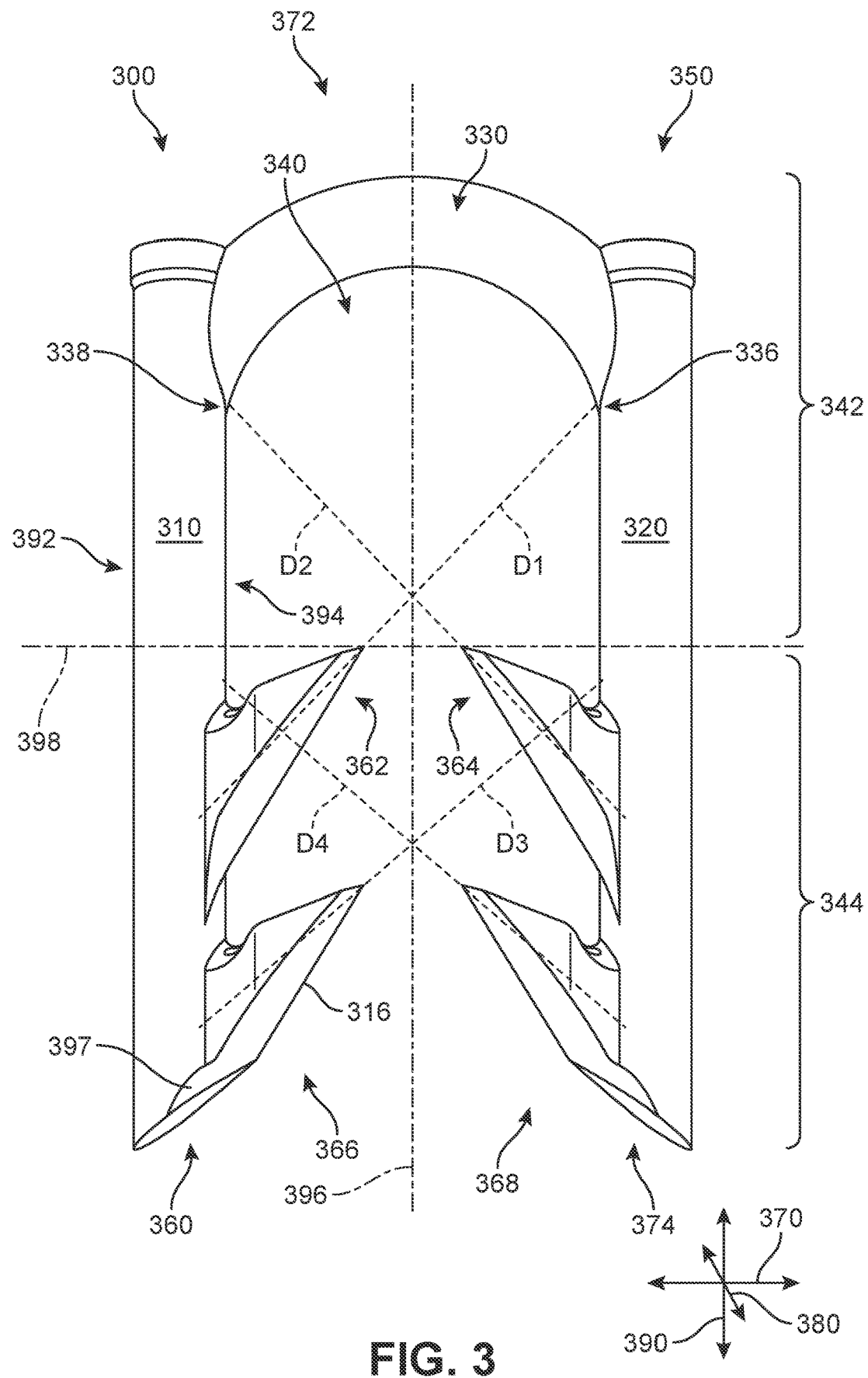
FIG. 3 is a schematic view of an embodiment of an anchoring device.

The embodiments provide an anchoring system that can be used to secure a graft in place over underlying tissue (such as tendons and/or bones) within the body. For example, the anchoring system can be used to secure the graft over a rotator cuff tendon and/or part of the humerus bone. The anchoring system includes an anchoring device and a deployment device (or instrument) that is used to insert portions of the anchoring device through a graft and underlying tissue.

The anchoring device of the embodiments comprises an arch-shaped body or frame structure that includes a plurality of barbs. The frame structure includes a first beam and a second beam. The proximal end portions of the two beams are bridged by a connecting member. Barbs protrude from an interior-facing or medial side of each beam. Each barb is oriented diagonally inward and proximally upward in a direction toward a central longitudinal axis. As the anchoring device is inserted into tissue, the orientation of the barbs ensures that the anchoring device resists any forces that would act to pull out the anchoring device from the tissue.

The deployment device of the embodiments comprises a body that can be gripped in one hand by a user and an elongated deployment tube assembly that extends from the body to a tip. The deployment tube assembly includes a pair of tubes in which the anchoring device may be movably secured or retained. An internal pushing member can be deployed using a trigger on the body. When the anchoring device is loaded in the deployment device and the deployment device is triggered, the pushing member can move an anchor engaging rod and needle members to extend both from the distal tip of the deployment device, thus driving the needle members through the graft and underlying tissue with the anchoring device disposed within the needle members. Then, the needle members are retracted, leaving the anchoring device behind in the graft/tissue.

Because the anchoring device is loaded along the exterior of the deployment device, the diameter of the deployment tube assembly can be kept sufficiently small and may be inserted through or directed toward very small arthroscopic incisions. The design of the deployment device facilitates a lateral approach to the shoulder. This enables access to the joint space under the acromion, which can be more difficult to access when approached head-on from the top aspect of the shoulder.

FIG. 1 is a schematic view illustrating a surgical procedure to repair a tendon in a patient's shoulder. Specifically, a patient 100 is undergoing arthroscopic surgery that is performed by surgeon 102. Also shown in FIG. 1 is an enlarged view of a portion of humerus 110 and rotator cuff tendons 112. In the present example, surgeon 102 has recently applied anchors and sutures to secure supraspinatus tendon 114 to humerus 110.

Once the tendon has been sufficiently repaired, surgeon 102 may insert a graft through an incision (possibly using another device to facilitate insertion). The graft can then be placed over the repaired tendon and/or portion of the underlying bone in order to facilitate healing. As an example, FIG. 2 shows a schematic view of a graft 202 that has been applied over the recently repaired tendon 114 as well as over a portion of humerus 110.

Although the exemplary embodiment depicts a procedure in which a tendon is first secured to the bone using sutures and anchors, in other embodiments a graft can be applied to one or more tendons without first reattaching a tendon. For example, grafts could be applied to tendons that have only partial tears. Further, it will be understood that the disclosed anchoring device may be utilized to secure materials other than grafts. For example, the anchoring device may be used to secure soft tissue to other soft tissue or to secure soft tissue to bone. Also, in some embodiments, the anchors may be used to secure sheet-like implants (other than grafts), as well as provide anchor points for sutures.

Once graft 202 has been placed over the repaired tendon, one or more sutures or anchors are required to hold graft 202 in place. The present embodiments disclose both a filament with anchoring elements that can be used to hold a graft in place, as well as an instrument for deploying the filament with anchoring elements.

FIG. 3 is a schematic view of an anchoring device 300 that may be used to secure a graft in place along a tendon, bone, and/or at the interface of a tendon and bone. Anchoring device 300 may comprise a frame structure 350 that includes a first beam 310 and a second beam 320 bridged by a connecting member 330. In addition, the anchoring device 300 includes a plurality of barbs ("barbs") 360 extending or protruding outward from the first beam 310 and the second beam 320. Specifically, the first beam 310 includes a first barb 362 and a second barb 366, and the second beam 320 includes a third barb 364 and a fourth barb 368. Portions or areas of the first beam 310 and/or second beam 320 that include barbs will be referred to as barbed regions, and portions or areas of the first beam 310 and/or second beam 320 without barbs will be referred to as unbarbed regions.

In some embodiments, exterior surfaces in the unbarbed regions are generally smooth. Moreover, unlike the barbs, whose cross-sectional size varies along their length due to the tapering shape of each barb, the unbarbed beam portions may have an approximately constant cross-sectional size corresponding to the diameter of the beam and/or connecting member. In FIG. 3, the first beam 310 and second beam 320 are substantially cylindrical in shape, such that the body of each beam will have a circular cross-section. However, in other embodiments, the beam structure may encompass any elongated geometry, including rods and bars of different curvatures and shapes. Similarly, the connecting member 330 may also have a substantially circular cross-sectional shape, but in other embodiments may have another shape. In different embodiments, the components/elements may include any three-dimensional shape. For example, in FIG. 3, while the beams are substantially linear or straight, the connecting member 330 is curved in an arc-shape. In addition, it may be appreciated that in different embodiments, barbs could have any suitable geometry. Exemplary geometries include, but are not limited to: T-bar geometries, arrowhead geometries, wedge geometries, pyramidal geometries, etc. It may be appreciated that embodiments could employ any suitable barb-like elements or elements that resist pull-out from a material along a particular direction.

In some cases, anchoring device 300 could comprise a monolithic structure, with both the frame structure and barbs constructed of a single unitary piece of material. For example, anchoring device 300 could be a 3D printed structure formed from a single biocompatible material. In other cases, the frame structure and barbs could comprise distinct structures mechanically joined. In one example, an anchoring device could be made by coating a beam comprised of a first biocompatible material with a second biocompatible material. At some locations along the beam, the second biocompatible material coating could be shaped into barbs. In another example, each set of barbs could be formed as a sleeve of material that can be placed over a beam and fixed in place, for example, using an adhesive. In this case, the beam and the sleeve could be made of different materials. Furthermore, depending on the desired applications, the anchoring device 300 could be hollow or solid, and/or portions of the anchoring device 300 may be filled or hollow. For example, in cases where a different distribution of weight would benefit the patient, the anchoring device 300 could be printed with some portions being hollow and lighter, and other portions being filled and heavier. When bioabsorbable materials are utilized, it may be advantageous to vary the overall thickness of different portions of the anchoring device as a way to control the amount of time it takes each portion to dissolve in the body.

The number of barbs associated with an anchoring device, as well as their distribution along the beams, could vary. In some cases, the barbs could be arranged in approximately regular patterns. For example, in the embodiment shown in FIG. 3, the anchoring device 300 comprises four barbs, symmetrically located on the opposing beams. In other embodiments, the anchoring device could comprise any suitable different numbers of barbs, spaced at any suitable intervals. The number of barbs could be selected according to the intended depth of penetration of an anchor as well as the desired resistance to any pull-out forces that would act to tug the anchor out of the tissue after it has been installed. In different embodiments, the length of the unbarbed portions may be selected so that they are long enough to allow movement of the anchoring device, but not too long to make implantation difficult. Further, the length of the unbarbed portions may be long enough to pass through the thickness of a graft so that the barbs engage the tissue beneath the graft. Accordingly, it may be appreciated that an anchoring device may be manufactured with any suitable length and include any number of barbs.

For clarity, the description makes reference to distal and proximal directions (or portions). As used herein, the distal direction is a direction oriented away from a user who is holding a device. Also, the proximal direction is a direction oriented toward a user who is holding a device. Thus, a distal side or region refers to a portion of the device that is disposed further from the user holding the device and a proximal side or region refers to a portion of a device that is disposed nearer to the user holding the device during normal use.

In addition, the terms medial and lateral refer to sides of a device or component/element thereof, where a medial side of a component generally faces toward a center of the device, and a lateral side of a component generally faces away from the center of the device.

Furthermore, the term "longitudinal axis" as used throughout this detailed description and in the claims refers to an axis that extends in a longitudinal direction, which is a direction extending the length of each device, including the anchoring device and the deployment device. In the present case, a longitudinal axis extends in the proximal-distal direction.

The term "lateral axis" as used throughout this detailed description and in the claims refers to an axis that extends in a lateral direction, which is a direction running a width of each device, including the anchoring device and the deployment device. In addition, the term "transverse axis" as used throughout this detailed description and in the claims refers to an axis that extends in a transverse direction, which is a direction running along a thickness of each device, including the anchoring device and the deployment device. Each axis of the three axes may be understood to be orthogonal relative to the other two axes.

In FIG. 3, for purposes of reference, a longitudinal axis 390, lateral axis 370, and transverse axis 380 are indicated. In addition, the anchoring device 300 is shown to include a distal end 374 and a proximal end 372. A medial side 394 is also labeled for purposes of example on the side of the first beam 310 closer to a central longitudinal axis 396 (shown in dotted line) that generally divides the anchoring device 300 in two equal parts. The side that faces outward or away from the center is labeled as a lateral side 398. In addition, a proximal end 372 of the anchoring device 300 is the end that is above or toward the top of the drawing (e.g., the end including the connecting member 330), while a distal end 374 of the anchoring device 300 is the end that is below or toward the bottom in the drawing (e.g., the end including the barbs 360). For purposes of convenience, terms such as below, bottom, lower, etc. may also be used to describe the distal end or distal portions of the anchoring device, while terms such as above, top, higher, etc. may also be used to describe proximal end or proximal portions of the anchoring device.

For purposes of reference, a central lateral axis 398 (shown in dotted line) is included that generally demarcates the lateral midline of the anchoring device 300 into a proximal region 342 and a distal region 344. In addition, while anchoring device 300 is substantially symmetrical or mirror-images with respect to the central longitudinal axis 396, anchoring device 300 is asymmetrical with respect to the central lateral axis 398.

In some embodiments, anchoring device 300 can have a shape that resembles an archway. For example, as shown in FIG. 3, the connecting member 330 can represent the top of the arch, and the first beam 310 and second beam 320 can correspond to the pillars supporting the arch. Furthermore, in some embodiments, the lengths of the beams 310 and 320 can be greater than the length of the connecting member 330 (extending from a first end 338 to a second end 336). In some cases, a beam can have a length that is 1.5-2 times greater than the length of the connecting member 330. In one embodiment, a straight-line distance between first end 338 and second end 336 can correspond to half the length of a beam.

In the embodiment of FIG. 3, the distal side of the connecting member and the medial sides of the two beams are joined to form a substantially smooth, continuous curvature. In some other examples, the anchoring device 300 may be understood to have a substantially U-shaped structure (in FIG. 3, the "U" shape is upside-down). Thus, in one embodiment, the outer components or elements (i.e., the first beam 310, second beam 320, and connecting member 330) can provide a boundary or perimeter that surrounds an interior area 340. In FIG. 3, the interior area 340 has a substantially parabolic shape or outline. It is within this interior area 340 that the barbs 360 are disposed.

In different embodiments, the barbs 360 may be arranged in various positions along a medial surface of one or both of the beams. In the embodiment presented herein, a first spacing between the first barb 362 and second barb 366 is substantially similar to a second spacing between the third barb 364 and fourth barb 368. However, in other embodiments, the spacing between different barbed areas can alternate between a relatively longer spacing and a relatively shorter spacing (e.g., such that the anchoring device 300 is no longer symmetrical with respect to the central longitudinal axis 396). More specifically, in FIG. 3, the space between the barbs on each beam is selected to ensure that the barbs 360 are disposed in the distal region 344 of the anchoring device 300, while the proximal region 342 remains unbarbed, optimizing the resistance to pull-out forces that might tug on the anchoring device 300 after it has been implanted in tissue. For example, the barbs 360 will be inserted first (being located in the distal portion of the device) when the anchoring device 300 is pushed into tissue, while the proximal portion remains unbarbed to facilitate the ability of the deployment device to grip and move the anchoring device 300, and then to extend through a graft and ultimately provide stability to the anchoring device 300 once it has been installed. In other cases, however, the arrangement of barbs could occur in any other suitable pattern that supports the intended depth of penetration as well as the desired resistance to any pull-out forces.

In some embodiments, the orientation of the barbs 360 serve to ensure that the anchoring device 300 resists any forces that would act to pull out the anchoring device from the tissue. The orientation depicted in FIG. 3 has been shown to provide an increased resistance to pull-out. In FIG. 3, each barb of the anchoring device 300 is oriented diagonally upward in a generally proximal direction. Specifically, the first barb 362 is oriented along a first direction D1, the second barb 366 is oriented along a second direction D2, the third barb 364 is oriented along a third direction D3, and the fourth barb 368 is oriented along a fourth direction D4, where each direction D1-D4 corresponds to the average or general direction of the protruding barb (e.g., the proximal and distal surfaces of each barb extend in directions that are either less steep or steeper than the central direction labeled as D1-D4). In the embodiment of FIG. 3, the first direction D1 corresponds to the first barb 362 extending in a direction toward the intersection between the connecting member 330 and second beam 320 (around second end 336 of connecting member 330), while the third direction D3 is roughly opposite, corresponding to the third barb 364 extending in a direction toward the intersection between the connecting member 330 and first beam 320 (around first end 338 of connecting member 330). Furthermore, the second direction D2 corresponds to the second barb 366 extending in a direction toward the distal surface (lower side) of the third barb 364, and then toward the portion of second beam 320 near the central lateral axis 398, while the fourth direction D4 corresponds to the fourth barb 368 extending in a direction toward the distal surface (lower side) of the first barb 362, and then toward the portion of first beam 310 near the central lateral axis 398. Thus, the orientation of the barbs 360 forms a double crisscross shape.

In different embodiments, an anchoring device could be configured to have a variety of sizes for the frame structure and barbs. In some cases, the frame structure could have a diameter in-between 0.5 mm and 2 mm. In other cases, the frame structure could have a diameter of less than 0.5 mm. In still other cases, the frame structure could have a diameter of greater than 2 mm. Also, each barb could have a maximum radial length of between 1 mm and 5 mm. In other cases, each barb could have a maximum radial length that is greater than 5 mm.

An anchoring device may be made of a variety of materials. In some cases, an anchoring device could be made of one or more biocompatible materials. A biocompatible material may be any natural or synthetic material that can be used to replace tissue or to function while being in contact with other tissue in a manner that does not damage the adjacent tissue. Examples of biocompatible materials include, but are not limited to: metals, ceramics, and polymers. More specific examples include nylon, prolene, dacron, polydioxanone (PDS), polypropylene and ultra high molecular weight polyethylene (UHMWPE). In some cases, the biocompatible material could be a bioabsorbable polymer that is gradually absorbed by adjacent tissue. Examples of bioabsorbable materials include poly L-lactic acid (PLLA), polyglycolic acid (PGA), polytetrafluorethylene (PTFE), polyaryletherketone (PAEK), polyetheretherketone (PEEK), and poly-(D, Lactic acid) (PDLLA).

Figure 4A:
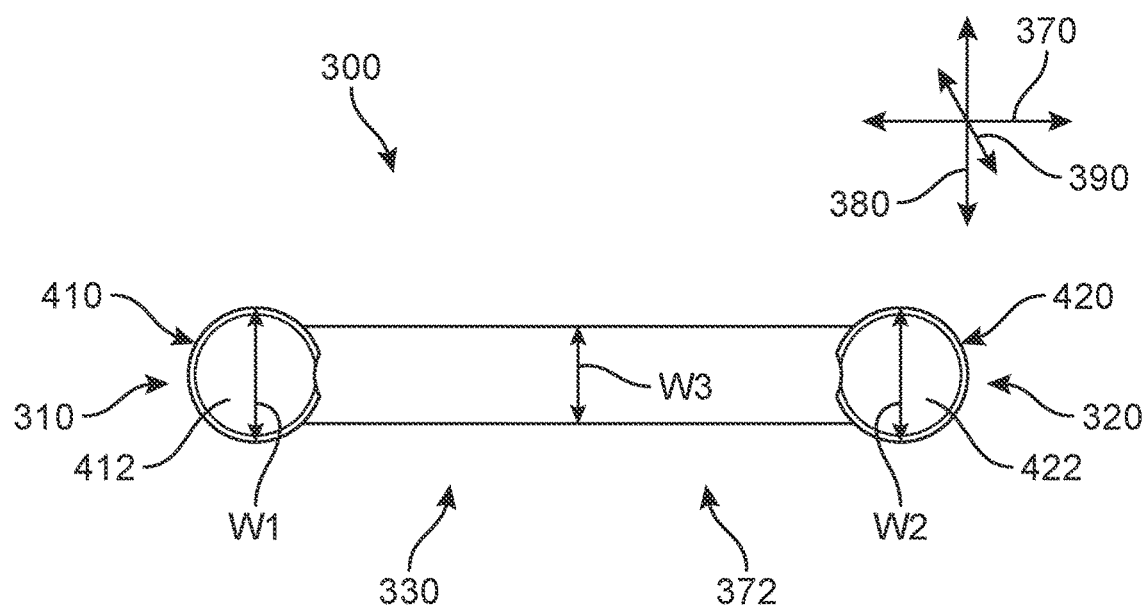
FIG. 4A is a schematic top-down view of an embodiment of an anchoring device.
Figure 4B:
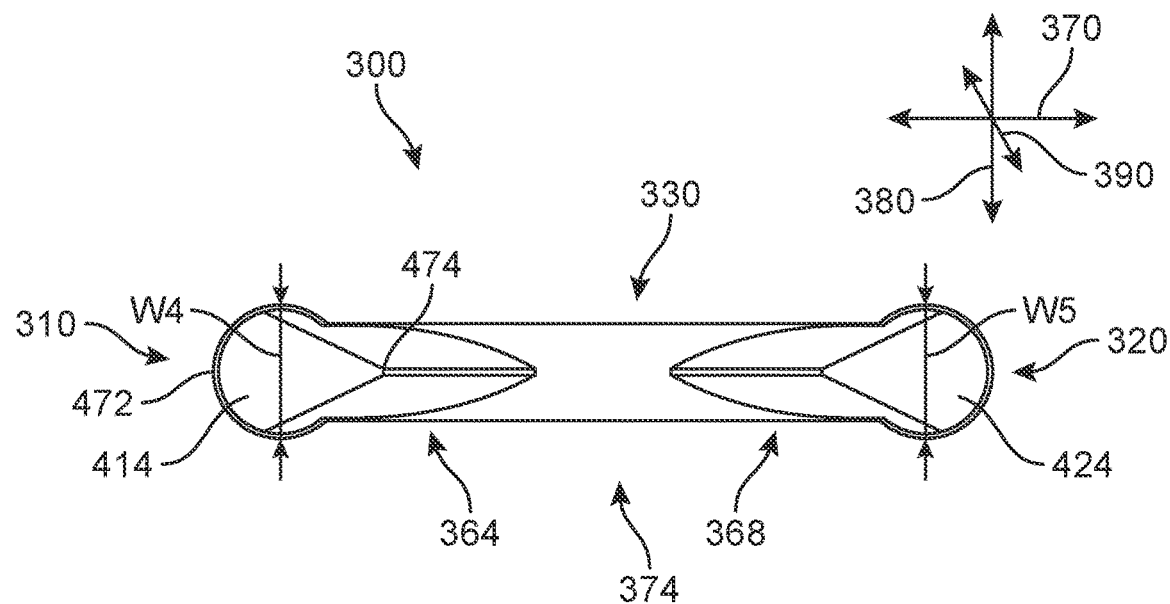
FIG. 4B is a schematic bottom-side view of an embodiment of an anchoring device.
Figure 4C:
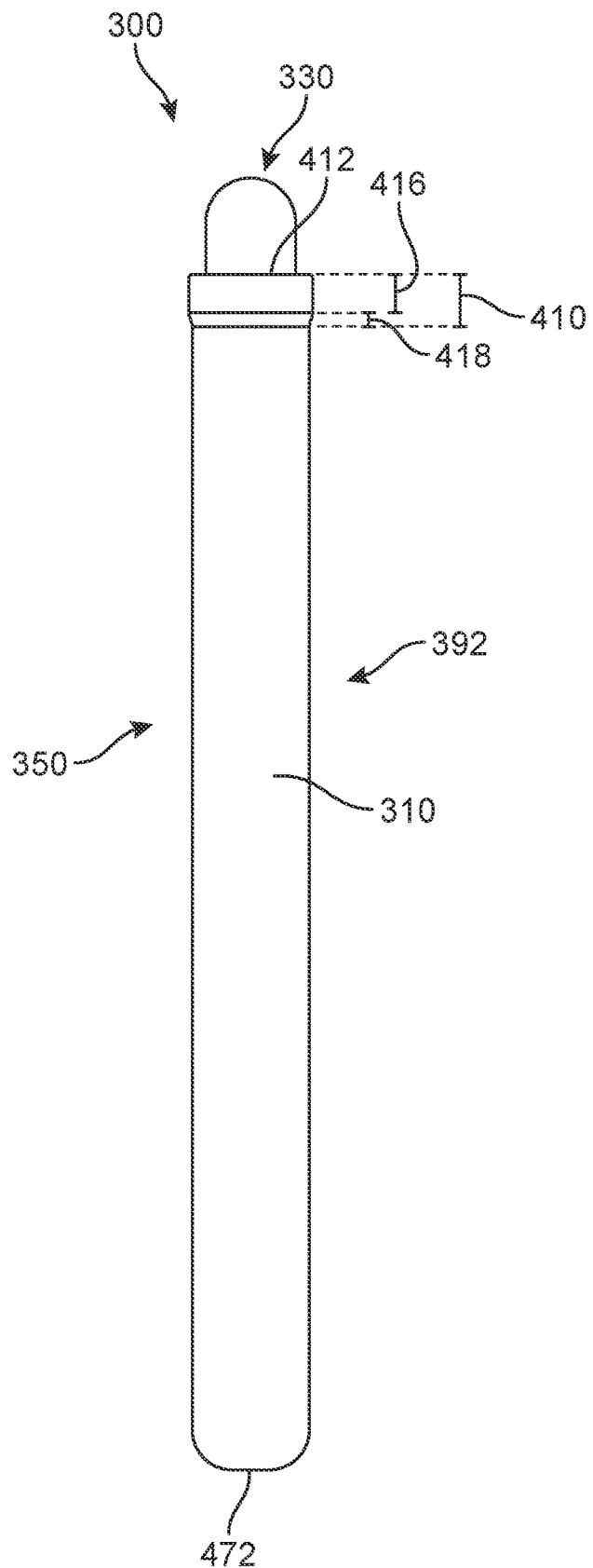
FIG. 4C is a schematic side view of an embodiment of an anchoring device.

For purposes of clarity, additional views of the anchoring device 300 are now provided in FIGS. 4A-4C. FIG. 4A depicts the anchoring device 300 in a top-down view, in which the viewer looks directly at proximal end 372. In some embodiments, first beam 310 and second beam 320, while substantially smooth and have a constant cross-sectional size along a substantial majority of their exterior surface, can also include additional elements. For example, first beam 310 includes a first enlarged crown element ("first crown") 410, and second beam 320 includes a second enlarged crown element ("second crown") 420. In addition, a first width W1 (in this case also corresponding to a diameter of first crown 410) is also substantially equal to a second width W2 (corresponding to a diameter of second crown 420), while a third width W3 of the connecting member 330 is smaller than either first width W1 or second width W2, where each width is measured along the transverse axis 380.

The crown elements of the anchoring device may have the same diameter as the inner diameter of the needle members (1512A, 1512B, 1522A, and 1522B) discussed below with respect to FIGS. 16, 34, and 35, among other figures. This maintains stability of the anchoring device while the needle members are being retracted with respect to the anchor device. It will be understood that, although the crown elements are shown at the proximal ends of the beams, these enlarged needle engaging elements may be disposed at any location along the length of the beams.

In some embodiments, the shape of the distal tips of the anchoring device may have substantially the same shape as the distal tips of the needle members. For example, in order to correspond with a Greene tip needle, the bevels at the distal tips of the anchoring devices may include a scalloped portion 397 along the side of the beams, as shown in FIG. 3. This scalloped portion corresponds to a curved aspect of a Greene tip needle grind. The geometry at the distal tips of the anchoring devices helps prevent the anchors from going into compression during insertion through tissue/graft material. This feature is discussed in greater detail with respect to FIGS. 34 and 35 below.

In some embodiments, the beams may terminate in surfaces that have different shapes at the proximal end than at the distal end of the beams. For example, in some embodiments, the beams may have a proximal end that terminates in a substantially circular surface, and a distal end that terminates in a substantially teardrop-shaped surface. For example, both the first crown 410 and second crown 420 each have a proximal-side facing surface that is substantially circular (corresponding to the base ends of the cylindrical beams) and labeled here as a first disc 412 and a second disc 422. The exterior surfaces of first disc 412 and second disc 422 are substantially flat and planar and smooth. As will be discussed in later figures, the shape and dimensions of the discs are selected to align with and rest flush against the pushing portions of the deployment device. In addition, in some embodiments, the surface of first disc 412 and second disc 422 is oriented in a substantially orthogonal direction relative to the orientation of the cylindrical portion of the beams.

FIG. 4B depicts the anchoring device 300 in an upside-down view, in which the viewer looks directly at distal end 374. In this view, a distal or first bottom surface 414 of second barb 364 and a second bottom surface 424 of fourth barb 368 can be more clearly seen, as well as the distal surface of connecting member 330. In some embodiments, a fourth width W4 is also substantially equal to the first width W1 (see FIG. 4A), and a fifth width W5 is substantially equal to the second width W2 (see FIG. 4A), which allows for the smooth translation of the anchoring device 300 along the deployment tubes of deployment device, as will be discussed below. FIG. 4B also depicts the tapered geometry of the bottom surfaces of the barbs having a teardrop-shape. Furthermore, as will be more clearly shown in later figures, the first bottom surface 414 and second bottom surface 424 are substantially flat or planar, and are oriented in a diagonally upward direction such that a tapered tip 474 is further proximal and medial relative to a rounded outer edge portion 472 of each surface. That is, first bottom surface 414 and second bottom surface 424 are oriented at an oblique angle relative to the lateral axis 370 (see also FIG. 3).

FIG. 4C presents a lateral side view of anchoring device 300. In FIG. 4C, the structure of crown elements can be seen more clearly. In FIG. 4C, first crown 410 is shown, comprising a cylindrical portion with a slightly greater diameter than that of the beam body below. In addition, in some embodiments, the first crown 410 includes an upper crown portion 416 and a lower crown portion 418 that is narrower than the upper crown portion 416. The lower crown portion 418 can smooth the transition between the beam body and the upper crown portion 416. For example, in some embodiments, lower crown portion 418 may be a beveled surface, as shown in FIG. 4C. Thus, overall, the crown elements may be enlarged with respect to the beams. In addition, the lateral side view illustrates the additional length of anchoring device 300 provided by the curvature of connecting member 330. It can be seen that a top-most portion of connecting member 330 (corresponding to its center) extends further proximally relative to the proximal end of first beam 310.

Figure 5:
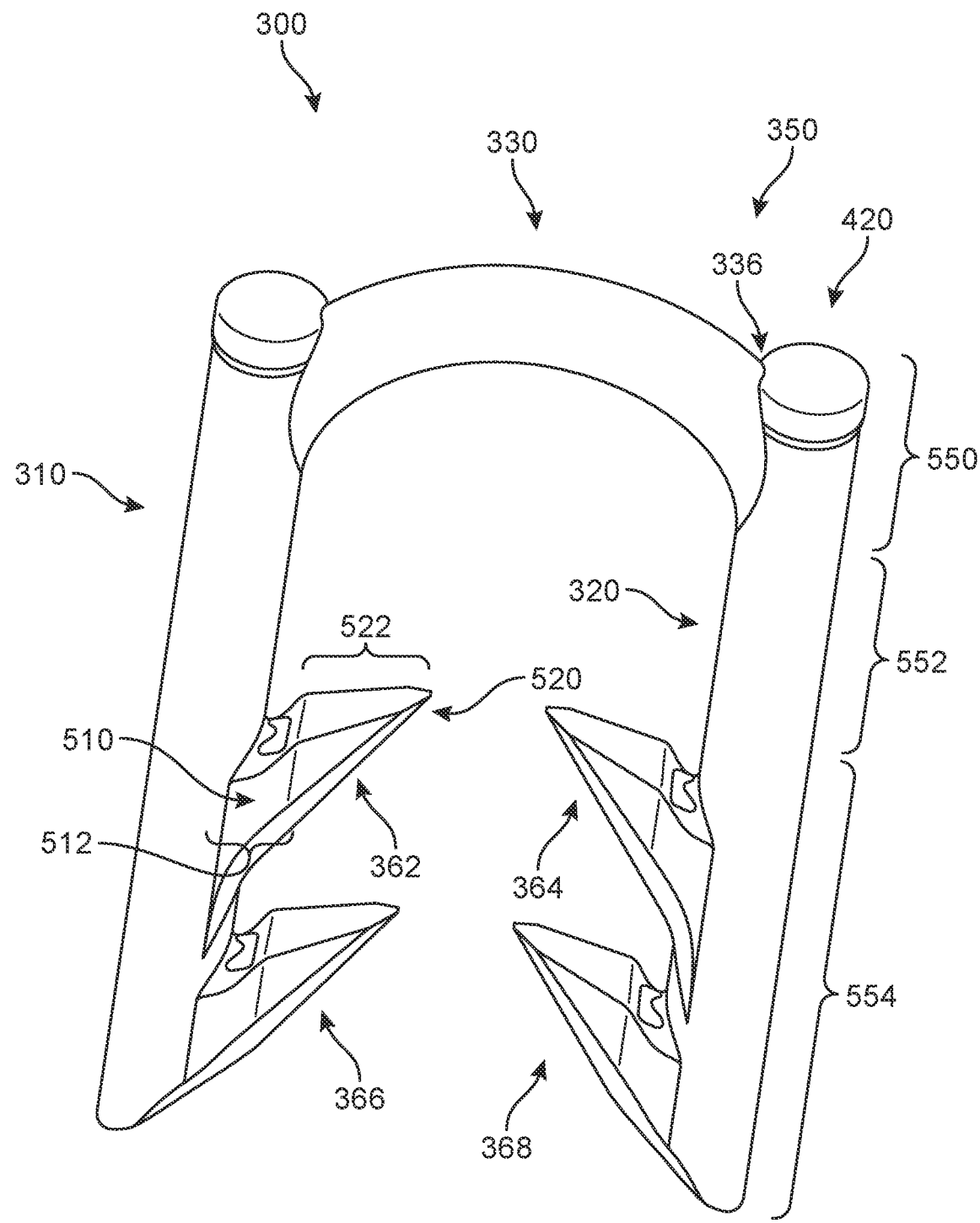
FIG. 5 is a schematic perspective side view of an anchoring device, according to an embodiment.

For purposes of reference, each beam can be understood to comprise three regions. As an example, in FIG. 5, the second beam 320 is shown as including a proximal region 550, an intermediate region 552, and a distal region 554. Descriptions of second beam 320 should be understood to apply to the first beam 310 (and vice-versa). The intermediate region 552 extends between the proximal region 550 and distal region 554 and comprises an unbarbed and substantially smooth portion of the beam. In contrast, the proximal region 552 is joined on its medial side to the second end 336 of the connecting member 330, and includes second crown 420, while distal region 554 is barbed with third barb 364 and fourth barb 368.

In addition, each barb can be understood to include a base portion 510 and a tapered portion 520, where the two portions are joined to form a continuous element. The base portion 510 protrudes outward from the medial side of the first beam 310 and provides structural support and reinforcement to the tapered portion 520 of the barb. In addition, the base portion 510 has a smaller first lateral length 512 than a second lateral length 522 of the tapered portion 520.

Figure 6:
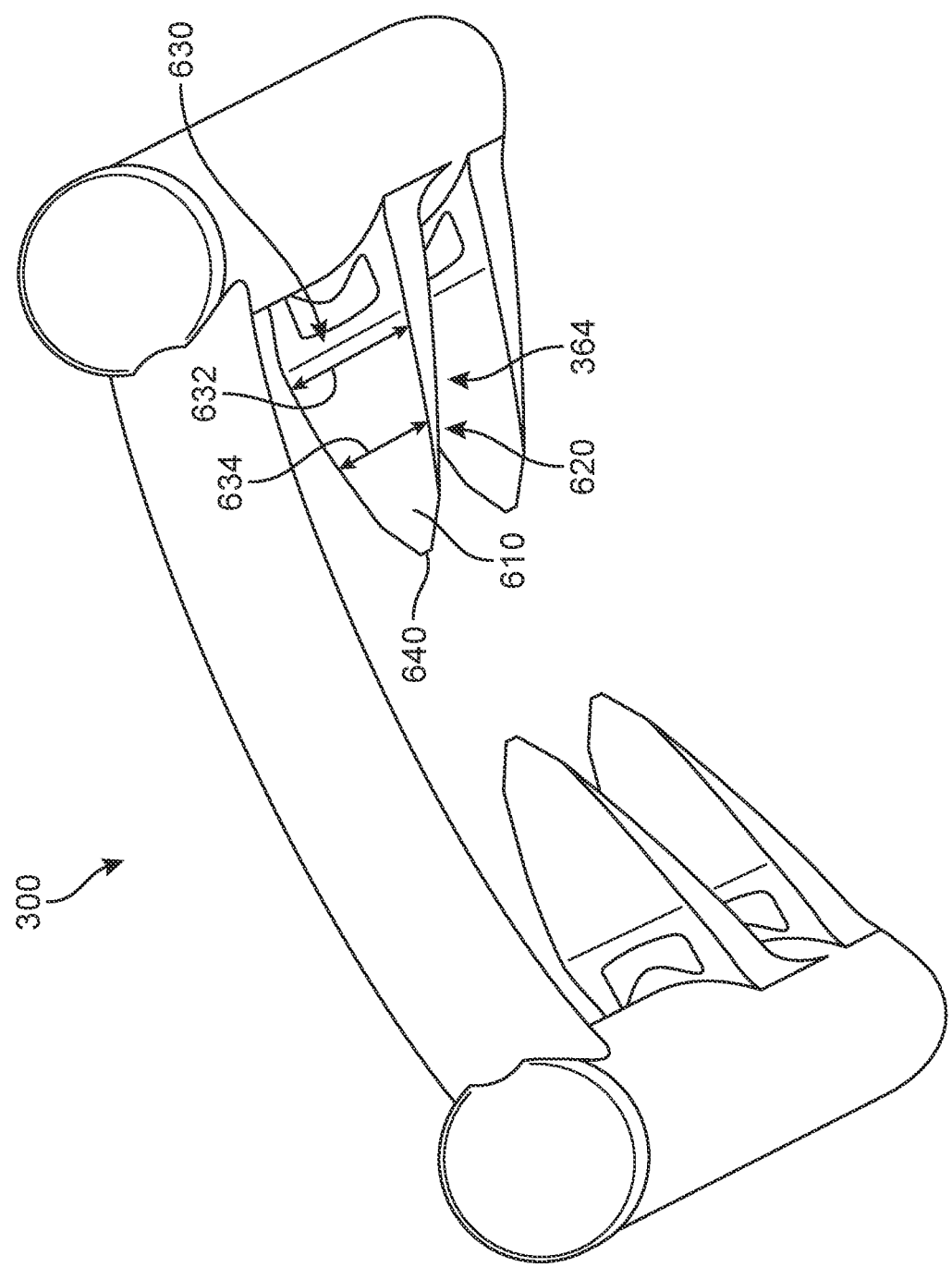
FIG. 6 is a schematic perspective top view of an anchoring device, according to an embodiment.

Additional details regarding the barbs are now provided with reference to FIGS. 6-9. FIG. 6 depicts a perspective top view of the anchoring device 300, in which a top surface 610 of the third barb 364 is discussed as an example. Details for the top surface 610 may be understood to be applicable to other barbs. In this view, the shape of top surface 610 can be more clearly seen, comprising a substantially arrowhead-like shape, extending from a first side 630 with a first width 632, decreasing to a second width 634 in a central region 620, and tapering or diminishing to a narrow point or rounded tip portion 640 with a width of close to zero. Furthermore, top surface 610 is substantially smooth and flat, and extends in a diagonally upward direction as it approaches the tip 640.

Figure 7:
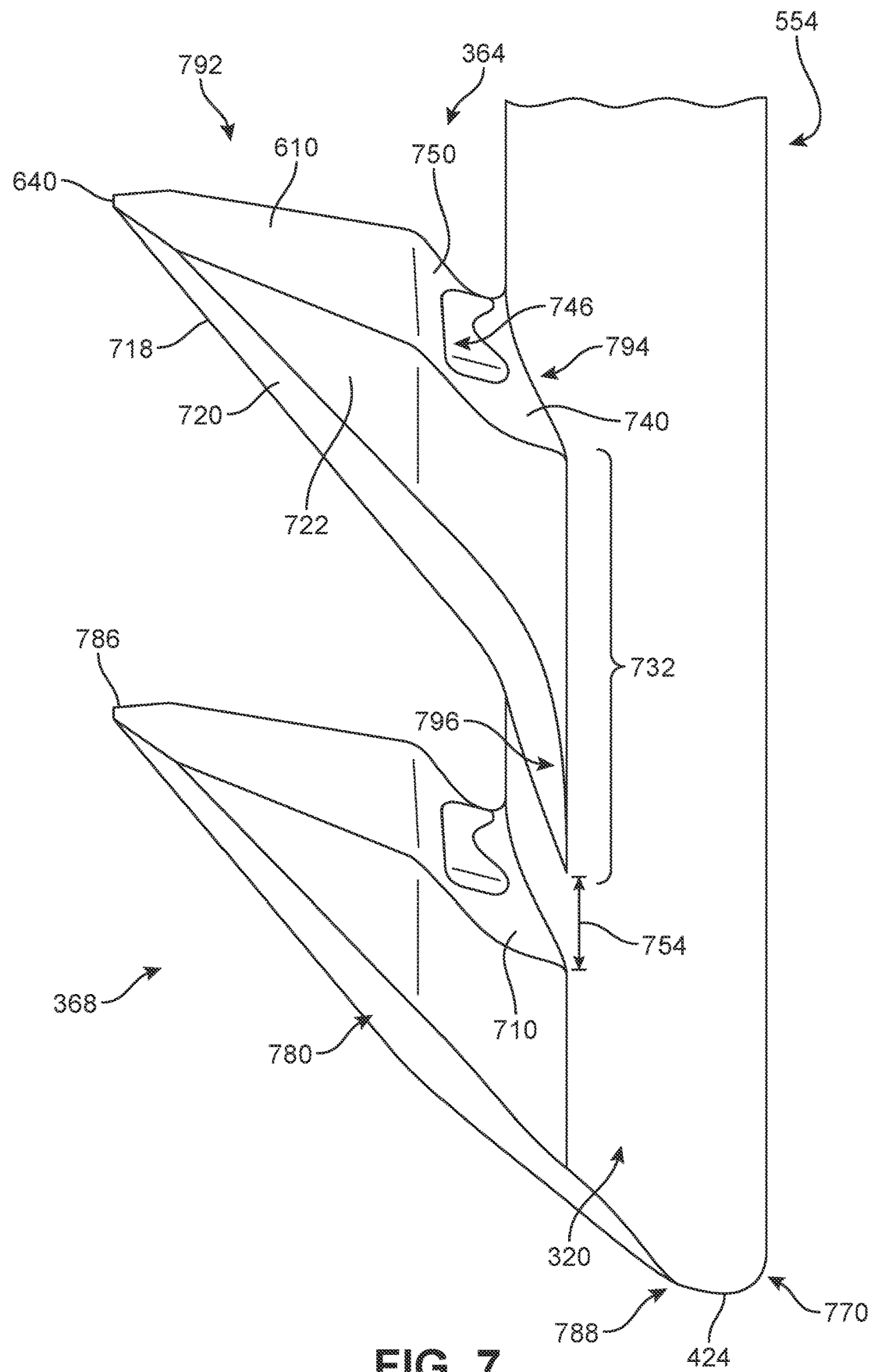
FIG. 7 is a schematic view of a portion of an anchoring device, according to another embodiment.

FIG. 7 presents a magnified view of the distal region 554 of second beam 320, including third barb 364 and fourth barb 368. Because the anchoring device 300 is substantially symmetrical it should be understood that details provided for third barb 364 may also be applicable to the first barb and details for fourth barb 368 may also be applicable to the second barb. In FIG. 7, a first tapered portion 792 of third barb 364 can be seen to include multiple surface sides, including a proximal facing top surface 610, a first lower surface 720, a first side surface 722, and a ridge surface 718. In some embodiments, the tapered portion can include a roughly semi-pyramidal three-dimensional shape. In addition, because anchoring device 300 is symmetrical across lateral axis 370 in the direction of transverse axis 380, it can be understood that the tapered portion 792 also includes a second lower surface and a second side surface on the opposite side. Each of the four surfaces comprising ridge surface ("ridge") 718, top surface 610, first lower surface 720, and second lower surface (not shown) merge into tip portion 640, which can have a narrow, rounded tip or a more pointed or sharp tip. In addition, first lower surface 720 can be seen to extend partially underneath a first base portion 794 of third barb 364. First base portion 794 protrudes outward from a base 732 that is joined to the second beam 320, and includes an arm portion 796 that extends distally downward toward fourth barb 368 until tapering to a point. First base portion 794 also includes a first upper surface defining a recess 750. That is, the proximal facing upper surface 610 may be separated from beam 320 by recess 750. Recess 750 provides barb 364 with a hooked shape, which prevents pull out from tissue. It also provides a narrower base profile, which facilitates penetration into tissue. In addition, in order to provide this narrower base profile with reinforcement, a reinforcing rib 746 may be disposed within recess 750. The reinforcement rib 746 protrudes upward from recess 750 and extends into the body of the first tapered portion 792 that adds greater structural support to the barb.

A spacing 754 between the two barbs can be more clearly seen in FIG. 7, extending from the end of the arm portion 796 of the third barb 364 to a second upper surface 710 of the fourth barb 368. While the two barbs can be understood to be very similar, one structural feature of fourth barb 368 that differs from third barb 364 is the shape of the lower surface. While third barb 364 had a first lower surface 720 that continued until reaching arm portion 796, a lowermost surface 780 of the fourth barb 368 can be seen to extend further as a smooth and continuous plane from a tip 786 to an outer edge portion 788, abutting the teardrop-shaped second bottom surface 424 (see FIG. 4B), along a bottommost end 770 of second beam 320.

Figure 8:
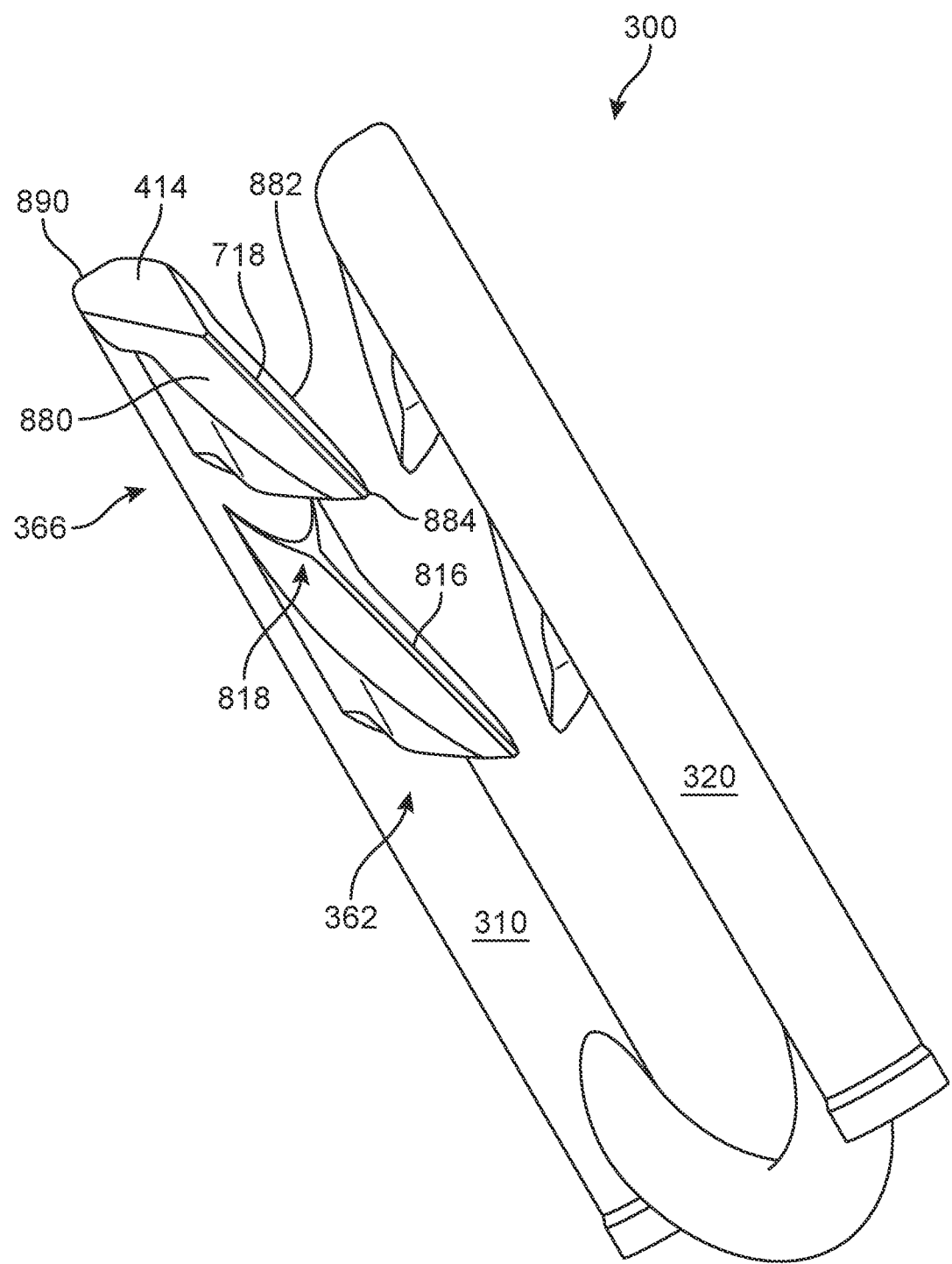
FIG. 8 is a schematic perspective side view of an anchoring device, according to an embodiment.

Further structural details of barbs can be seen in the upside-down view of FIG. 8. In FIG. 8, the surfaces of first barb 362 and second barb 366 are presented, more clearly illustrating the ridges of each. Second barb 366 includes first bottom surface 414 extending diagonally in a proximal direction from a bottommost end 890 of first beam 310 until reaching a first ridge 718. First ridge 718 is a substantially rectangular panel that runs along the bottom of the tapered portion of the second barb 366 and extends in a more sharply upward direction than first bottom surface 414. The first ridge 718 corresponds to a central region of the barb where a first lower surface 880 and a second lower surface 882 come together. The first lower surface 880, second lower surface 882, first ridge 718, and top surface (not shown) merge into a tip 884. In contrast, a second ridge 816 of first barb 362 extends further along the distal surface of the barb, until forking into two prongs 818 toward opposing sides of the first beam 310, thereby forming a Y-shape.

The anchoring device of the embodiments can be implanted using an assembly that extends needle pairs and anchoring devices from a distal tip of the deployment device. The needles pierce into the tissue of the patient. Then, the needles are retracted, while a pushing member maintains the position of the anchoring device relative to the deployment device, thus leaving the anchoring device in the graft and/or tissue. In some embodiments, the general method for implanting an anchoring device described above can be accomplished using a deployment device such as that described below. Specifically, the deployment device may include both a pushing member, as well as components that can actuate the pushing member to simultaneously drive the needle pairs and anchoring device through a graft and into underlying tissue. The deployment device can then release the anchoring device into the graft and/or tissue by retracting the needles.

Figure 9:
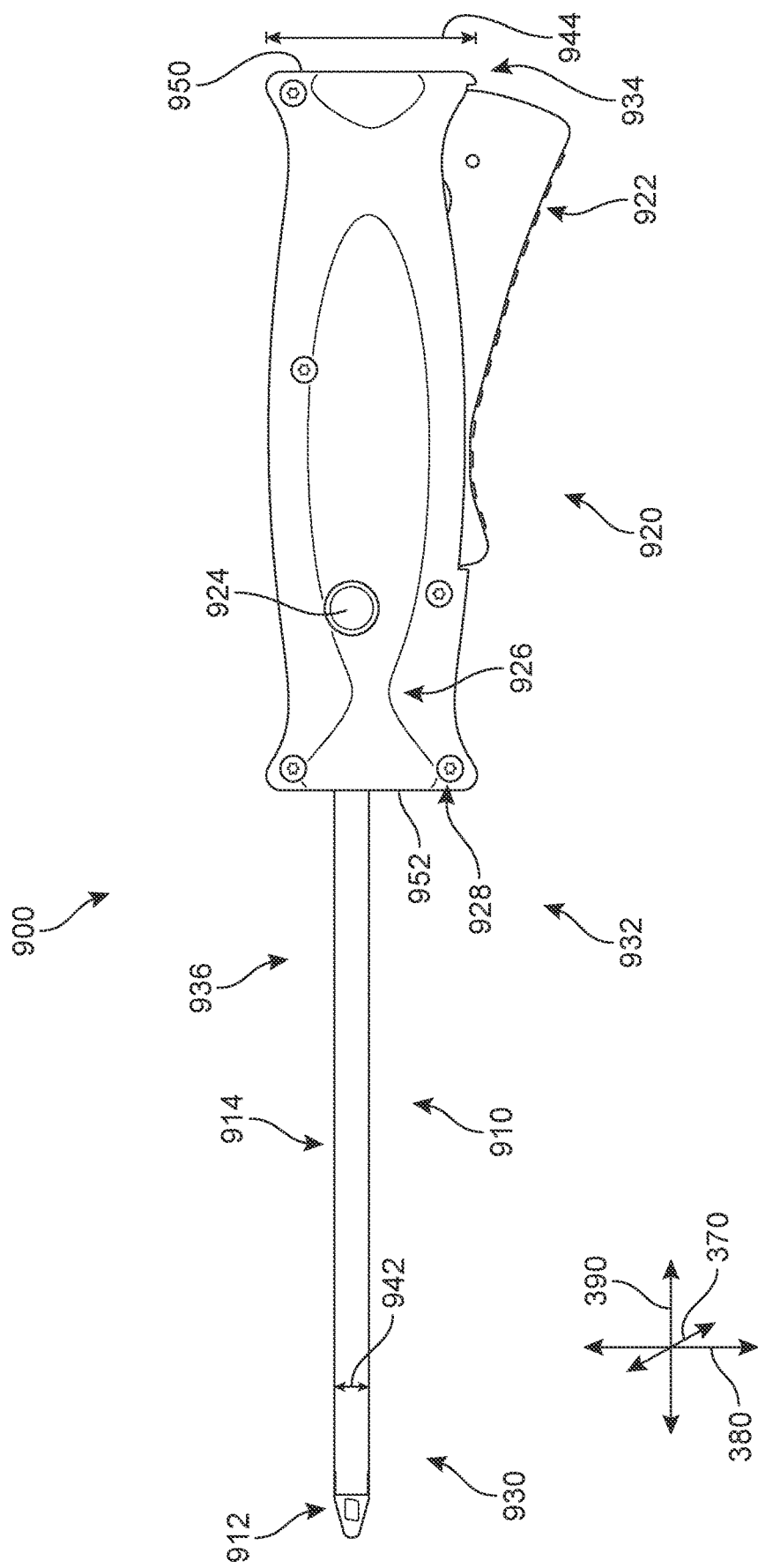
FIG. 9 is a schematic side view of a deployment device, according to an embodiment.
Figure 10:
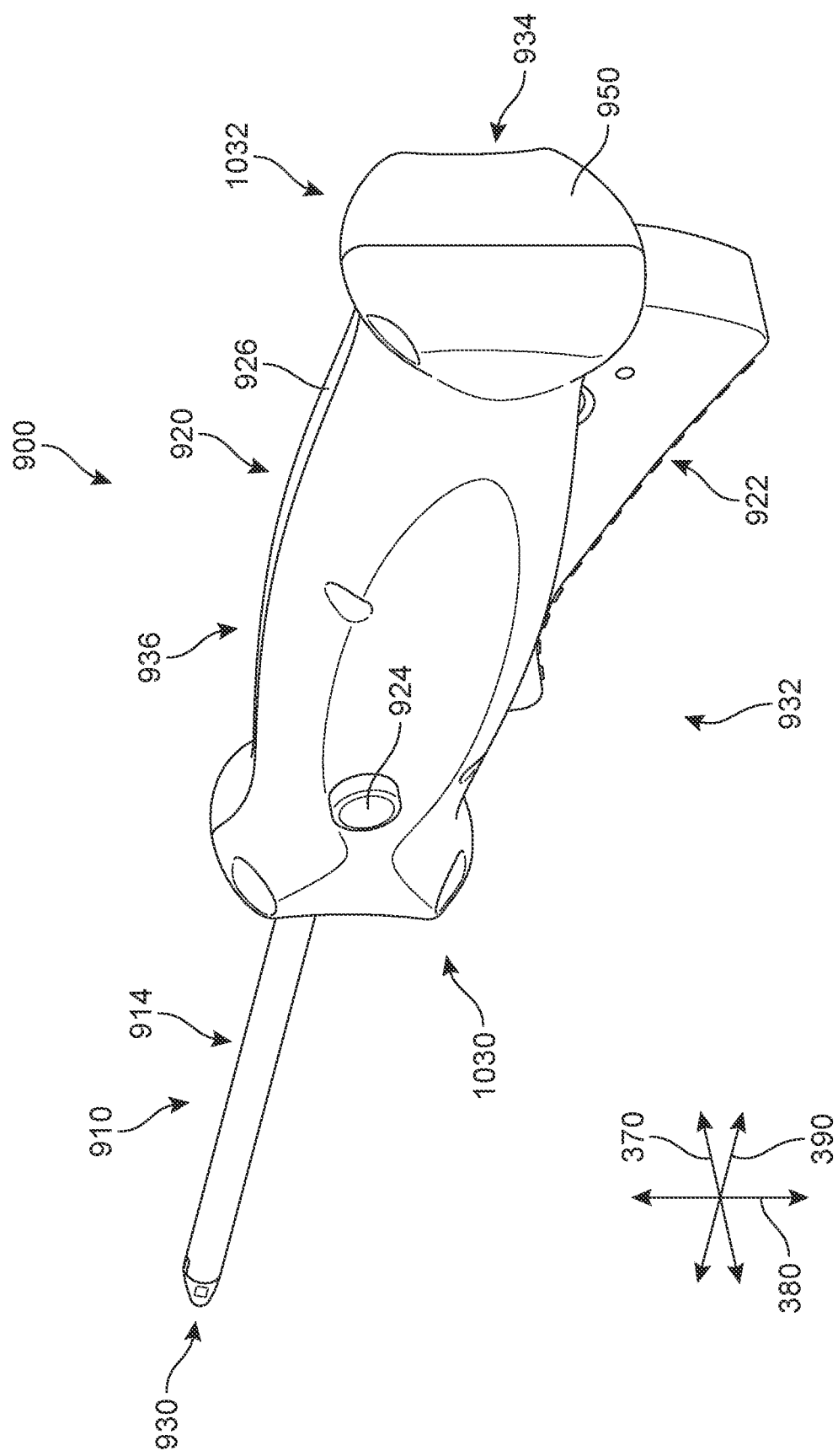
FIG. 10 is a schematic perspective rear view of a deployment device, according to an embodiment.
Figure 11:
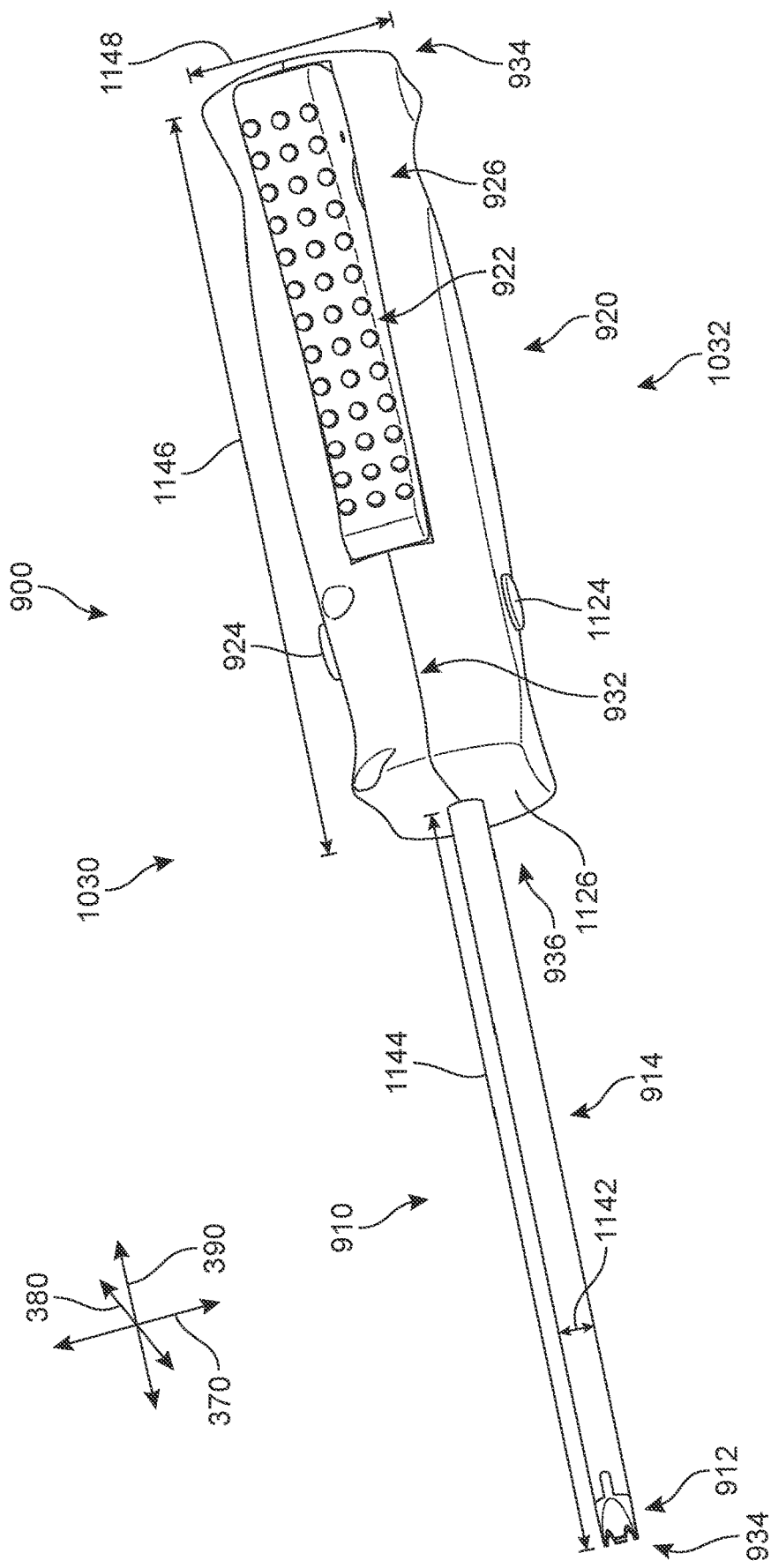
FIG. 11 is a schematic bottom view of a deployment device, according to an embodiment.
Figure 12:
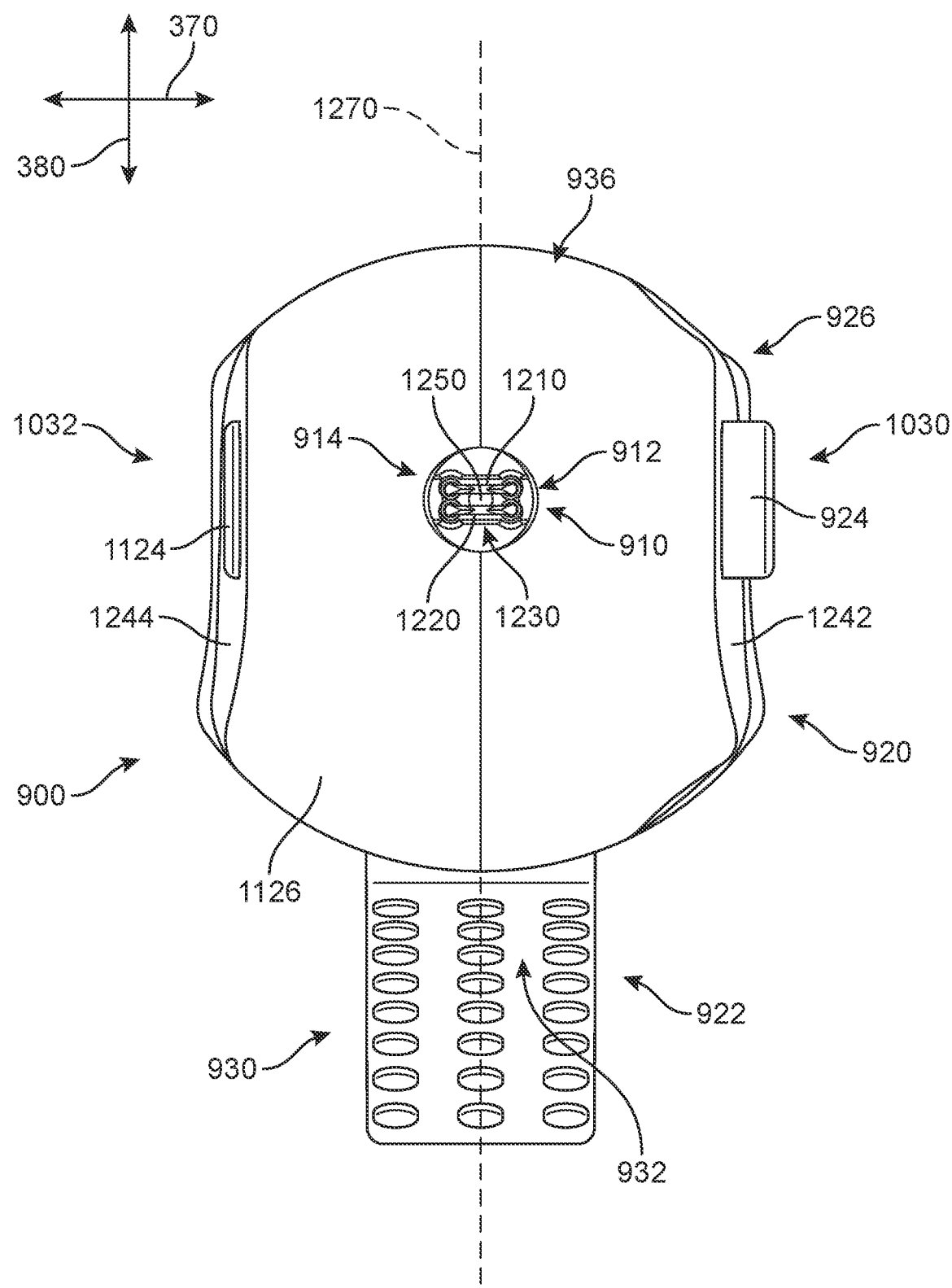
FIG. 12 is a schematic illustration of a deployment device, according to an embodiment viewed from a distal end of the device.

FIG. 9 is a schematic exterior side view of an example of a deployment device 900. Additional schematic views of deployment device 900 are shown in FIGS. 10-12. Deployment device 900 can be used to deploy an anchoring device comprised of two beams with barbed portions and unbarbed portions (for example, anchoring device 300 of FIG. 3). In particular, deployment device 900 can be used to deploy the anchoring device discussed earlier into tissue.

As shown in FIG. 9, deployment device 900 is comprised of a body portion ("body") 920 that is coupled to a deployment tube assembly ("tube assembly") 910. In this exterior view, the body 920 can be seen to include an external housing 926 extending longitudinally between a forward end 952 and a rear end 950, as well as a handgrip trigger 922, a plurality of fasteners 928, and an optional first selector button 924 that is currently in an unpressed, neutral, initial, protruding, or default state. The fasteners 928 in this case are secured within recesses formed in the housing 926. In addition, in some embodiments, the handgrip trigger 922 can have a forward portion that protrudes outward before curving up toward the housing 926 and then extending downward to provide a larger second portion, thereby providing contours that form a user-friendly gripping unit. For purposes of convenience, terms such as forward, front, etc. may also be used to describe features disposed toward a distal end of the deployment device, while terms such as rearward, rear, back, etc. may also be used to describe features disposed toward a proximal end of the deployment device. In the exterior views of FIGS. 9-12, the deployment tube assembly 910 can be seen to comprise a tube housing 914 that is connected to a tip portion 912. A maximum first transverse width 942 of the tube assembly 910 is significantly smaller than a maximum second transverse width 944 of the body 920. Deployment tube assembly 910 may include provisions for inserting an anchoring device through a graft and/or tissue, and will be discussed further with reference to FIGS. 14A-16.

For purposes of reference, in FIG. 9 and other figures, the deployment device 900 is presented with directional labels, including a distal end 930 (toward the tip portion 912), a proximal end 934 (toward the rear end 950), a lower side 932, and an upper side 936. In FIGS. 10-12, a first side 1030 and a second side 1032 (relative to a central lateral axis 1270) are also identified. In some embodiments, first side 1030 and second side 1032 represent two complementary, and in some cases, substantially symmetrical or mirror-image portions of deployment device 900 relative to central lateral axis 1270.

In FIG. 11, a bottom-side-up perspective view of deployment device 900 is shown. It can be seen that tube housing 914 is substantially cylindrical (i.e., with a substantially circular cross-sectional shape in a lateral plane), where a first lateral width 1142 is equal or approximately the same as the first transverse width 942 in FIG. 9. In other embodiments, the tube housing 914 may have an oval or oblong cross-sectional shape. In addition, the body 920 has a second lateral width 1148 that is smaller than the second transverse width 944 of FIG. 9. Furthermore, in some embodiments, a first longitudinal length 1144 of the tube assembly 910 is similar to a second longitudinal length 1146 of the body 920, though in other embodiments, the dimensions of each component may differ based, for example, on the dimensions of the anchoring device being implanted. For example, in some embodiments, the tube assembly may be much longer than the body portion in order to provide greater flexibility of movement to an operator. FIG. 11 also more clearly depicts the selector mechanism, including the two selector buttons, namely first selector button 924 and second selector button 1124 disposed on the opposite side. Second selector button 1124 is, for purposes of illustration, in the depressed state in FIG. 11, and has an outer surface that is nearly flush with the outer surface of the housing 926.

In addition, in some embodiments, the handgrip trigger 922 may include a texturing or other surface patterns that can improve the security of a user's grip on the device. For example, as shown in FIG. 11, handgrip trigger 922 may include nubs or bumps to improve grip.

In the forward-facing view of FIG. 12 (facing toward distal side 930) additional details of the tube assembly 910 can be seen. The tube assembly 910 extends from the body 920 in the region surrounding a transverse midline 1270 (extending from upper side 936 to lower side 932) that demarcates the region in which a first housing side 1242 joins to a second housing side 1244. While in some embodiments the deployment device 900 may be configured to deliver one anchoring device before requiring a 'reload', in some embodiments, the deployment device 900 can include a dual deployment system whereby two anchoring devices may be stored at the same time, allowing for delivery of two different anchoring devices in short order. Such a configuration is shown in FIG. 12, where a primary opening 1230 of the tip portion 912, corresponding to a distal end of the deployment device 900, offers a view of the interior of the tube assembly 910. The tip portion 912 substantially surrounds a first anchoring device ("first anchor") 1210 disposed above and a second anchoring device ("second anchor") 1220 disposed below.

In different embodiments, the first anchor 1210 and second anchor 1210 may correspond to the anchoring device 300 described above. In some embodiments, the two anchors may be arranged within deployment device 900 such that they are substantially symmetrical relative to a longitudinal axis extending through a central point 1250. It may be appreciated that in embodiments in which the deployment device offers dual deployment as described herein, two or more selector buttons may be included. However, in cases where the deployment device includes a single deployment system, only one selector button, or no selector button, may be included.

Figure 13A:
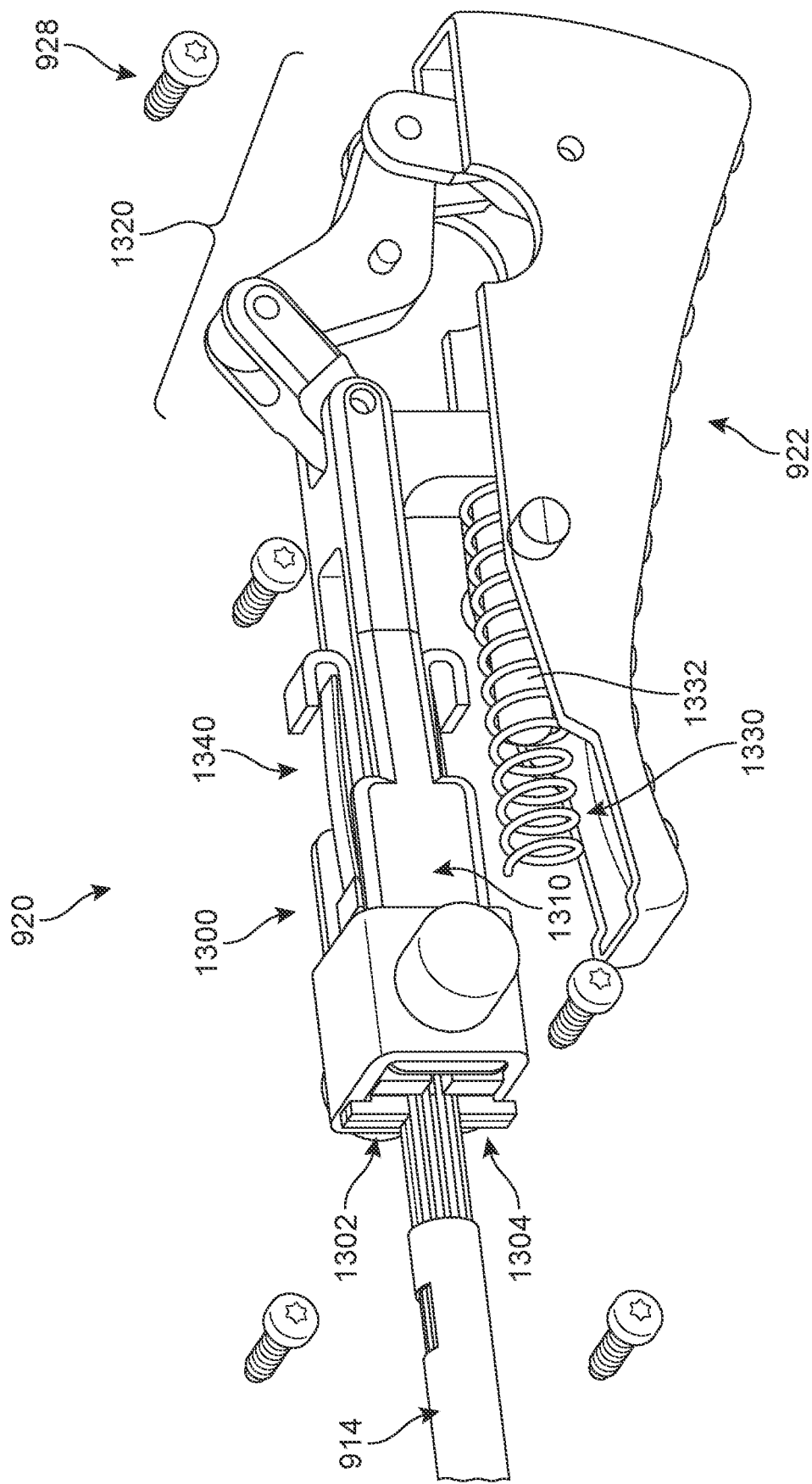
FIG. 13A is a schematic cutaway perspective view of a portion of a deployment device, according to an embodiment.

Referring now to FIG. 13A, for purposes of clarity, an isolated perspective view of the body 920 with the housing removed is presented. Body 920 includes provisions to actuate components of the deployment tube assembly. Body 920 may also include provisions for easily holding deployment device 900. To this end, body 920 may include handgrip trigger 922. Handgrip trigger 922 may be designed to accommodate either a left or right hand. A user's hand may engage handgrip trigger 922 and wrap around a portion of housing 926 in order to squeeze the handgrip trigger 922 upward and actuate the device. It may be appreciated that in some embodiments, a variety of different materials, coatings and/or surface treatments can be used handgrip trigger 620 and housing 926 to improve grip and prevent slipping.

In different embodiments, the handgrip trigger 922 may be coupled to additional actuating components that reside within body 920, and which enable the actuation of a pushing member in the deployment device. For example, the handgrip trigger 922 may, when actuated, cause a change in a linkage assembly 1320 from a first configuration to a second configuration (see FIGS. 17A-26 below). As shown in FIG. 13A, linkage assembly 1320 comprises a plurality of linking components for permitting the extending and contracting of the assembly, as will be discussed in greater detail below. The linkage assembly 1320 can pivot and initiate an actuation sequence in conjunction with an actuation assembly 1300. In different embodiments, the actuation assembly 1300 can include a slider assembly 1310, a compression spring ("spring") 1330, and a set of anchor engaging rod drivers ("drivers") 1340. The spring 1330 surrounds a spring-engaging post or protruding portion 1332, which has an elongated geometry and extends from both sides of the slider assembly 1310. Within an interior space formed in the slider assembly 1310, the drivers 1340 are connected to a set of pushing members (a first pushing member 1302 and a second pushing member 1304) that extend from the tube housing 914 into the body 920 (see FIGS. 14A-15). Pushing members may also be referred to herein as needle blocks.

Figure 13B:
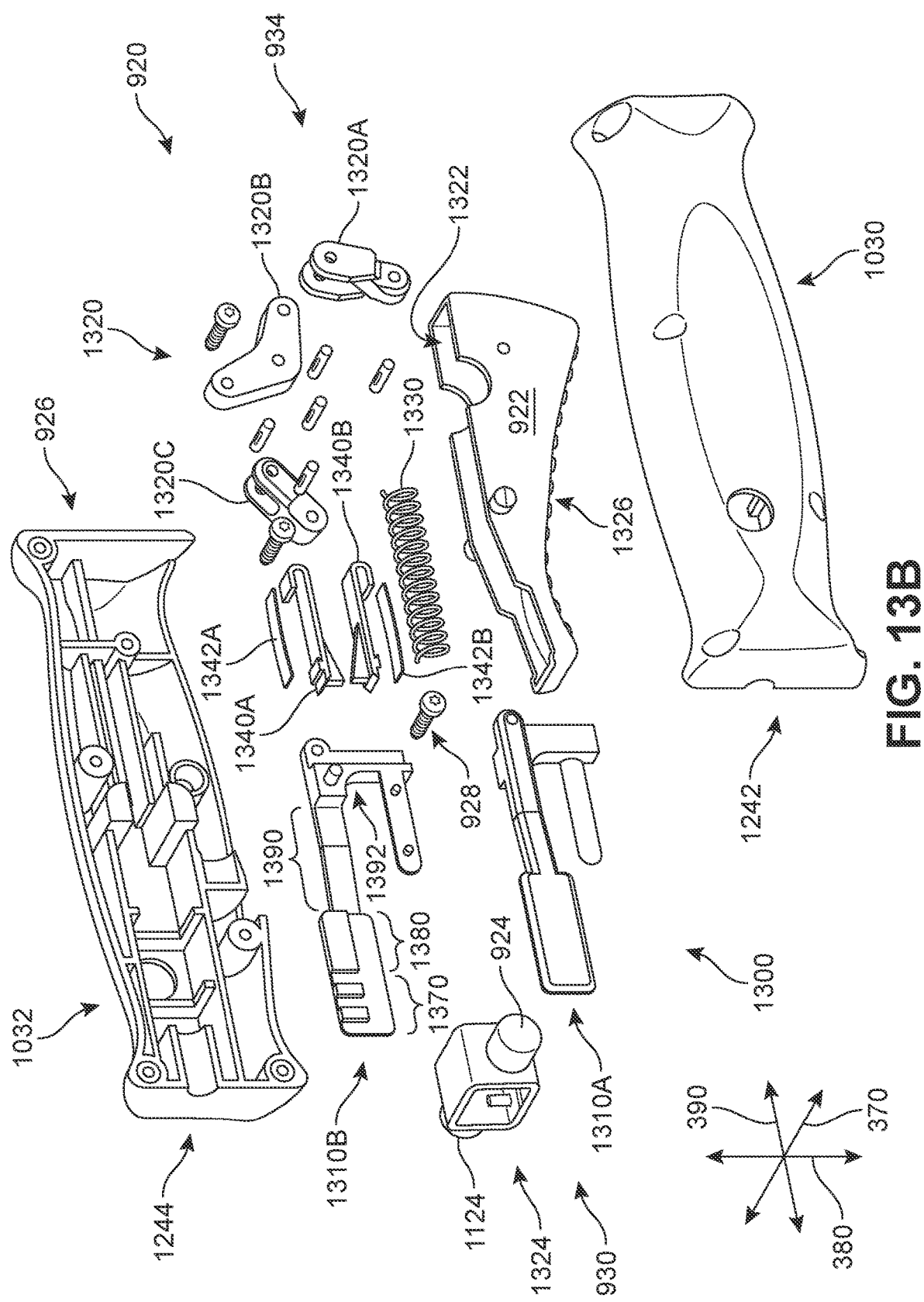
FIG. 13B is a schematic exploded view of the body portion of the deployment device of FIG. 13A, according to an embodiment.

In order to provide the reader with a greater understanding of the components housed in body 920, an exploded perspective view of the body 920 is illustrated in FIG. 13B. In FIG. 13B, the housing 926 can be seen to comprise first housing side 1242 and second housing side 1244. The handgrip trigger 922 includes a substantially hollow interior space 1322 designed to receive and movably connect with a lower portion of a first link 1320a of linkage assembly 1320. In some embodiments, the trigger 922 further includes a set of pivoting or rocker elements (shown here as two knobs extending outward from exterior surface of the trigger 922), operation of which will be discussed further below. In addition, as noted above, in some embodiments, trigger 922 may include gripping elements 1326 that can improve a user's grip on the device.

With reference to the linkage assembly 1320, first link 1320a is movably connected to a second link 1320b, and second link 1320b is movably connected to a third link 1320c, which is movably connected to slider assembly 1310, seen here to comprise a first sliding component 1310a and a second sliding component 1310b. For purposes of reference, the second sliding component 1310b is shown as comprising several regions, including a first region 1370, a second region 1380, a third region 1390, and a fourth region 1392. The first region 1370 and second region 1380 together comprise a forward region 1376 of the sliding component. In addition, first region 1370 of the sliding component includes tongue portions or ridges 1308 that extend medially inward. The ridges 1308 in each sliding component are sized and dimensioned to engage with a plurality of grooves formed along the sides of the pushing members (see FIGS. 17B and 17C). The fourth region 1392 includes portions that are configured to engaged with the linkage assembly 1320. While only the second sliding component 1310b includes the above labels, it should be understood that these regions are also present in first sliding component 1310a. In one embodiment, each sliding component is complementary or a mirror-image with respect to the opposing sliding component, except for the location of the ridges in first region 1370. More specifically, the ridges in the first sliding component 1310a are disposed near or abut an uppermost edge of the first region, and the ridges in the second sliding component 1310a are disposed near or abut a lowermost edge of the first region.

In different embodiments, the third link 1310c is configured to pivot around and relative to the protruding portion 1332 that extends from the medial-facing sides of the fourth region 1392 of each sliding component. Surrounding the first region 1370 is selector assembly 1324, which comprises two selector buttons and a substantially rectangular opening into which slider assembly 1310 extends. Depression of a selector button on either side can push against the adjacent sliding component in a medial direction, in turn engaging the corresponding pushing member (see FIG. 20). The set of drivers 1340, including a first driver 1340*a* and a second driver 1340*b*, are arranged symmetrically or mirror-images relative to one another and are disposed between first sliding component 1310*a* and second sliding component 1310*b*. The first driver 1340*a* further includes a first driver spring 1342*a* and the second driver 1340*b* includes a second driver spring 1342*b*.

Figure 14A:
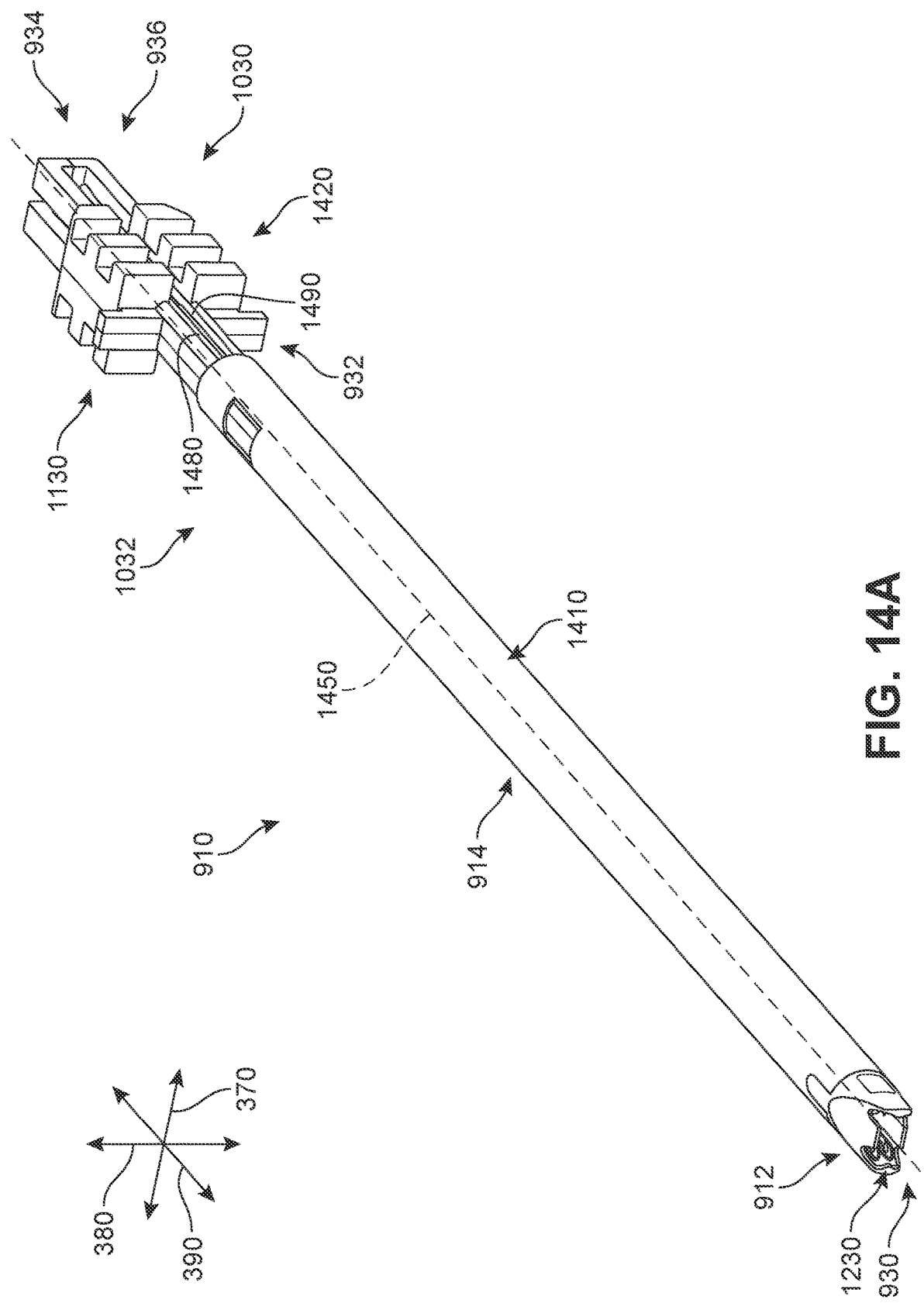
FIG. 14A is a schematic perspective view of a deployment tube assembly, according to an embodiment.

Referring now to FIG. 14A, for purposes of context, an isolated perspective view of the tube assembly 910 is shown. The tube assembly 910 includes a tip portion 930 with primary opening 1230 at its distal end from which the anchor is released. The tip portion 930 is joined to the elongated tube housing 914 in which multiple components and portions thereof are disposed. Extending outward from a rear or proximal opening are a pair of pushing members 1420 (comprising the first pushing member and second pushing member). Disposed within a channel formed along a first side of the upper pushing member is a first anchor engaging rod 1480, and disposed within a channel formed along a first side of the lower pushing member is a second anchor engaging rod 1490. In some embodiments, each channel includes a slit opening from which the anchor engaging rods can be seen. In one embodiment, the interior components of the tube housing 914 are arranged substantially symmetrically relative to a central longitudinal axis 1450.

Figure 14B:
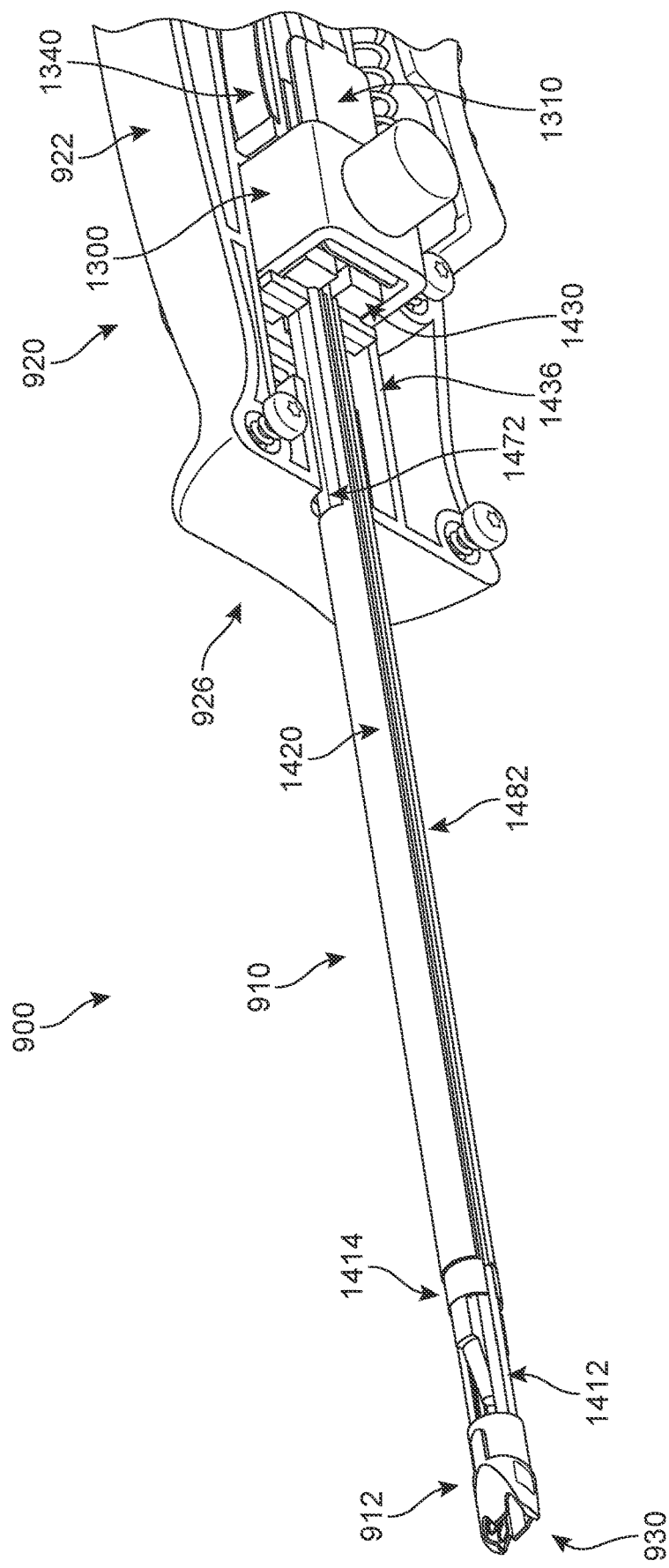
FIG. 14B is a schematic cutaway perspective view of a portion of a deployment device, according to an embodiment.

Turning to FIG. 14B, the tube assembly 910 is depicted without the exterior tube housing 914, revealing the interior deployment components. The pushing members 1420 can be seen to extend from a region adjacent to and behind tip portion 930 until entering the housing 926 of body 920 through an aperture 1472 formed on the distal end of the housing 926. A rear portion 1436 of the pushing members 1420 then extends proximally into housing 926 and contacts with components of actuation assembly 1300. For example, in FIG. 14B, engaging portions 1434 of the pushing members 1420 are partially disposed between the two sliding components comprising the slider assembly 1310. Also visible are the two anchor engaging rods 1482 extending along the sides of the pushing members 1420 that are configured to engage with drivers 1342 (see FIG. 13B). In some embodiments, the anchor engaging rods 1482 are further movably secured or retained within the channels formed in pushing members 1420 by retaining clips 1414.

Figure 15:
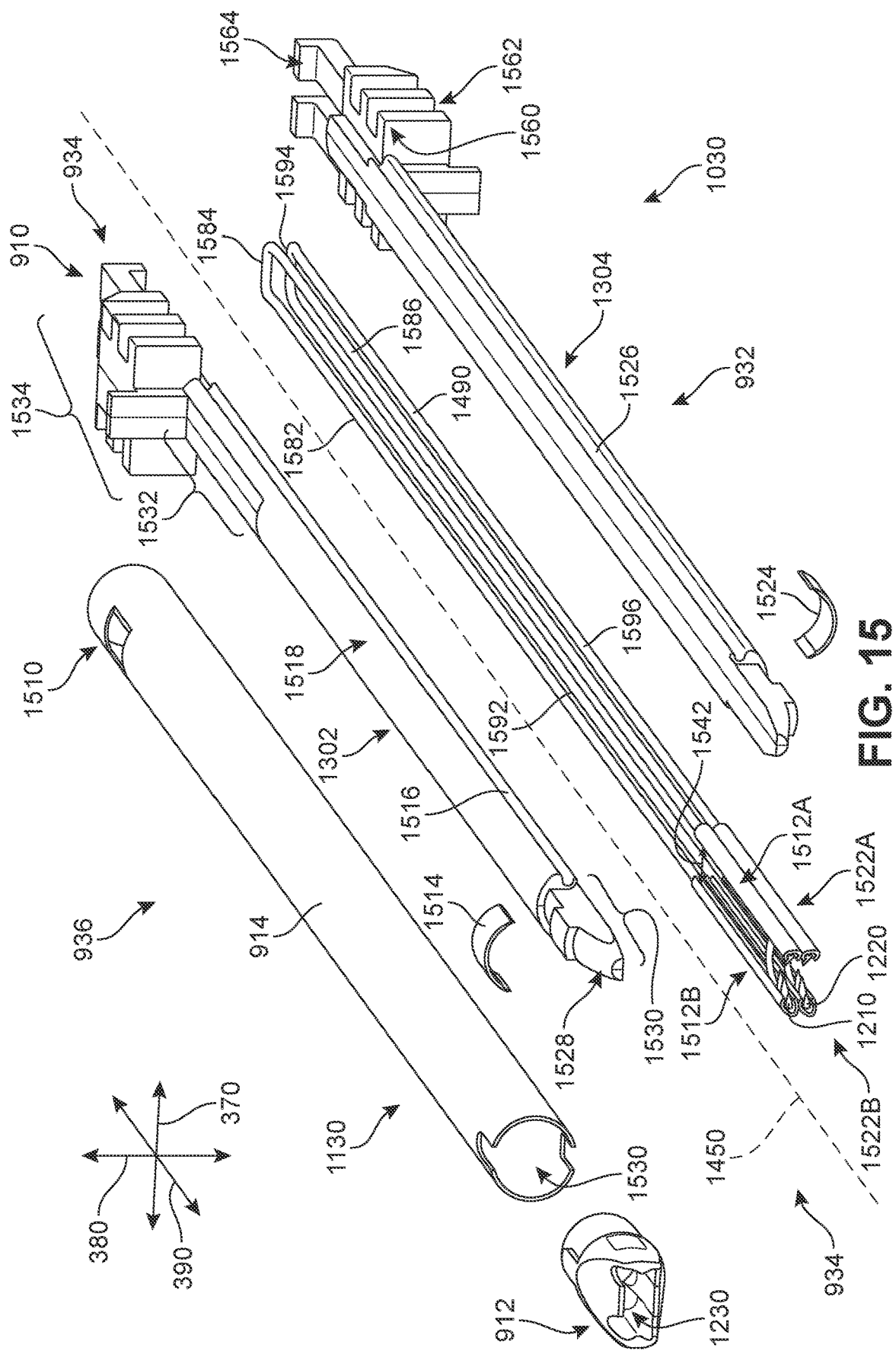
FIG. 15 is a schematic exploded view of the tube assembly of the deployment device of FIGS. 14A and 14B, according to an embodiment.

In order to better illustrate the distinct components of tube assembly 910, an exploded perspective view of the tube assembly 910 is illustrated in FIG. 15. As noted above, tube assembly 910 includes provisions to deploy one or more anchors from the tube assembly 910. In this example, an exterior of tube assembly 910 includes tube housing 914 and tip portion 912, and provides a continuous interior compartment extending from primary opening 1230 and continuing into a secondary opening 1530 formed in a distal end of tube housing 914. In some embodiments, the compartment is substantially cylindrical in shape. In some embodiments, the tube housing 914 also includes window openings 1510 that provide a view of the interior configuration or state of the pushing members. For example, a first window may be present on an upper surface of the tube housing 914, and a second window may be present on a lower surface of the tube housing 914. In some cases, the two windows can be aligned with one another relative to the transverse axis 380.

In the example of FIG. 15, interior components of tube assembly 910 includes first pushing member 1302 and second pushing member 1304, the first anchor engaging rod 1480, the second anchor engaging rod 1490, a first retaining clip 1514, a second retaining clip 1524, a first needle member 1512*a*, a second needle member 1512*b*, a third needle member 1522*a*, and a fourth needle member 1522*b*. When the deployment device has been loaded, the tube assembly 910 also includes one or both of first anchor 1210 and second anchor 1220.

In different embodiments, the first pushing member 1302 and second pushing member 1304 can be substantially similar in shape and dimensions, though oriented in opposing directions. Thus, when assembled, a substantially flat underside of first pushing member 1302 faces directly toward and in some cases can be in contact with a substantially flat upper surface of second pushing member 1304. For purposes of reference, the first pushing member 1302 is shown as comprising several portions, including a forward portion 1530 (further including a nose portion 1528), an intermediate portion 1518, a recessed portion 1532, and an engaging portion 1534. While only the first pushing member 1302 includes such labels in FIG. 15, it should be understood that these portions are also present in second pushing member 1304 as well.

In some embodiments, when deployment device is in its initial or neutral configuration (prior to actuation), both forward portion 1530 and intermediate portion 1518 are disposed within the tube housing 914. However, when deployment device is in the actuated configuration, the nose portion 1528 can move forward from tube housing 914 into the tip portion 912 in order to push the anchor and needle members in a distal direction out of primary opening (e.g., see FIG. 30). In addition, while recessed portion 1532 and engaging portion 1534 are discussed herein as comprising components of the tube assembly 910, they are each configured to extend into the body housing and/or engage with components disposed in the body of the deployment device. The engaging portion of each pushing member further includes a plurality of grooves 1562 formed between the spaces between a pair of ledges 1560, and an end portion 1564 (shown here with reference to second pushing member 1304). Further details regarding engaging portion 1534 will be discussed below in FIGS. 17A-C.

In some embodiments, the first anchor engaging rod 1480 and the second anchor engaging rod 1490 can be substantially similar in shape and dimensions, though oriented in opposing directions. In this example, each anchor engaging rod includes an elongated U-shape comprising three portions. Thus, first anchor engaging rod 1480 includes a first prong or arm 1582 that is substantially parallel to and aligned with a second prong or arm 1586. The first prong 1582 and second prong 1586 are bridged together by a first hook portion 1584. Similarly, second anchor engaging rod 1490 includes a third prong or arm 1592 that is substantially parallel to and aligned with a fourth prong or arm 1596. The third prong 1592 and fourth prong 1596 are bridged together by a second hook portion 1594.

Central longitudinal axis 1410 was first represented in FIG. 14A. It is also included in FIG. 15, and should be understood to extend through a centerline of the tube assembly 910. Thus, the medial direction (i.e., toward the center) from any component of tube assembly 910 should be understood to be a direction that extends toward the central longitudinal line 1410. It may be appreciated that while the majority of the prong portions of each anchor engaging rod are substantially linear and parallel to the central longitudinal axis 1410, the hook portions are U-shaped. Thus, each anchor engaging rod comprises a continuous, elongated U-shaped rod. Furthermore, each hook portion is oriented diagonally relative to the central longitudinal axis 1410. In other words, each hook portion is slightly bent in a direction away from central longitudinal axis 1410. Thus, first hook portion 1584 is a U-shaped segment that bends or curves upward, and second hook portion 1594 is a U-shaped segment that bends or curves downward. The functions of the hook portions will be discussed with reference to FIGS. 18-25 below.

As noted earlier, each pushing member also includes channels for receiving portions of each anchor engaging rod. In FIG. 15, first pushing member 1302 can be seen to include a first channel 1516 that extends along the first side 1030 of a lower edge of the intermediate portion 1518 and recessed portion 1532. Although not shown here, it should be understood that a second channel is similarly formed on the second side 1130 of the intermediate portion 1518 and recessed portion 1532. In addition, second pushing member 1304 includes a third channel 1526 and a fourth channel that is formed on the opposite side. Each channel is shaped and sized to snugly accommodate the prongs of each anchor engaging rod, providing a secure hold of the prong while also allowing smooth movement back and forth along the channel. In some embodiments, the channel has a longitudinal opening with a transverse width that is smaller than the diameter of the prong disposed within the channel in order to prevent the prong from escaping from the channel. Similarly, the recessed portion 1532 of each pushing member is configured to slide back and forth between the body of the deployment device and the tube housing 914 via the aperture formed in the body housing. Thus, the recessed portion 1532 has a smaller transverse thickness and a substantially flat upper surface, allowing it to move smoothly through the body housing.

In some embodiments, the tube assembly 910 includes provisions for releasing each anchor from the deployment device. As shown in FIG. 15, the tube assembly 910 further includes needle members for holding anchors and to provide a space in which anchor engaging rods can interact with loaded anchors. More specifically, a first beam of first anchor 1210 is housed in or movably retained by an elongated chamber formed in first needle member 1512a and a second beam of first anchor 1210 is housed in or movably retained by an elongated chamber formed in second needle member 1512b. Similarly, a first beam of second anchor 1220 is movably retained in or held by an elongated chamber formed in third needle member 1522a and a second beam of second anchor 1220 is movably retained in or held by an elongated chamber fourth formed in fourth needle member 1522b.

Furthermore, the barbs and connecting member of each anchor (see FIG. 3) extend outward from each needle member through an elongated slit formed along a medial side of each needle member, allowing the anchor to be disposed in both needle members simultaneously. To this end, the two needle members are spaced apart a first distance 1582 that corresponds to the lateral width of the connecting member. Thus, in some embodiments, the barbs and connecting member of each anchor are exposed within the tube assembly 910 relative to the first beam and second beam which are retained in the chambers of needle members. It can be understood that each chamber is shaped and sized to snugly accommodate the beams of each anchor, providing a secure hold of the beam while also allowing smooth movement of the anchor back and forth along the chamber. In other words, each elongated slit has a transverse width that is smaller than the diameter of the beam and larger than the diameter of the connecting member and transverse width of the barbs in order to securely retain the anchor in the two needle members, and allow retraction of the needle members until the anchors are released such that deployment occurs.

In order to ensure each needle member maintains its position relative to the pushing member when the pushing member translates back and forth within the deployment device, in some embodiments, the pushing member and needle member may be secured or otherwise fastened together. For example, in FIG. 15, first needle member 1512a and second needle member 1512b are held or joined to forward portion 1530 of the first pushing member 1302 by first retaining clip 1514. Similarly, third needle member 1522a and fourth needle member 1522b are held or joined to the forward portion of the second pushing member 1304 by second retaining clip 1524. The curved retaining clip is secured within a recessed region provided in the forward portion 1530 sized and dimensioned to snugly receive the retaining clip, and the retaining clip 'hugs' the proximal ends of the needle member such that the needle member is held flush and securely in place against a substantially concave sidewall region of the forward portion.

Figure 16:
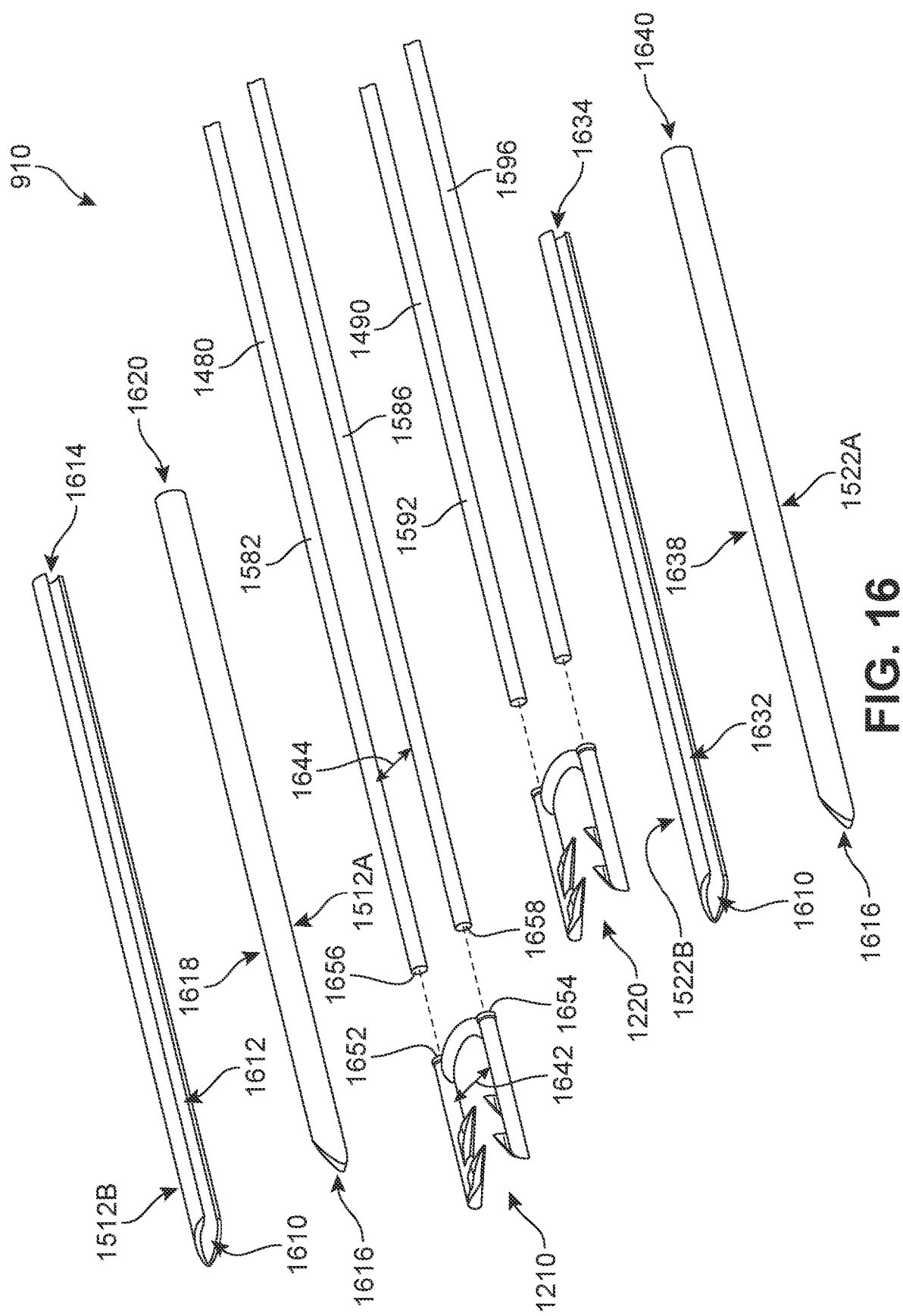
FIG. 16 is a schematic exploded view of a distal portion of the tube assembly of the deployment device of FIGS. 14A and 14B, according to an embodiment.

Additional details regarding the distal end of the tube assembly 910 are now provided with reference to FIG. 16, which depicts a partial exploded perspective view of components of the tube assembly 910. For purposes of clarity, the four needle members have been isolated in FIG. 16, and the anchors and anchor engaging rods have been removed from the needle members. As noted above, in some embodiments, each of the needle members may be understood to be substantially similar components. Thus, it can be observed that first needle member 1512a includes a forward opening 1616 and a rear opening 1620, and similarly second needle member 1512b includes a forward opening 1610 and a rear opening 1620. In addition, third needle member 1522a includes a forward opening 1636 and a rear opening 1640, and similarly fourth needle member 1522b includes a forward opening 1630 and a rear opening 1634. Furthermore, second needle member 1512b can be seen to include a first slit 1612 extending across the longitudinal length of the tube and fourth needle member 1522b includes a second slit 1632 extending across the longitudinal length of the needle member. It should be understood that first needle member 1512a and third needle member 1512b also includes such slits, allowing for the free movement of the anchor through the needle members from the forward opening to the rear opening.

The isolated view of first anchor 1210 and first anchor engaging rod 1480 and the similar view of second anchor 1220 and second anchor engaging rod 1490 also offer more clarity regarding the pushing functionality of the deployment device. As shown in FIG. 16, a second distance 1644 between the first prong 1582 and the second prong 1586 is substantially equal to a third distance 1642 between the first beam and the second beam of first anchor 1210, allowing the two components to be aligned in a longitudinal plane. In addition, a first disc 1652 of first anchor 1210 has a surface area and shape that is substantially similar to that of a first distal end 1656 of the first prong 1582. Similarly, a second disc 1654 of first anchor 1220 has a surface area and shape that is substantially similar to that of a second distal end 1658 of the second prong 1586. Each distal end may also be referred to as a pushing portion or pushing surface herein. As depicted by dotted lines, the two surfaces face one another and are configured to press against one another when actuation occurs. Thus, when the anchor engaging rod moves forward, the adjacent anchor is pushed at the same time in the same direction.

Figure 17A:
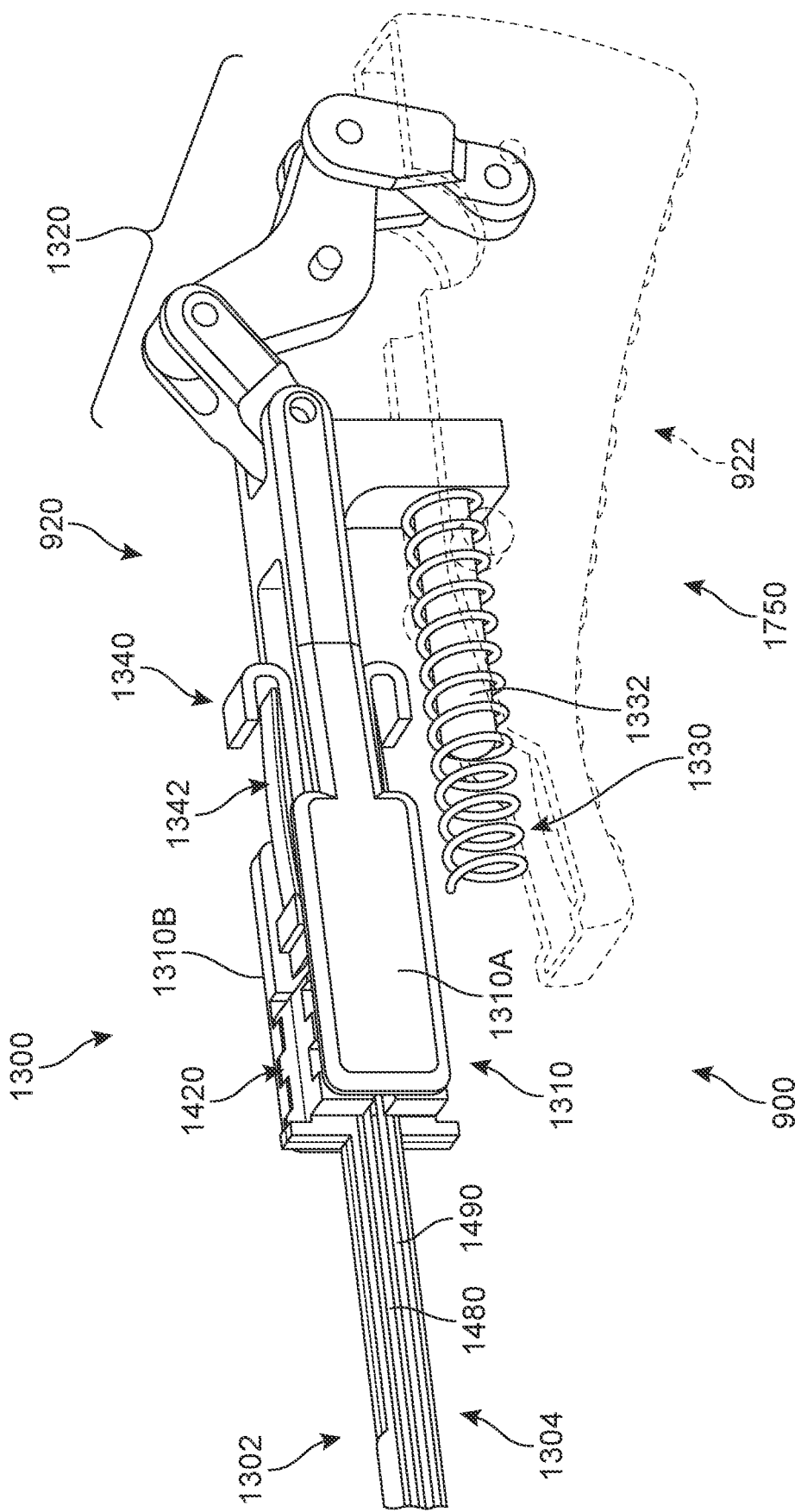
FIGS. 17A-19 present schematic views of a deployment device in a locked configuration with a pair of anchoring devices loaded onto the deployment device, according to an embodiment.

The exemplary configuration of actuating components shown in FIGS. 9-16 provide a way to convert the upward translation of the trigger into a corresponding distal translation of the pushing members. This allows the force generated by squeezing the trigger to be converted into a force that drives an anchor through a graft and underlying tissue. As an example, FIGS. 17A-26 together show how an anchor is made to be deployed from tip portion 912 when the handgrip trigger 922 is squeezed. In FIG. 17A, deployment device 900 is shown in a primary locked configuration 1750, with first pushing member 1302 and second pushing member 1304 retracted or stowed. The primary locked configuration 1750 refers to the state in which the deployment device has not been actuated, but a depression of a selector button has occurred. The neutral position, not shown here, refers to the state in which the deployment device has not been actuated, nor has a selector button been depressed. The spring 1330 is also in its initial extended configuration around the protruding portion 1332. Furthermore, the linkage assembly 1320 is in an initial contracted position. In this first stage, for purposes of example, the second selector button 1124 is depressed, as shown in FIGS. 11 and 12 earlier. In other cases, the first selector button may be depressed first.

Figure 17B:
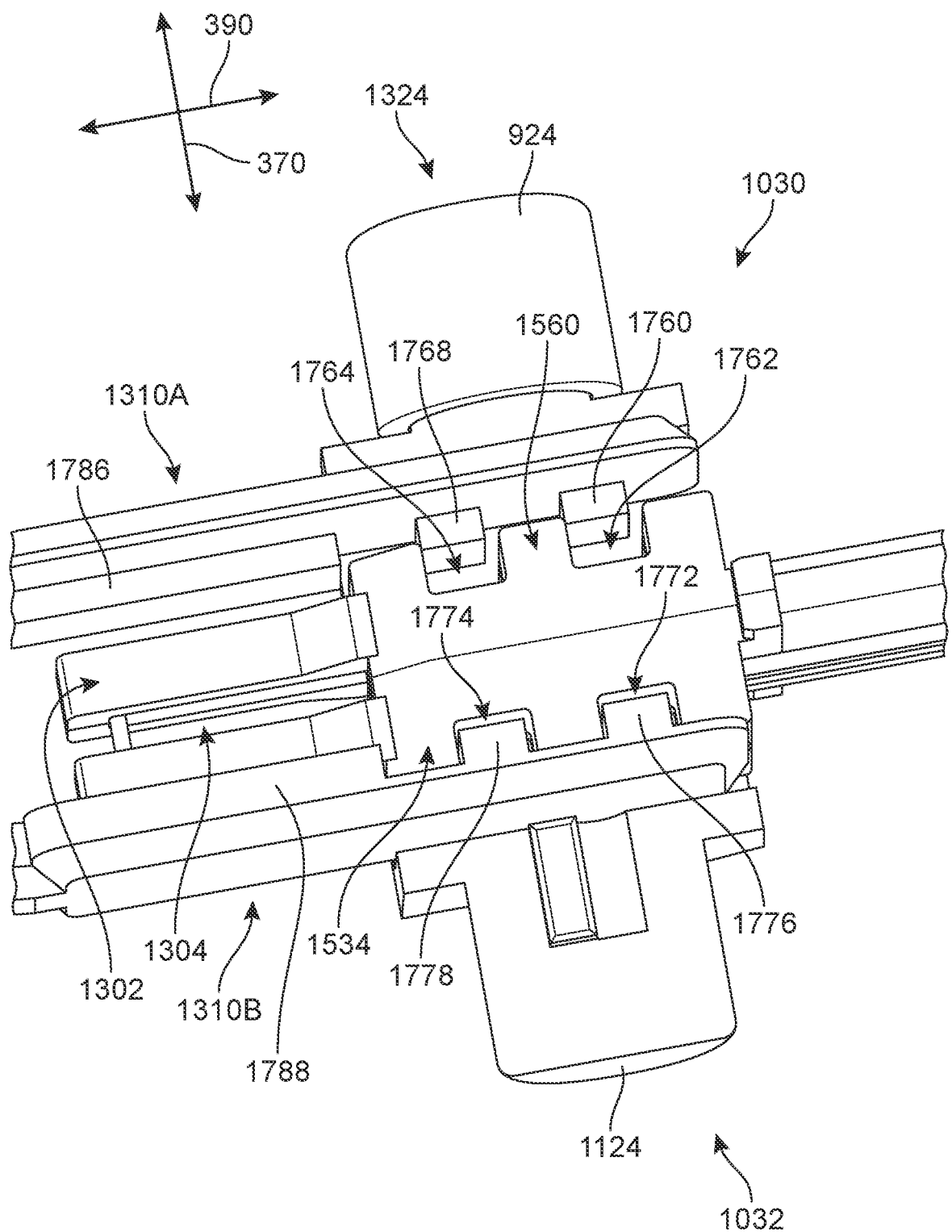
Figure 17C:
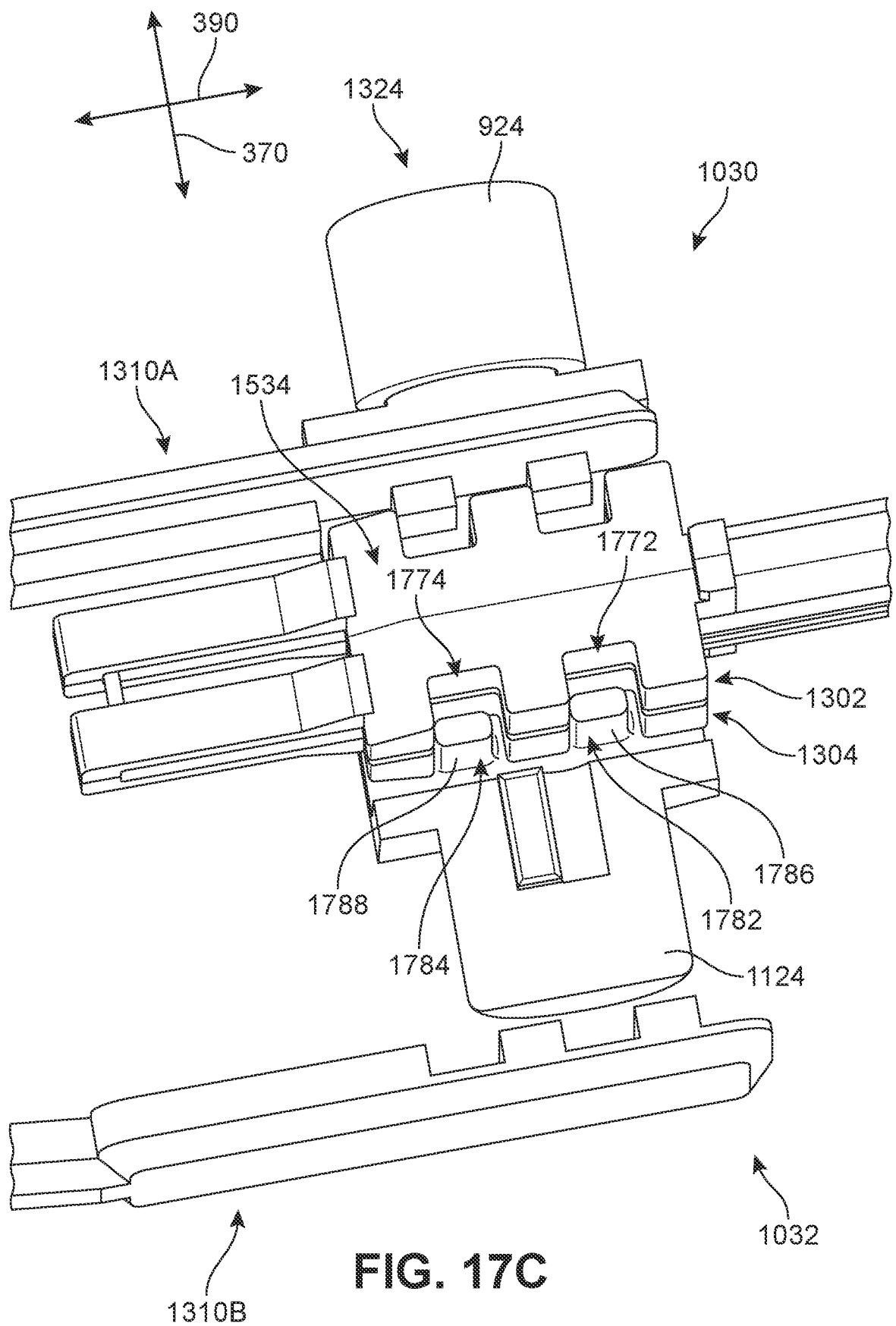

In some embodiments, depression of second selector button 1124 causes a change in the relative position of the second sliding component 1310b in the body 920. This arrangement is now discussed with reference to FIGS. 17B and 17C. When no selector buttons are depressed, both sliding components remain spaced apart from the pushing members. However, once a selector button is depressed, the corresponding sliding component shifts position in order to engage with the adjacent pushing member's engaging portion. FIGS. 17B and 17C provide two perspective cutaway views of the selector assembly 1324. In FIGS. 17A and 17B, engaging portions 1534 of the first pushing member 1302 and second pushing member 1304, as well as the forward region 1376 of each of the first sliding component 1310a and second sliding component 1310b, are presented. The second selector button 1124 has been depressed.

In FIG. 17B, it can be seen that as a result of the depression of second selector button 1124, the second sliding component 1310b has been compressed or pushed inward, such that the two ridges (shown here as a first ridge 1776 and a second ridge 1778) are now inserted into or received by the engaging portion of the first pushing member 1302. More specifically, first ridge 1776 has been inserted into a first groove 1772 and second ridge 1778 has been inserted into a second groove 1774. In different embodiments, the shape and size of each groove is configured to snugly receive each corresponding ridge. Thus, in one embodiment, each ridge lies flush against or directly adjacent to the three inner surfaces comprising each groove. By filling the two groove spaces, the ridges and ledges form a substantially continuous upper surface along the second side 1032 of the engaging portion of the first pushing member 1302. Furthermore, a first rear ridge 1788 is now pressed against the outer side of the end portion of the first pushing member 1302. Thus, the first pushing member 1302 is now 'locked' to the second sliding component 1310b, such that it will hold its relative position with the second sliding component 1310b if the second sliding component 1310b moves forward or rearward.

In contrast, along the first side 1030 of the device, the first selector button 924 remains in the un-pressed, neutral, or initial state. As shown in FIG. 17B, when a selector button has not been depressed, the adjacent sliding component remains spaced apart from the engaging portion of the pushing members. In other words, in this case, a third ridge 1766 is disposed outside of a third groove 1762 formed along the first side 1030 of second pushing member 1302, and a fourth ridge 1768 is disposed outside of a fourth groove 1764 formed along the first side 1030 of the second pushing member 1304. Similarly, a second rear ridge 1786 is also spaced apart from the end portion of the second pushing member 1304. Thus, the second pushing member 1304 is 'unlocked' with respect to the first sliding component 1310a, such that it will not hold its relative position with the first sliding component 1310a if the first sliding component 1310a moves forward or rearward. It should be understood that when neither selector button has been depressed, both sides of the deployment device are in this arrangement, also referred to as the neutral configuration.

As noted earlier with respect to FIG. 13, each sliding component can be complementary or a mirror-image with respect to the opposing sliding component, except for the location of the ridges in the first region 1370. More specifically, the third ridge 1766, fourth ridge 1768, and second rear ridge 1786 are disposed along the lower half of the first region of the first sliding component 1302, and are therefore aligned with the grooves formed in the lowermost second pushing member 1304. Similarly, the first ridge 1776 and second ridge 1778 and first rear ridge 1788 are disposed along the upper half of the first region of the second sliding component 1304, and are therefore aligned with the grooves formed in the uppermost first pushing member 1302.

For purposes of clarity regarding the functionality of the selector buttons, FIG. 17C presents the assembly of FIG. 17B with the second sliding component 1310b removed from the assembly. The mechanism by which the second pushing member 1304 is locked into position is now visible, as well as the stacking arrangement of the first pushing member 1302 over the second pushing member 1304. As shown in FIG. 17C, depression of second selector button 1124 also causes a change in the relative position of the second selector button 1124 in the body 920. When no selector buttons are depressed, both selector buttons remain spaced apart from the pushing members. However, once a selector button is depressed, a set of locking projections shifts position in a medially inward direction in order to engage with the adjacent pushing member's engaging portion.

In FIG. 17C, it can be seen that as a result of the depression of second selector button 1124, the second selector button 1124 has been compressed or pushed inward, such that the two locking projections (shown here as a first projection 1786 and a second projection 1788) are now inserted into or received by the engaging portion of the second pushing member 1304. More specifically, first projection 1786 has been inserted into a fifth groove 1782 and second projection 1788 has been inserted into a sixth groove 1784. In different embodiments, the shape and size of each groove is configured to snugly receive each corresponding projection. Thus, in one embodiment, each projection lies flush against or directly adjacent to the three inner surfaces comprising each groove. By filling the two groove spaces, the projections and ledges form a substantially continuous upper surface along the second side 1032 of the engaging portion of the second pushing member 1304. The second pushing member 1304 is now 'locked' to the second selector button 1124, such that it will hold its relative position with the second selector button 1124 while other neighboring components move forward or rearward. In other words, the first set of grooves formed on the second side 1032 of the first pushing member 1302 have been filled by the ridges of the second sliding component 1310b, and the second set of grooves on the second side 1032 of the second pushing member 1304 have been filled by the projections of the second selector button 1124. Furthermore, the second set of grooves can be understood to be aligned with and disposed directly below the first set of grooves while deployment device is in the primary locked configuration 1750.

Figure 18:
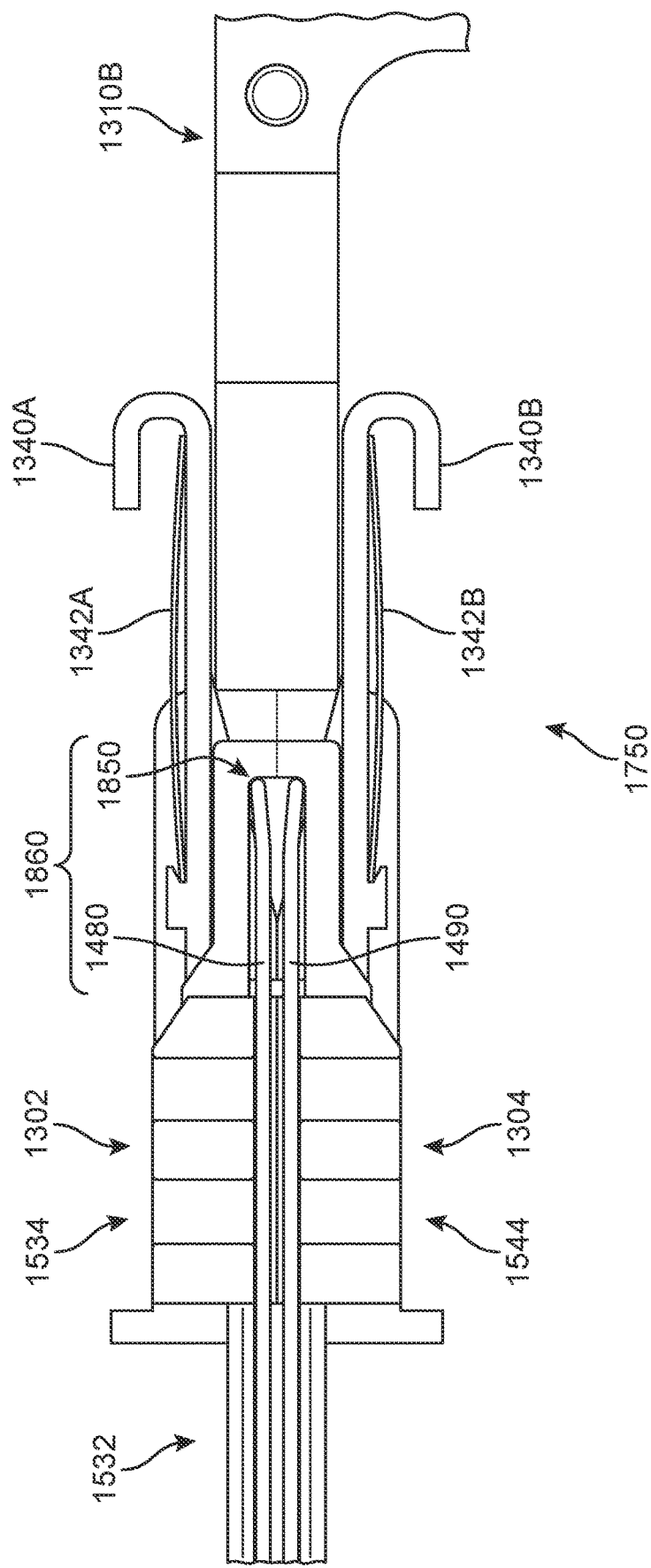

FIG. 18 presents a cutaway side view of a portion of the deployment device in the primary locked configuration 1750 in which the housing and first sliding component have been removed to reveal the relative arrangement of the pushing members, anchor engaging rods, and drivers. In FIG. 18, it can be observed that the system is substantially symmetrical with respect to the central longitudinal axis. Thus, the first pushing member 1302 is disposed directly above and aligned with the second pushing member 1304, the first anchor engaging rod 1480 is disposed directly above and aligned with the second anchor engaging rod 1490, and the first driver 1340a is disposed directly above and aligned with the second driver 1340b. In addition, the two anchor engaging rods can be seen to extend through an opening or space formed between the L-shaped end portion 1564 of the two pushing members. The hook portions of each anchor engaging rod are disposed behind driver head portions 1860, such that each hook portion surrounds or wraps around a lateral width of the adjacent driver. In some embodiments, the proximal end of the hook portion, curving away from the central longitudinal axis, is in contact with and/or presses against a corner 1850 formed in the L-shaped end portion of each pushing member. Furthermore, the recessed portion 1532 of both pushing members can be understood to be disposed primarily within the body housing (not shown).

Figure 19:
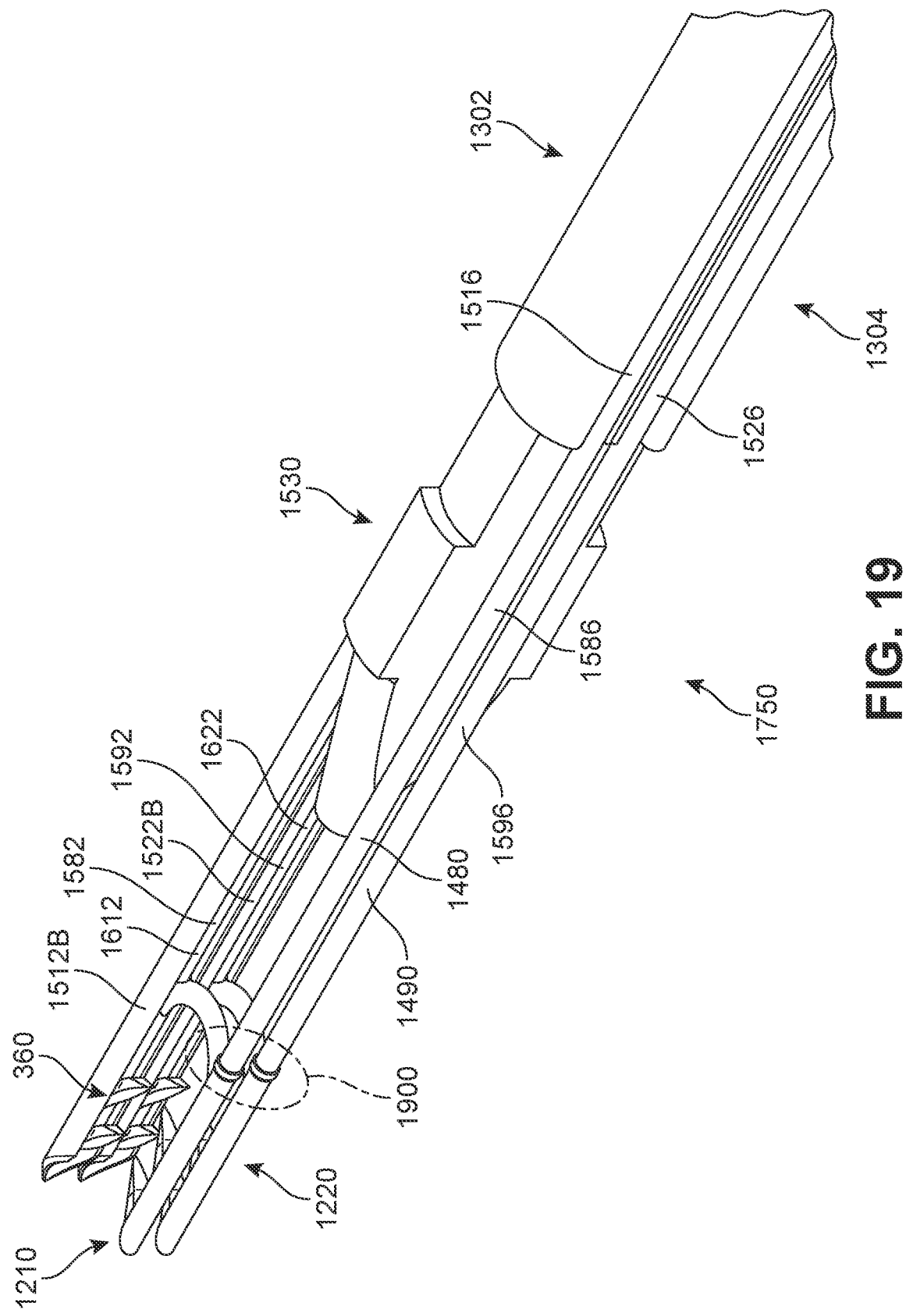

FIG. 19 presents a cutaway perspective view of a portion of the deployment device in the primary locked configuration 1750 in which the tube housing, tip portion, and two needle members have been removed to reveal the relative arrangement of the pushing members, anchor engaging rods, and anchors. In FIG. 19, it can be observed that the system is substantially symmetrical with respect to the central longitudinal axis. Thus, the nose portions of the first pushing member 1302 and second pushing member 1304 are aligned with one another, the first anchor engaging rod 1480 is disposed directly above and aligned with the second anchor engaging rod 1490, the second needle member 1512b is disposed directly above and aligned with the fourth needle member 1522b, and the first anchor 1210 is disposed directly above and aligned with the second anchor 1220. The removal of the first needle member and third needle member also more clearly illustrates the relationship between the lower ends (discs) of the anchors with the distal ends of the anchor engaging rods, whereby the anchor engaging rods are in direct contact with each anchor.

Referring now to FIGS. 20-23, deployment device 900 is shown in a primary actuated configuration 2050, with first pushing member 1302 slid forward and second pushing member 1304 retaining its original position. The spring 1330 is now in its compressed configuration around the protruding portion 1332. Furthermore, the linkage assembly 1320 has transitioned from its contracted position to an extended position. In this second stage, the second selector button 1124 continues to be depressed, as described in FIGS. 17A-19 above.

In some embodiments, the trigger 922 is configured to pivot in either a first rotary direction or an opposing second rotary direction via a pair of cylindrical rocker elements that extend outward from the trigger 922 and are movably or rotatably secured in small tubes formed in the housing. Thus, depression of the proximal end of the trigger 922 causes rotation of the trigger 922 such that the proximal end moves upward in the first rotary direction while the distal end moves downward. In other words, the distal end of the trigger 922 is at a lowermost position, and the proximal end of the trigger 922 is at an uppermost position.

Figure 20:
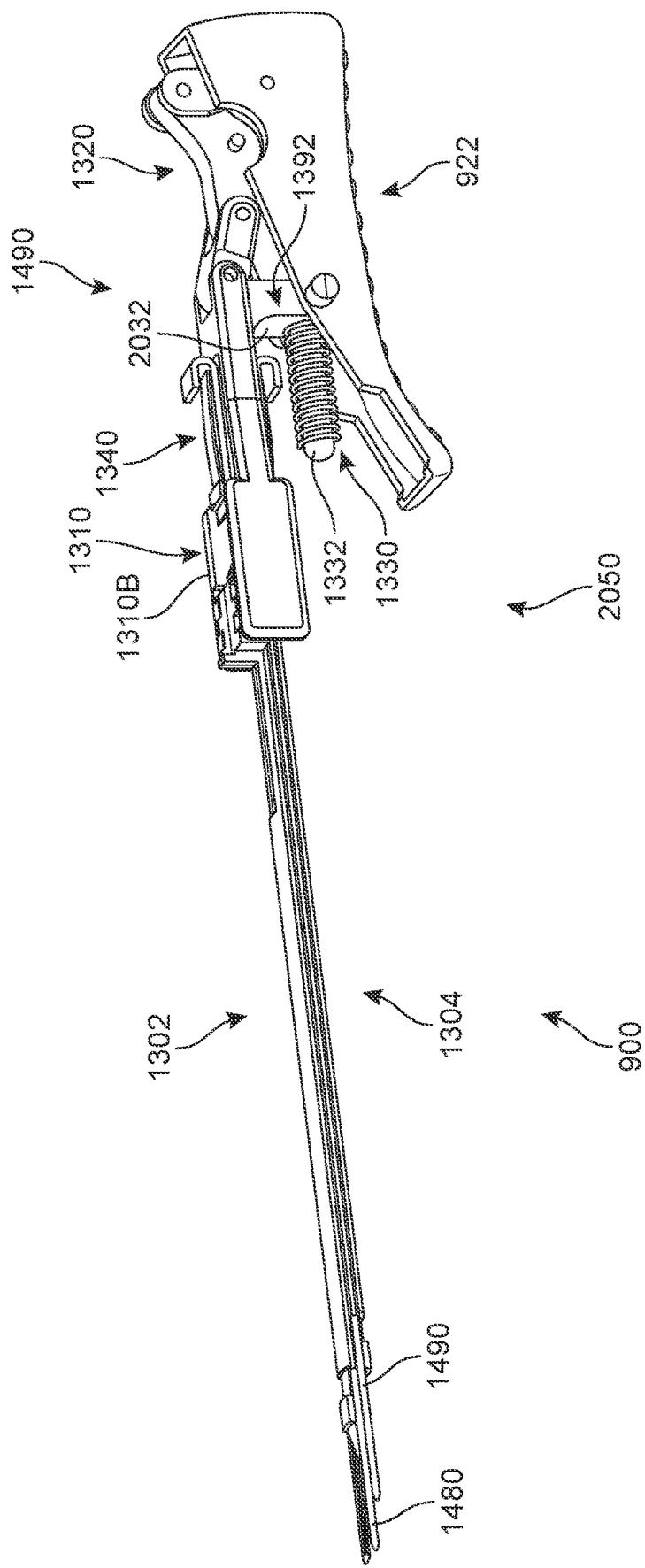
FIGS. 20-23 present schematic views of the deployment device in an actuated configuration, according to an embodiment.

In the perspective of FIG. 20, as trigger 922 is compressed, it can be seen that the trigger 922 pivots in a generally counter-clockwise direction. Furthermore, trigger 922 is biased to return to its neutral position, by way of spring 1330 which extends around the protruding portion 1332. The motion of the trigger 922 as it moves upward is translated into further rotational motion by the pivoting portions of the linkage assembly 1320, causing the linkage assembly 1320 to straighten and lengthen in the longitudinal direction. This same motion causes the slider assembly 1310 to be pushed forward, resulting in a compression of the spring 1330 around protruding portion 1332 as it meets and presses against a distal surface 2032 of the fourth region 1392 of slider assembly 1310.

As discussed with respect to FIGS. 17B and 17C, the engaging portion of the first pushing member 1302 is locked to the sliding component 1310b in this example (due to the depression of the second selector button). Thus, when slider assembly 1310 is pushed distally forward from an initial or first position to an actuated or second position, first pushing member 1302 is also carried or pushed forward the same distance into the actuated position. In contrast, second pushing member 1304, being locked to the second selector button, retains its original, stowed position. Furthermore, the recessed portion of the first pushing member is now disposed primarily within the tube housing (not shown), while the recessed portion of the second pushing member is disposed primarily within the body housing (not shown).

Figure 21:
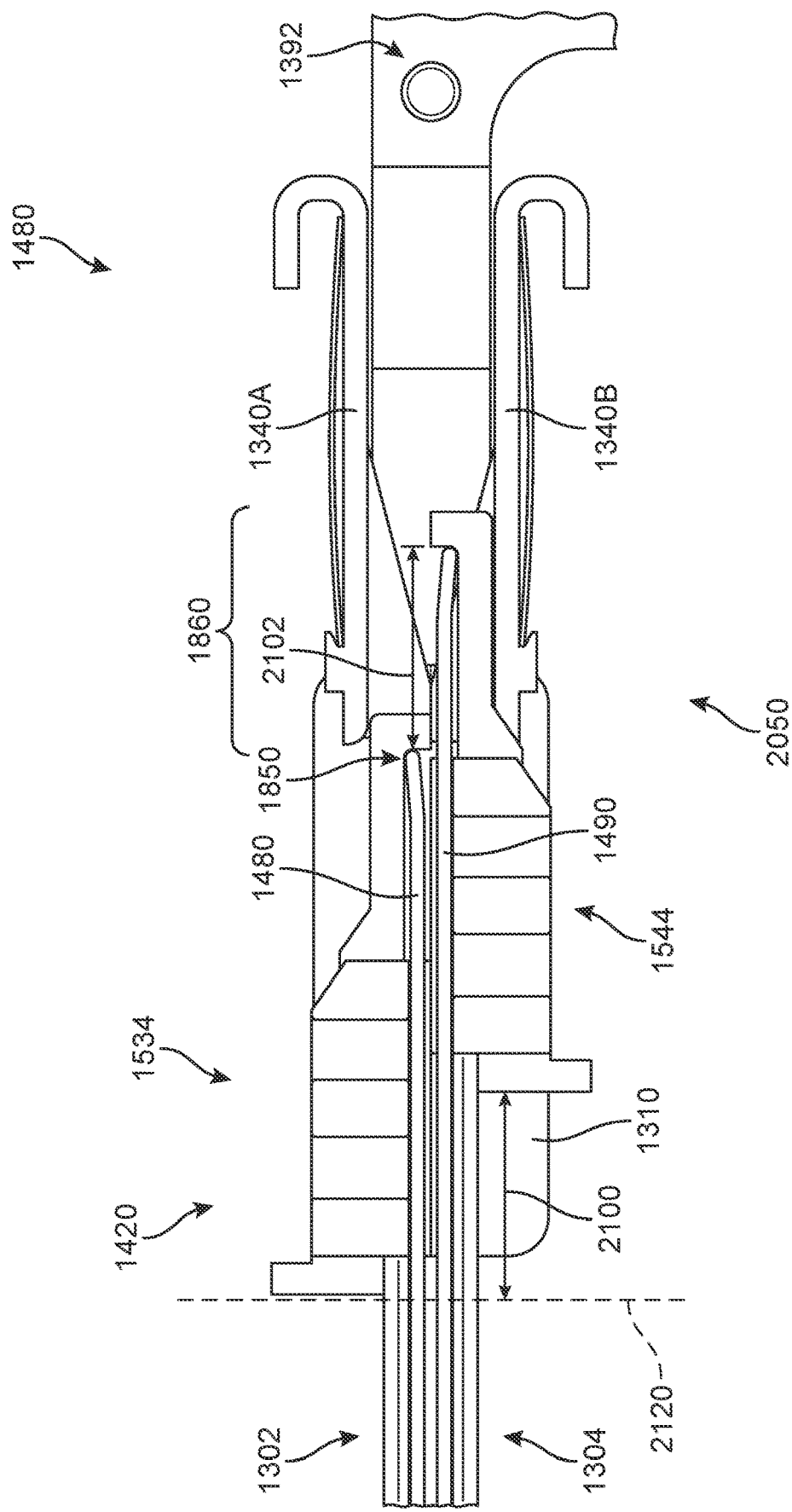

The new relative positioning of the first pushing member 1302 to the second pushing member 1304 is more clearly observable in the cutaway side view of the deployment device in FIG. 21. In this view, the housing and first sliding component have again been removed to reveal the relative arrangement of the pushing members, anchor engaging rods, and drivers. In FIG. 21, it can be observed that the system, in this configuration, is no longer substantially symmetrical with respect to the central longitudinal axis. Thus, the first pushing member 1302 is now disposed more distally relative to the second pushing member 1304 by a fourth distance 2100, and the first anchor engaging rod 1480 is disposed more distally relative to the second anchor engaging rod 1490 by a fifth distance 2102. In one embodiment, fifth distance 2102 is substantially similar to the fourth distance 2100. However, it is important to note that both the first driver 1340a and second driver 1340b retain their positions during this stage and remain aligned relative to one another, even as the slider assembly 1310 has translated forward. However, the relative position of the slider assembly 1310 to the two drivers has changed such that both drivers are now disposed nearer to the fourth region 1392 of the slider assembly 1310 than in the first stage.

In addition, while the hook portion of the second anchor engaging rod 1490 is still disposed behind the driver head portions 1860, the first anchor engaging rod 1480 has moved forward such that it no longer extends around the head portion of either driver. Rather, the first anchor engaging rod

1480 is now completely distal relative to the first driver 1340a, having been pushed forward by the distal surface of the corner 1850 of the L-shaped end portion of the first pushing member 1302.

Figure 22:
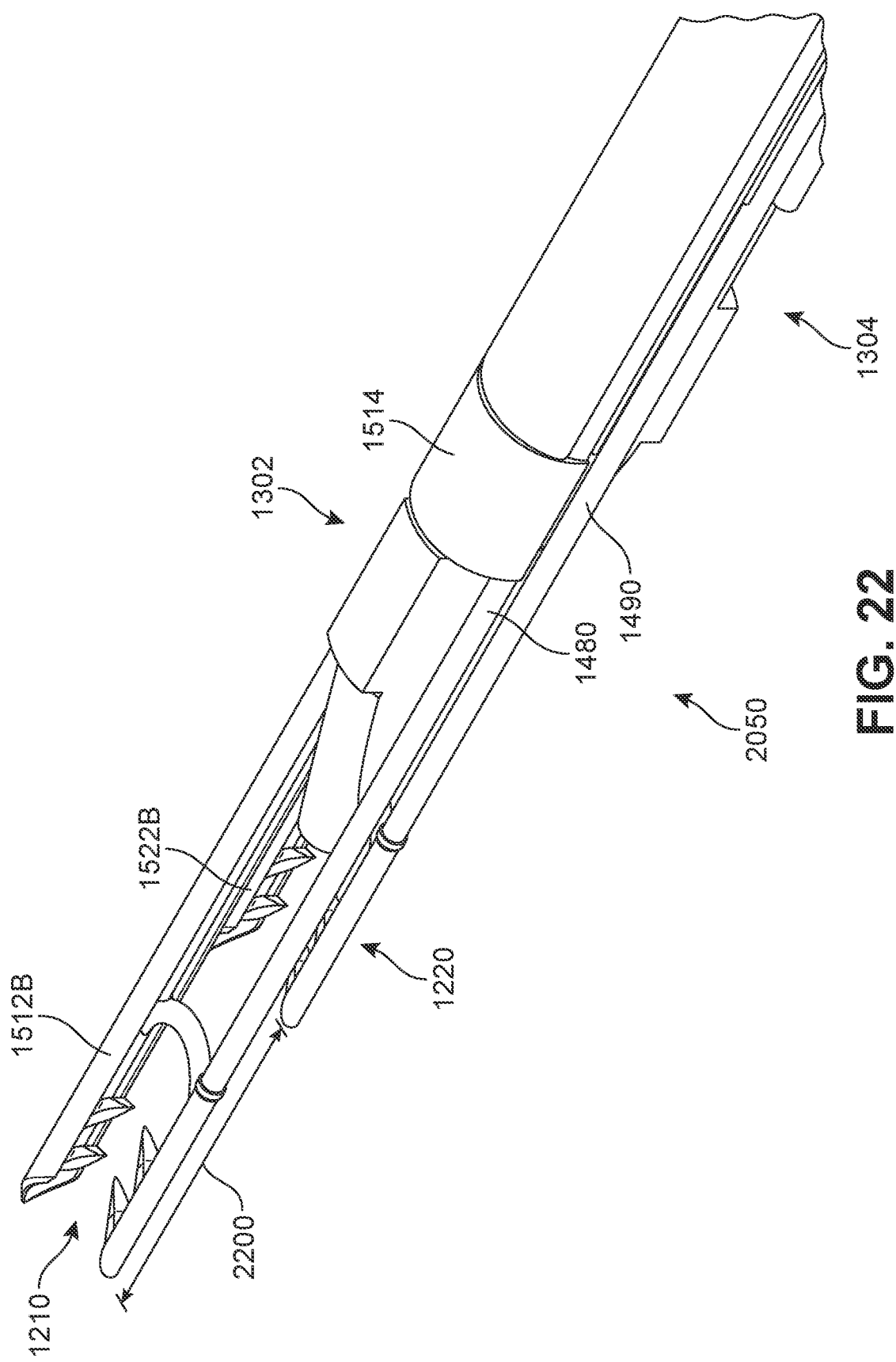
Figure 23:
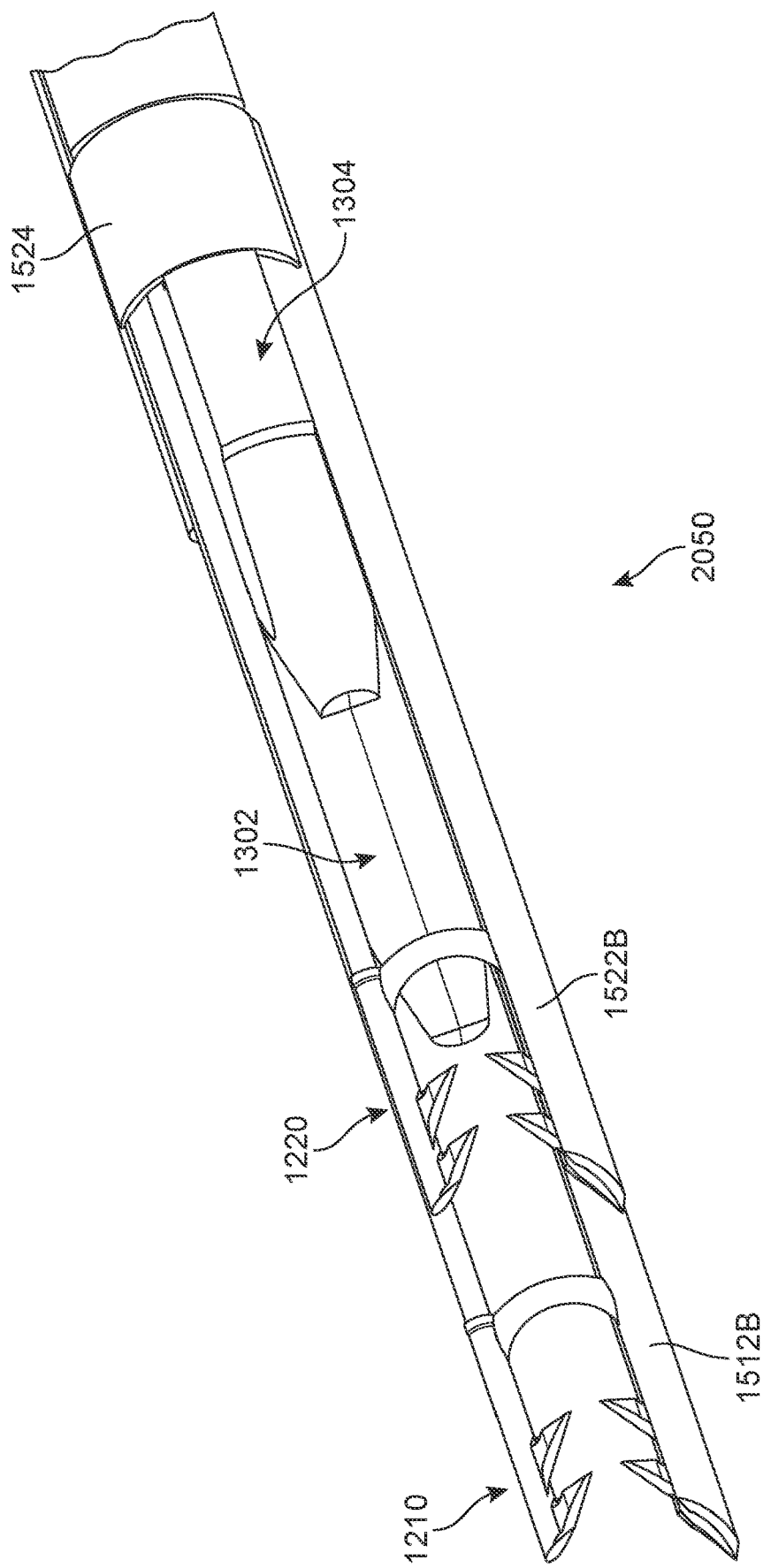

FIGS. 22 and 23 present cutaway perspective views of a portion of the deployment device in the primary actuated configuration 2050 in which the tube housing, tip portion, and two needle members have again been removed to reveal the relative arrangement of the pushing members, anchor engaging rods, and anchors. FIG. 22 depicts an upper perspective view and FIG. 23 depicts a lower perspective view. In FIGS. 22 and 23 it can be observed that the system is no longer symmetrical with respect to the central longitudinal axis. Thus, the nose portion of the first pushing member 1302 is distal relative to the nose portion of the second pushing member 1304. In concert with this move forward, the first anchor engaging rod 1480 and second needle member 1512b, held alongside the first pushing member 1302 by the first retaining clip 1514 (included in this drawing for purposes of clarity), also project outward further relative to the second anchor engaging rod 1490. The movement forward of the first anchor engaging rod 1480 has caused a pushing force to be applied to the first anchor 1210, such that first anchor 1210 now extends further outward by a sixth distance 2200 relative to the second anchor 1220. In one embodiment, fourth distance 2100 and fifth distance 2102 (see FIG. 21) are substantially similar to the sixth distance 2200 shown in FIG. 22.

In use, the deployment device may be used in one of two ways. In some cases, the tip of the deployment device may be held against the implant/graft/tissue and the trigger pulled in order to deploy the needle members and pierce the implant/graft/tissue. In other cases, the needle members may be deployed first, before engaging the implant/graft/tissue, and then the deployment device may be advanced as a whole in order to sink the needle members into the implant/graft/tissue.

Figure 24:
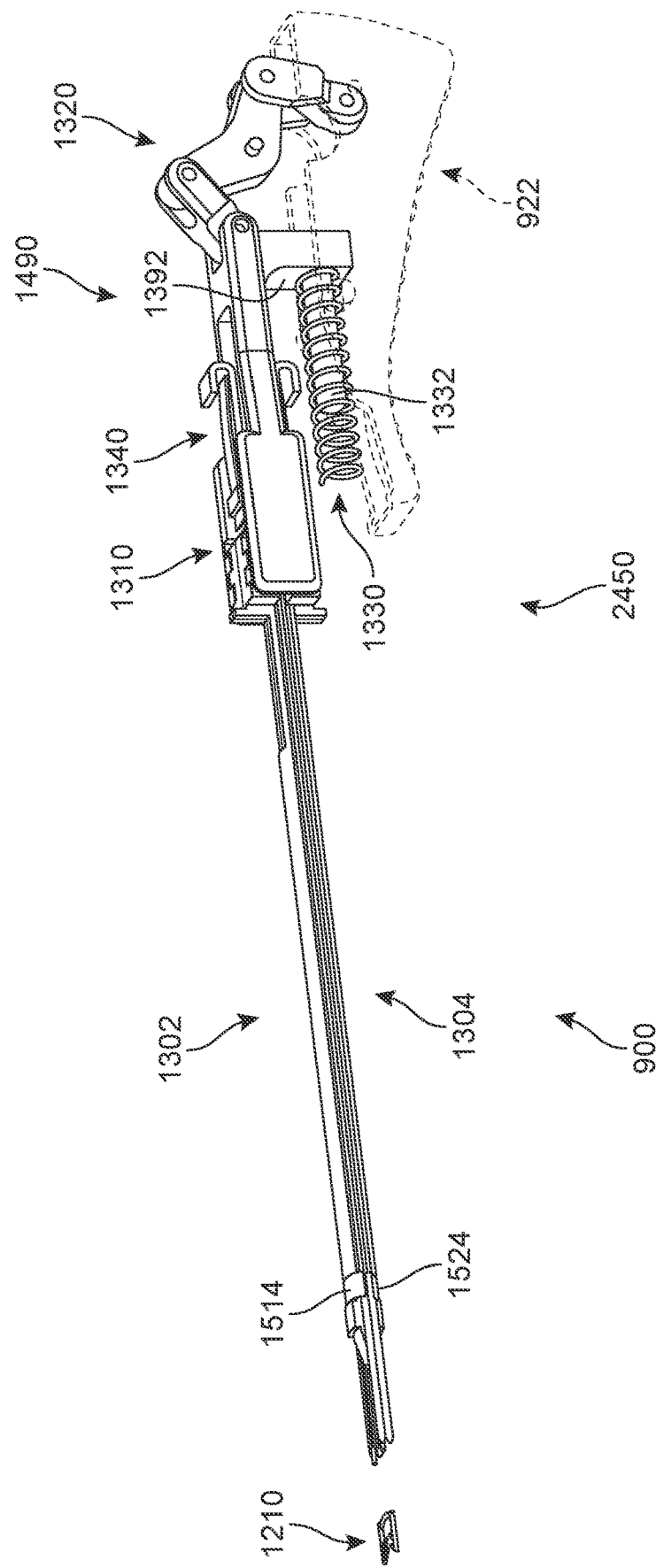
FIGS. 24-26 present schematic views of the deployment device in a deployed configuration whereby a first anchoring device is deployed, according to an embodiment.
Figure 25:
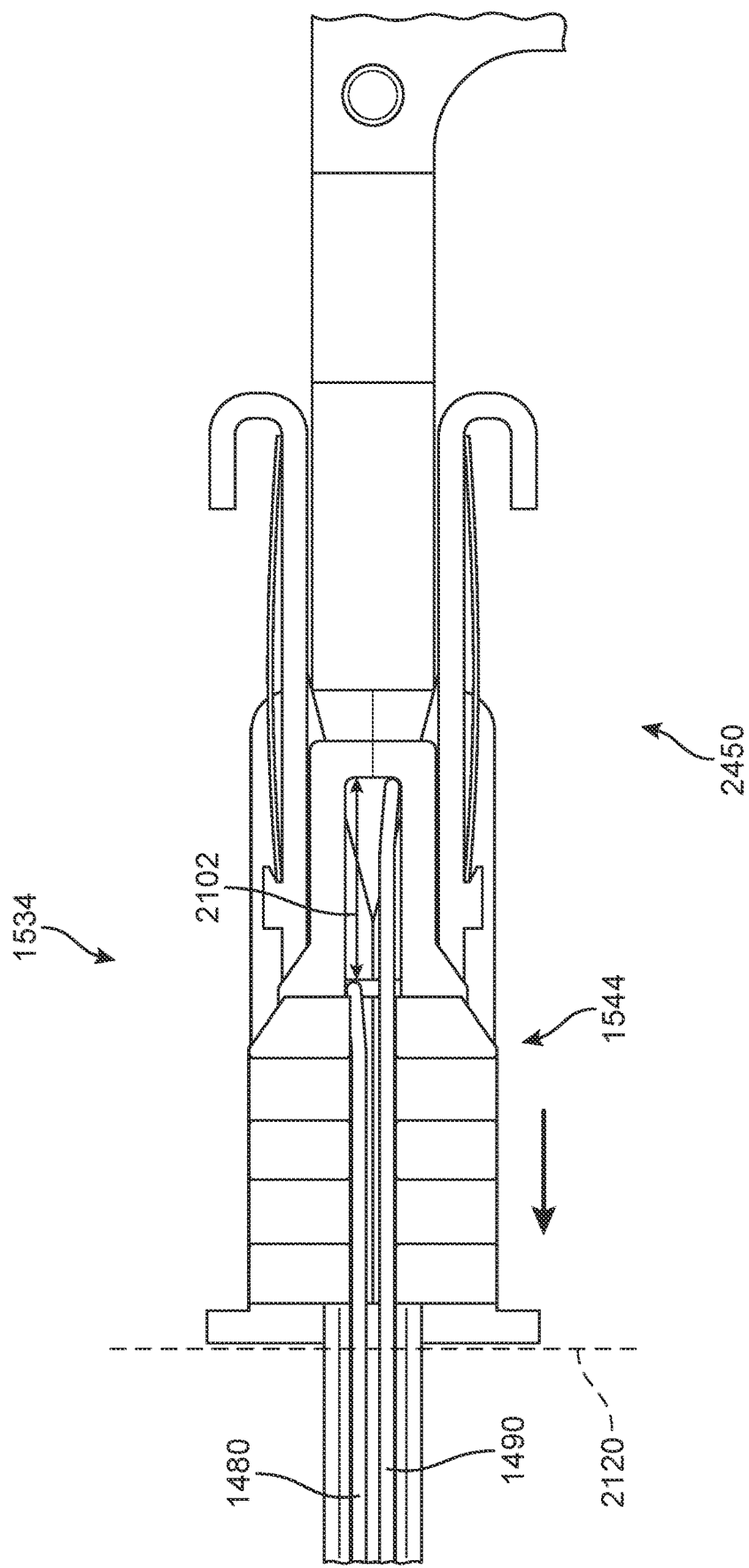
Figure 26:
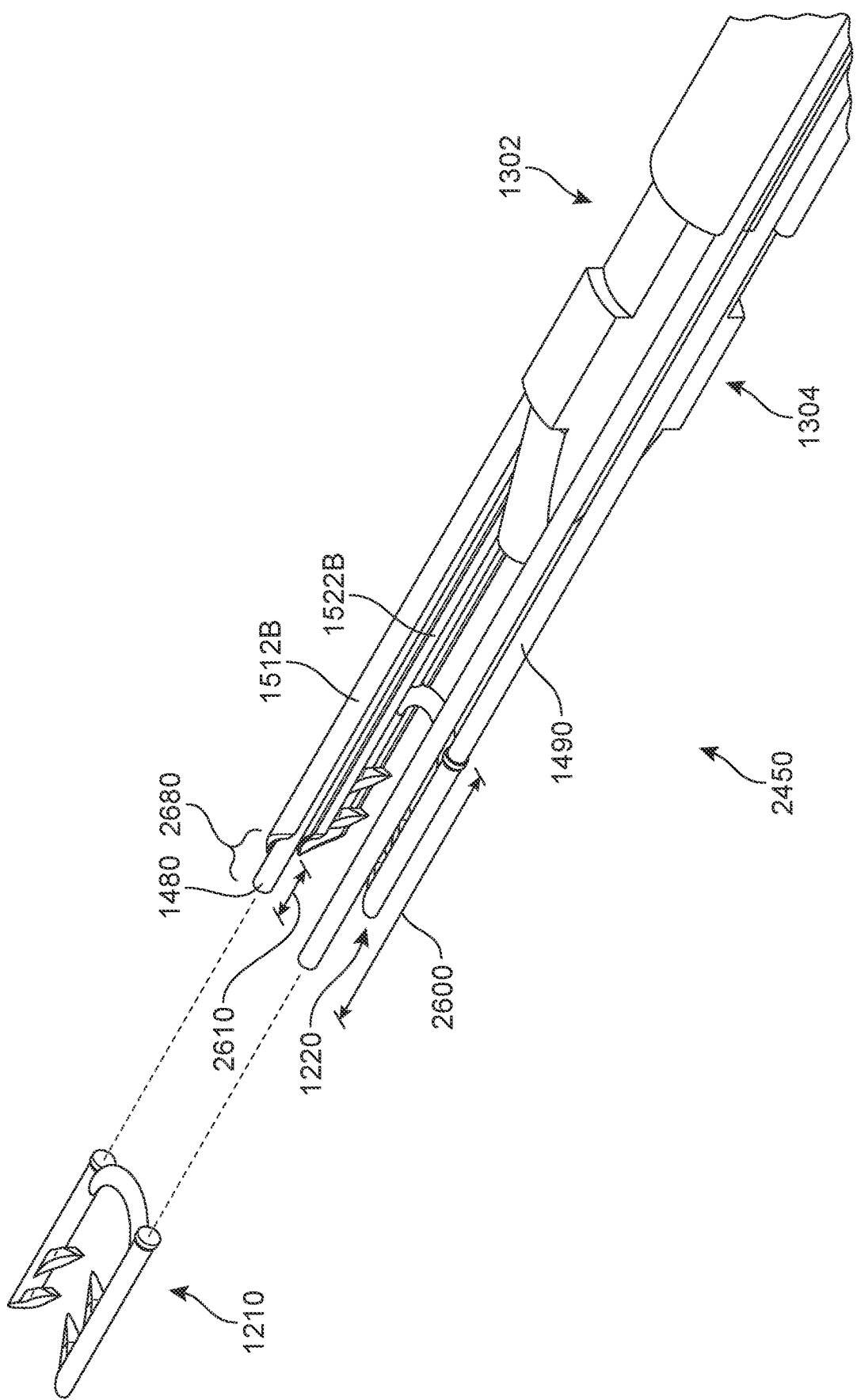

Referring next to FIGS. 24-26, deployment device 900 is shown in an initial deployed configuration 2450, with first pushing member 1302 having slid backward until again aligning with second pushing member 1304. The spring 1330 has returned to an extended configuration around the protruding portion 1332. Furthermore, the linkage assembly 1320 has transitioned back from the extended position to its contracted (neutral) position. In this third stage, the second selector button 1124 continues to be depressed, as described in FIGS. 17A-19 above.

In different embodiments, in order for the transition from the primary actuated configuration 2050 (shown in FIGS. 20-23) to the initial deployed configuration 2450 to occur, the handgrip trigger 922 is rocked in the second rotary direction. In the perspective of FIG. 24, the trigger 922 would be pivoted in a generally clockwise direction. Thus, depression of the distal end of the trigger 922 causes rotation of the trigger 922 such that the distal end moves upward in the second rotary direction while the proximal end moves downward. In this case, once the deployment device operator has positioned the tip portion at the desired location, he or she can rock the trigger 922 in the opposite direction to release the first anchor 1210. Furthermore, once handgrip trigger 922 is released, the spring 1330 biases the trigger 922 to return to the neutral position, which is reflected in the depiction of FIG. 24.

Thus, rocking the trigger 922 in the second rotary direction causes the linkage assembly 1320 to contract, which further causes the slider assembly 1310 to be pulled back in a rearward or proximal direction. As discussed with respect to FIGS. 17B and 17C, the engaging portion of the first pushing member 1302 is locked to the sliding component 1310b. When slider assembly 1310 is pulled proximally rearward, first pushing member 1302 is also carried or moved backward the same distance. In contrast, second pushing member 1304, being locked to the second selector button, continues to retain its original position. Thus, the translational movement of the slider assembly 1310 in a proximal direction pulls the locked first pushing member 1302 until first pushing member 1302 is again aligned with second pushing member 1304. The swift retraction of the first pushing member 1302 retracts the needle members, thus releasing the first anchor 1210 from the deployment device 900, as shown in FIG. 24.

The new relative positioning of the first pushing member 1302 to the second pushing member 1304 is more clearly observable in the cutaway side view of the deployment device in FIG. 25. In this view, the housing and first sliding component are removed to reveal the relative arrangement of the pushing members, anchor engaging rods, and drivers. In FIG. 25, it can be observed that several components of the system are once again substantially symmetrical with respect to the central longitudinal axis. Thus, the first pushing member 1302 is disposed directly above and aligned with the second pushing member 1304, and the first driver 1340a is disposed directly above and aligned with the second driver 1340b. However, while the first pushing member 1302 moves back in a proximal direction, the first driver 1340 applies a force against the hook portion of first anchor engaging rod 1480, ensuring that it remains in its actuated position, disposed forward relative to the second anchor engaging rod 1490 by the fifth distance 2102.

Furthermore, both the first driver 1340a and second driver 1340b retain their positions during this stage and remain aligned relative to one another, even as the slider assembly 1310 has translated backward. In this case, the position of the two drivers relative to the slider assembly 1310 has changed such that both drivers are disposed distally further from the fourth region 1392 of the slider assembly 1310 than in the second stage.

FIG. 26 presents a cutaway perspective view of a portion of the deployment device in the initial deployed configuration 2450 in which the tube housing, tip portion, and two needle members are removed to reveal the relative arrangement of the pushing members, anchor engaging rods, and anchors. In FIG. 26 it can be observed that while the pushing members are symmetrical with respect to the central longitudinal axis, the remaining components are staggered. Thus, the nose portions of the first pushing member 1302 and second pushing member 1304 are aligned with one another, and the second needle member 1512b has also been retracted and returned to its original position and thus is disposed directly above and aligned with the fourth needle member 1522b. However, the first anchor engaging rod 1480 remains distal relative to the second anchor engaging rod 1490 by a seventh distance 2600. In one embodiment, seventh distance 2600 is substantially equal to sixth distance 2200 of FIG. 22. This results in a tip region 2680 of both prongs of the first anchor engaging rod 1480 to protrude outward from their needle members by a fourth distance 2610, while both prongs of the second anchor engaging rod 1490 remain enclosed within their respective needle members. That is, because the first anchor engaging rod 1480 remains extended while first needle member 1512b and the second needle member (not shown in FIG. 26) are retracted, the anchor remains in place (e.g., inserted into the patient's tissue) while the needle members are retracted, thus releasing/deploying the anchor from the deployment device. That is, because the needle members are withdrawn independent of the anchor engaging rod, the anchoring device remains static with respect to the tissue and with respect to the body of the deployment device. Accordingly, the anchoring device remains in place at the implanted location when the deployment device is withdrawn. The removal of the first needle member and third needle member in FIG. 26 also more clearly illustrates the absence of the first anchor 1210 from the tube assembly, and the remaining loaded second anchor 1220.

Figure 27:
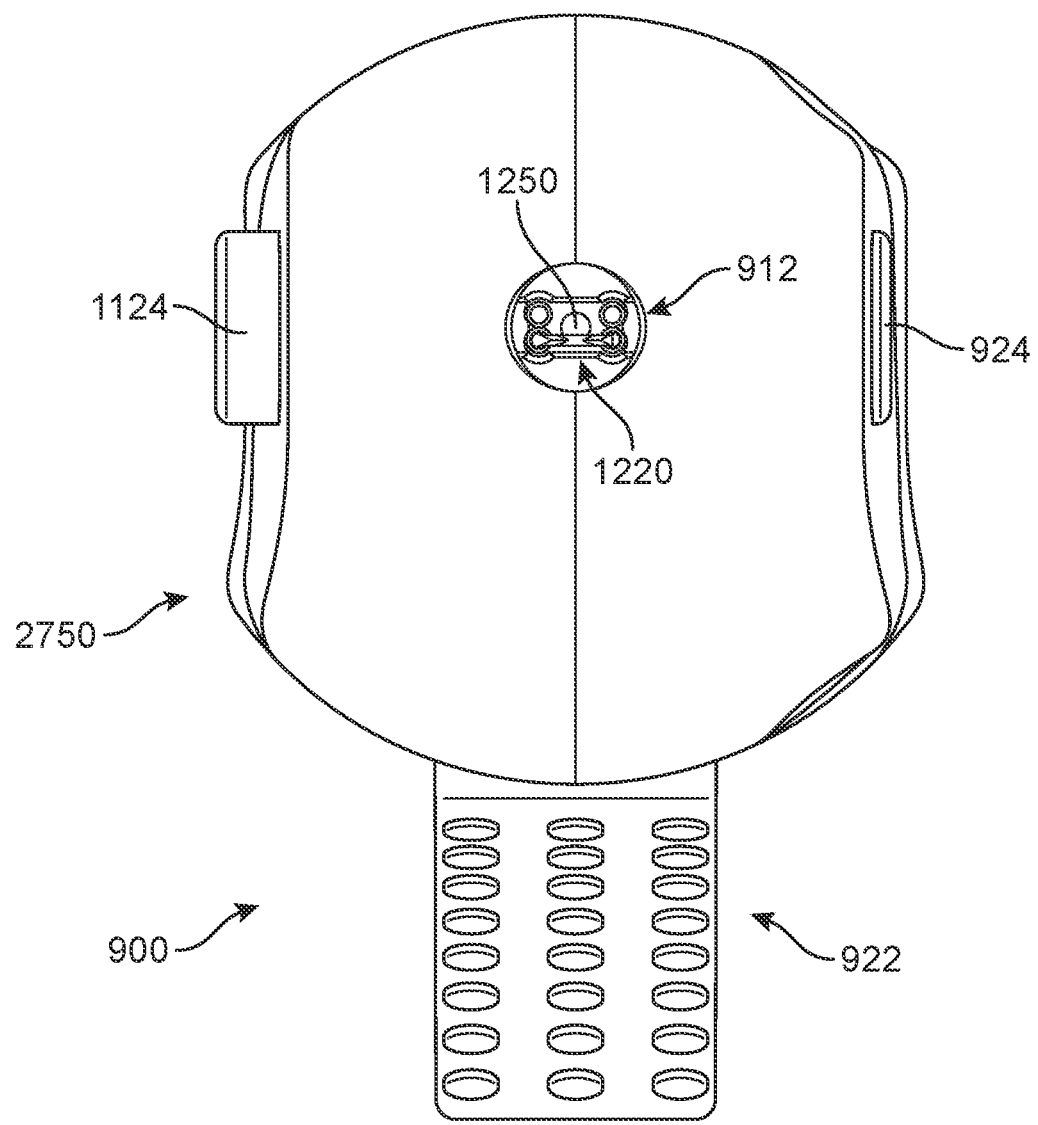
FIGS. 27-29 present schematic views of the deployment device in a locked configuration with a single anchoring device loaded onto the deployment device, according to an embodiment.

Additional context regarding the function of the deployment device is now provided with reference to FIGS. 27-33, which will illustrate the deployment sequence for the second anchor. In FIG. 27, a forward-facing view of deployment device 900 depicts a secondary locked configuration 2750 whereby the first selector button 924 has been depressed and one of the two anchors has been previously deployed. Thus, the dual deployment system now has only a single anchor (second anchor 1220). Second selector button 1124 has returned to its initial or neutral state. In different embodiments, selection of one button can automatically cause the other button to 'pop' back out to the neutral position. In some other embodiments, a press of an already depressed button can return the button to its neutral state. In another example, deployment can automatically return the button to its neutral state.

Figure 28:
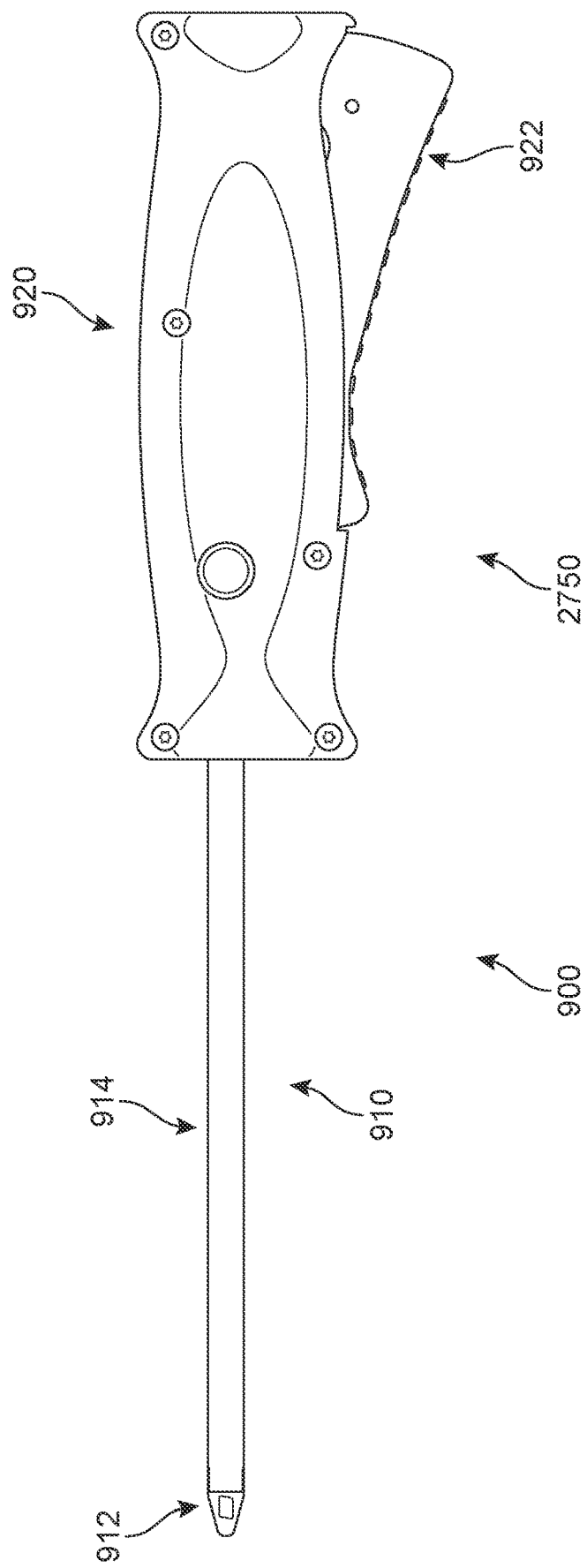

As a general matter, unless otherwise noted, the mechanism for the deployment of second anchor 1220 is similar to that depicted for the first anchor 1210 in FIGS. 17A-26. In the secondary locked configuration 2750, the second anchor 1220, as well as the other components of tube assembly 910, are all interiorly disposed, as shown in the side-view of FIG. 28. FIG. 28 offers an exterior view of the deployment device 900 that includes body housing 926, tube housing 914, and tip portion 912, in order to provide further understanding of the embodiments.

Figure 29:
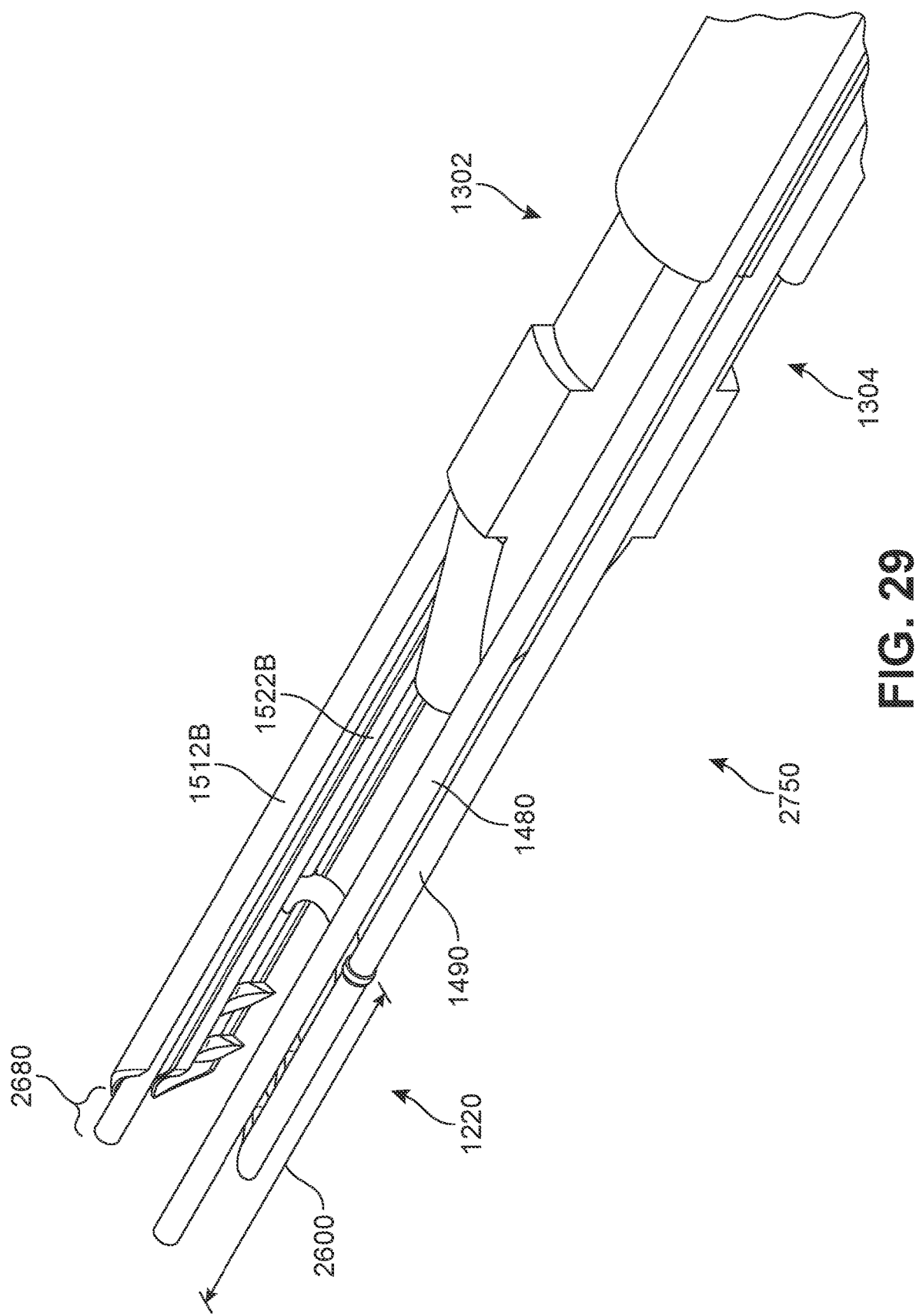

FIG. 29 presents a cutaway perspective view of a portion of the deployment device in the secondary locked configuration 2750 in which the tube housing, tip portion, and two needle members have been removed to reveal the relative arrangement of the pushing members, anchor engaging rods, and anchors. In FIG. 29, it can be observed that the components shown are arranged as they were in the initial deployed configuration 2450 of FIG. 26.

Figure 30:
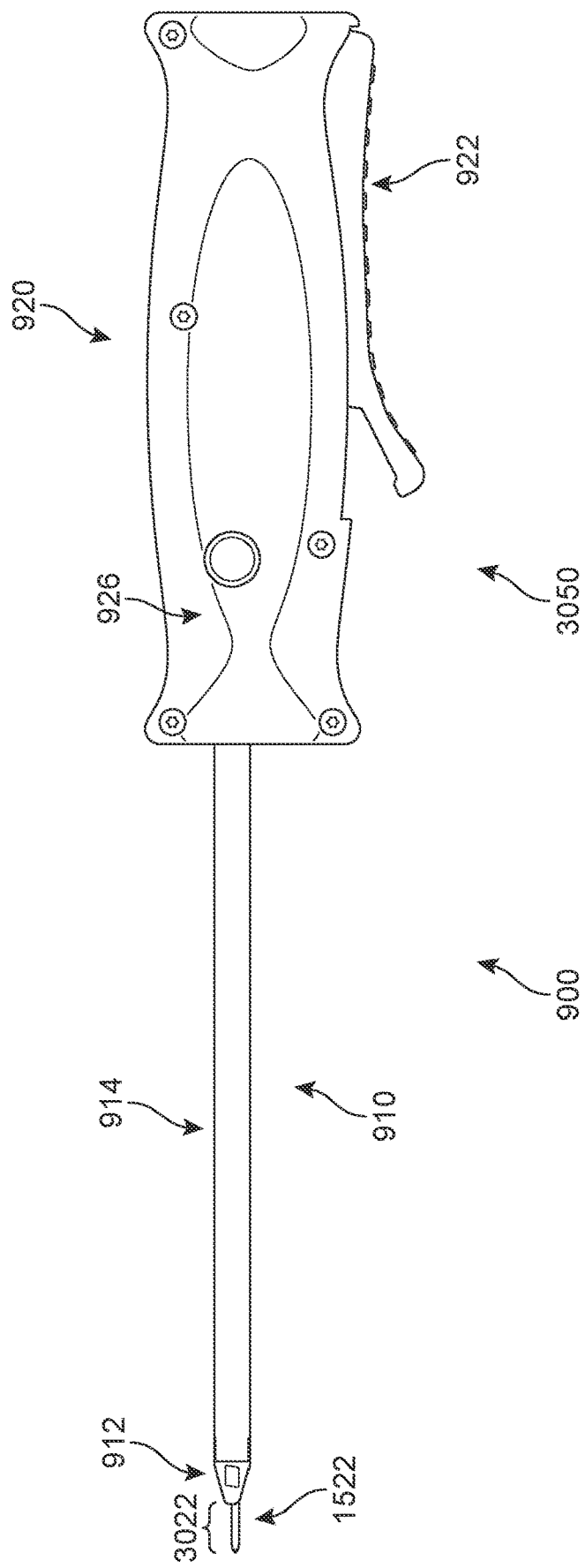
FIGS. 30 and 31 present schematic views of the deployment device in an actuated configuration, according to an embodiment.
Figure 31:
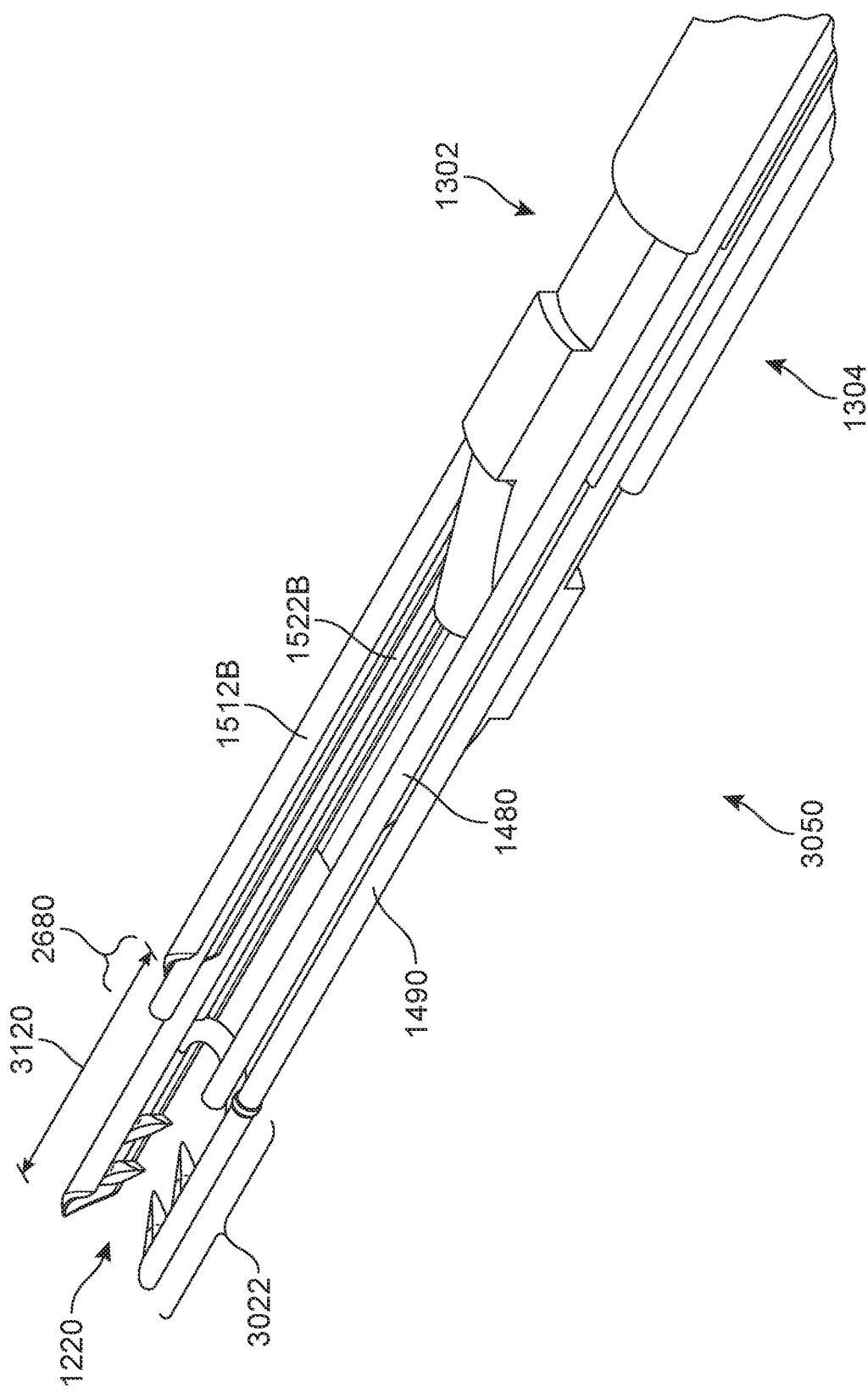

In the subsequent state of FIGS. 30 and 31, a secondary actuated configuration 3050 is presented, whereby the first selector button 924 is depressed, one of the two anchors has been deployed, and the handgrip trigger 922 has been re-actuated. In FIG. 30, a side view of the exterior of deployment device 900 is illustrated, revealing that the secondary actuated configuration 3050 (as well as primary actuated configuration 2050 of FIG. 20) is associated with a protrusion of the third receiving tube 1522a for second pushing member from the tip portion 912. In this view, a projected portion 3022 comprising the second anchor (not shown), third needle member 1522a, and fourth needle member (not shown) is exposed and disposed outside of the tube assembly 910. It can be understood that the complementary fourth receiving tube 1522b, while not visible in FIG. 30, also protrudes distally outward by the same amount.

In FIG. 31, a cutaway perspective view of a portion of the deployment device in the secondary actuated configuration 3050 is shown in which the tube housing, tip portion, and two needle members have been removed to reveal the relative arrangement of the pushing members, anchor engaging rods, and anchors. In FIG. 31, the second pushing member 1304 is now distal relative to the first pushing member 1302. The first anchor engaging rod 1480 and the second anchor engaging rod 1490 are once again aligned, while the fourth receiving tube 1512b has moved in the distal direction by an eighth distance 3120. In one embodiment, eighth distance 3120 is substantially equal to seventh distance 2600. Although not shown in this figure, it should be understood that the third needle member moves in concert with the fourth needle member 1512b.

Thus, second pushing member 1304 has translated in the distal direction until both prongs of the second anchor engaging rod 1490 have pushed the second anchor 1220 outside of tip portion 912. The second anchor 1220, third needle member (not shown), and fourth needle member 1522b, collectively referred to as projected portion 3022, are outside of the tube housing. It can be appreciated that, while disposed outside of the tube housing, second anchor 1220 remains stowed in the third and fourth needle members.

Figure 32:
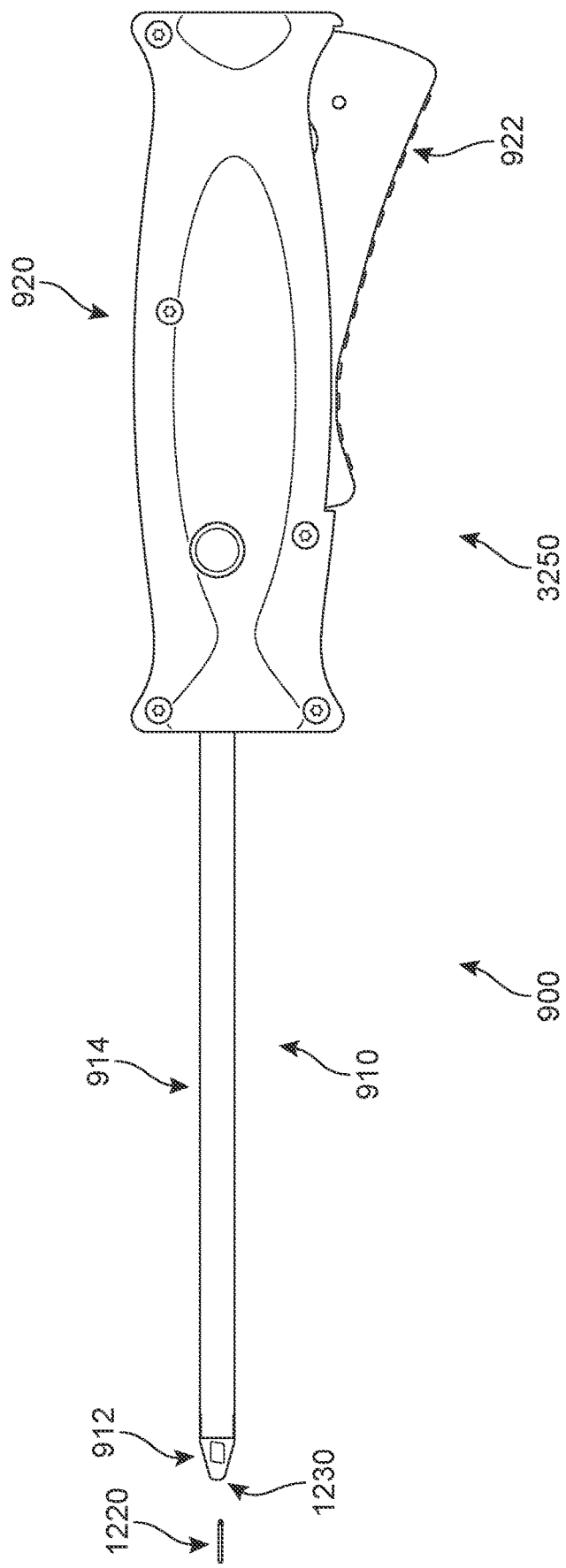
FIGS. 32 and 33 present schematic views of the deployment device in a deployed configuration whereby a second anchoring device is deployed, according to an embodiment.
Figure 33:
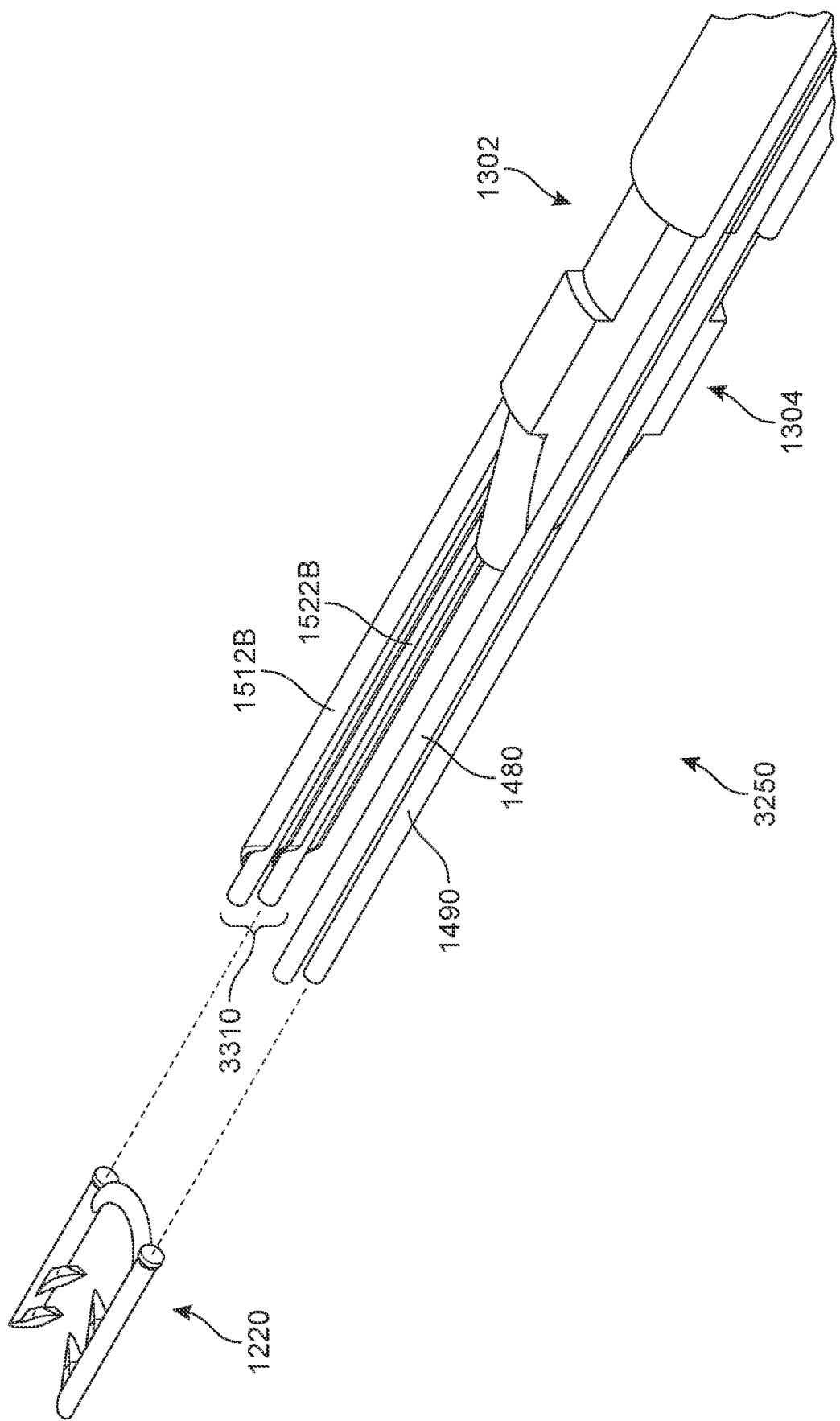

Referring to FIGS. 32 and 33, once the force on trigger 922 is released, as discussed earlier, the spring acts to bias the trigger back to the neutral position and also pulls the second pushing member back so that the needle members are fully retracted within tip portion 912. FIG. 33 depicts a cutaway perspective view that shows the distal ends 3310 of both anchor engaging rods protruding out from the ends of the receiving tubes by the same amount. Thus, both anchor engaging rods are now in the same state as the first anchor engaging rod 1480 was during both the initial deployed configuration 2450 of FIG. 26 and the secondary locked configuration 2750 of FIG. 29. Furthermore, in contrast to the initial primary locked configuration of FIG. 19, the anchor engaging rods are now the most distal component of the interior components comprising tube assembly 910.

Figure 34:
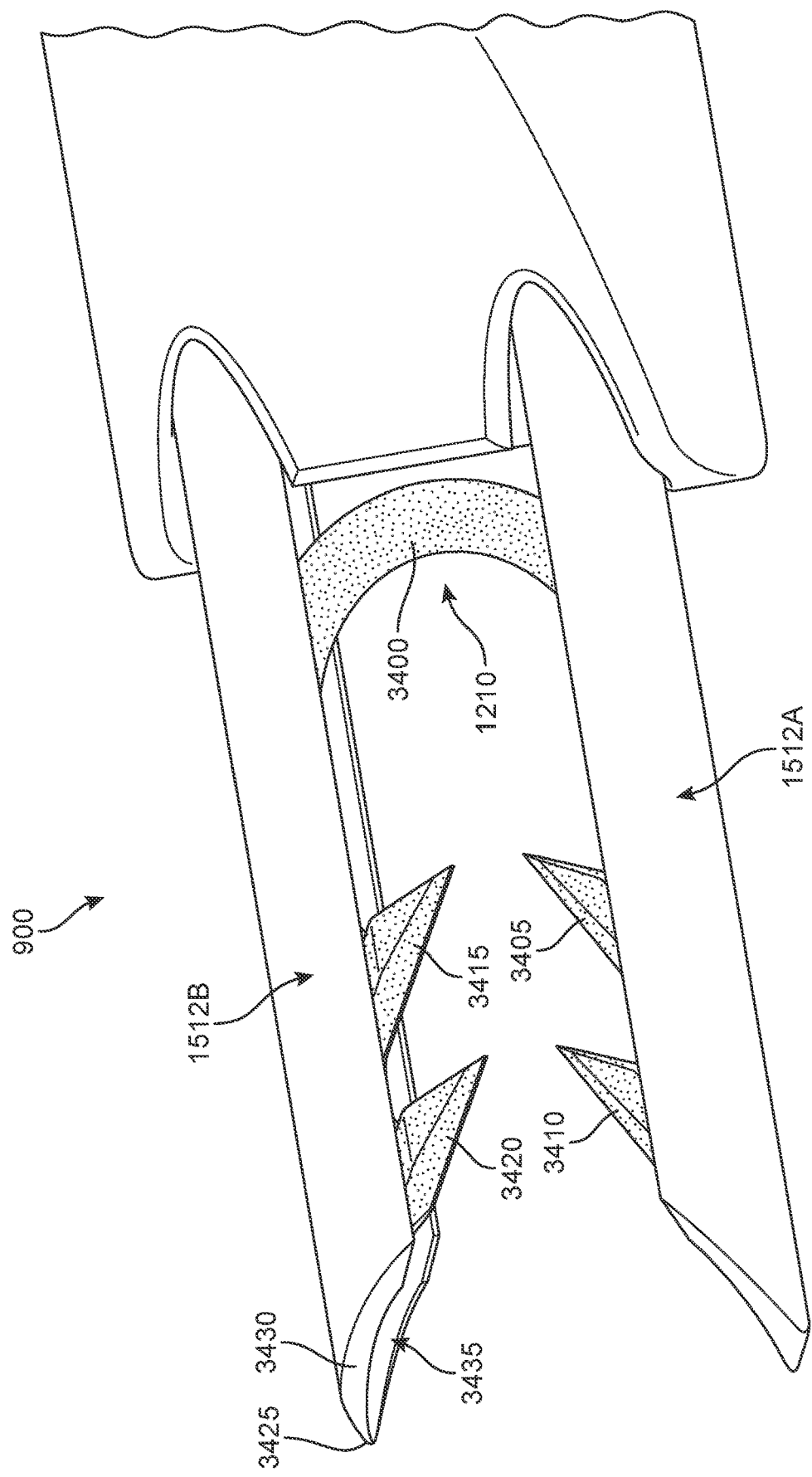
FIGS. 34 and 35 are schematic, perspective illustrations of needle members with an anchoring device disposed therein in a configuration in which the two elements are driven into tissue/graft material.
Figure 35:
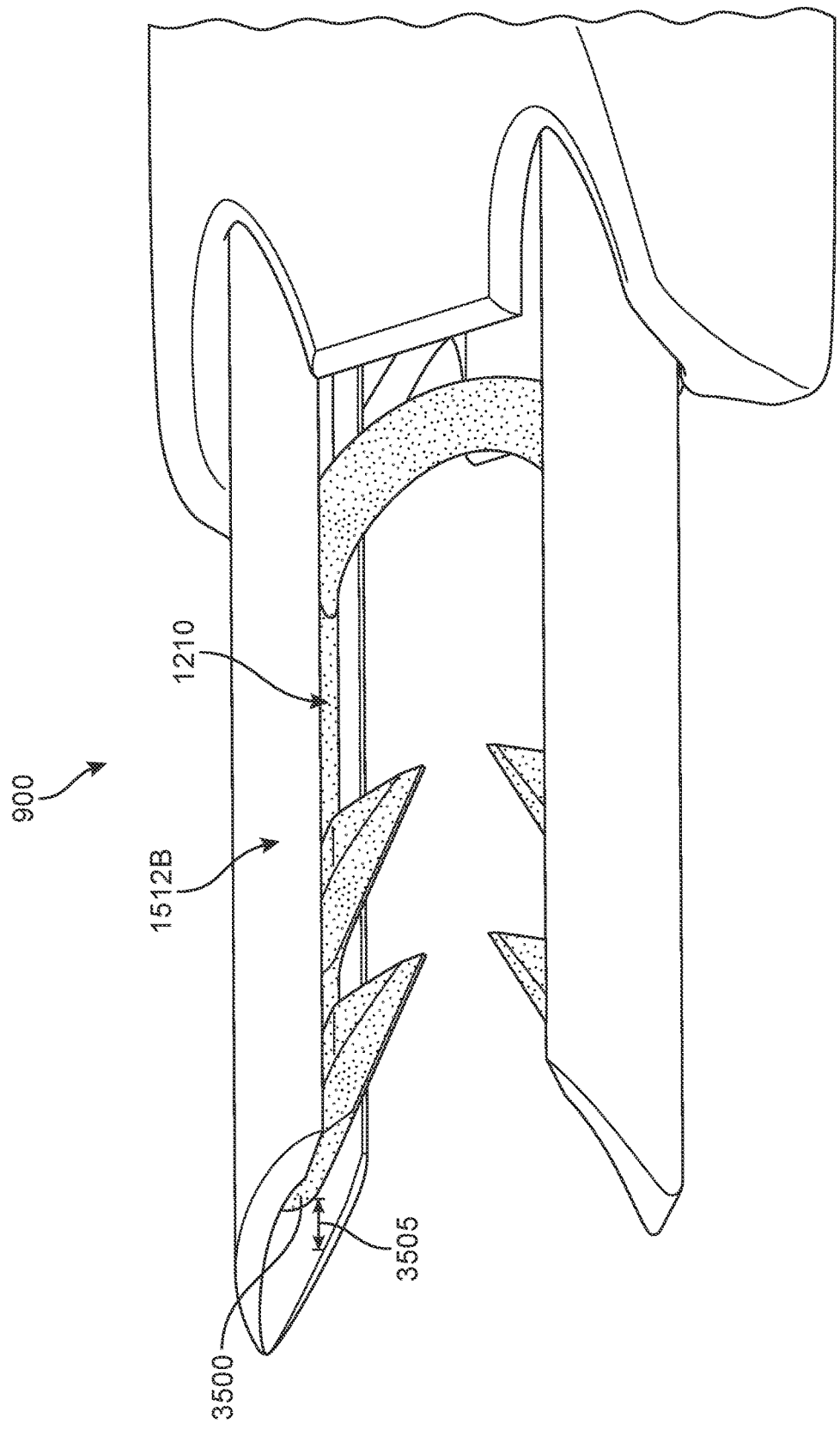

FIGS. 34 and 35 are schematic, perspective illustrations of needle members with an anchoring device disposed therein in a configuration in which the two elements are driven into tissue/graft material. FIG. 32 illustrates anchoring device 1210 disposed within first needle member 1512A and second needle member 1512B. As further shown in FIG. 34, the connecting member 3400 of anchoring device 1210 extends between first needle member 1512A and second needle member 1512B. Also extending from the slots in the needle members are the barbs of anchoring device 1210. As shown in FIG. 34, a first barb 3405 and a second barb 3410 extend out of the slot in first needle member 1512A and a third barb 3415 and a fourth barb 3420 extend out of the slot in second needle member 1512B.

In some embodiments, the needle members may have Greene tip needle grinds, e.g., with an outer bevel and a curved edge. For example, as shown in FIG. 34, second needle member 1512B includes a distal tip 3425 and an outer bevel 3430 on the outward edge. In addition, as further shown in FIG. 34, the distal end of second needle member 1512B may include a curved edge 3435. This curved edge 3435 generally corresponds to the scalloped portion 397 of the anchor device shown in FIG. 3.

In addition, when in the piercing condition, the anchoring device may be recessed from the distal tips of the needle members. For example, as shown in FIG. 35, the beveled distal surface 3500 of anchoring device 1210 is recessed from the distal end of second needle member 1512B by a distance 3505. This prevents the graft/tissue from compressing when the combination of the needle member and anchoring device pierces the graft/tissue.

It will be understood that the configuration of the second needle member 1512B and anchoring device 1210 shown in FIGS. 34 and 35 and discussed above may also apply to first needle member 1512A and anchoring device 1210. Further, such configurations may also apply to third needle member 1522A, fourth needle member 1522B, and anchoring device 1220 shown in FIG. 16. It will be further understood that, in some embodiments, the configuration between one anchoring device and the corresponding needle members may be different than the configuration between a second anchoring device and its, respectively corresponding needle members.

Although the embodiments describe an anchoring system that is used to secure tissue grafts to other tissue in the body, it may be appreciated that this system could also be used with synthetic structures. For example, the anchoring system could be used to attach synthetic materials to other tissues in a body.

While various embodiments are described, the description is intended to be exemplary, rather than limiting and it will be apparent to those of ordinary skill in the art that many more embodiments and implementations are possible that are within the scope of the disclosed embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted. Further, unless otherwise specified, any step in a method or function of a system may take place in any relative order in relation to any other step described herein.

What is claimed is:

1. A surgical anchoring device, comprising:
a first beam and a second beam each extending along a longitudinal direction; and
a connecting member bridging a first proximal portion of the first beam to a second proximal portion of the second beam such that the first beam is substantially aligned with the second beam;
a first barb protruding from a medial side of the first beam, wherein the first barb has a length extending diagonally in a generally proximal direction from the first beam to a tip of the first barb; and
a second barb protruding from a medial side of the second beam, wherein the second barb extends diagonally in a generally proximal direction;
wherein the first barb includes a proximal facing surface that is completely separated from the first beam by a recess;
wherein the first barb intersects with the first beam in a location that is further distal than the distal-most portion of the proximal facing surface of the first barb; and
wherein the proximal facing surface of the first barb extends a majority of the length of the first barb.

2. The anchoring device of claim 1, further including a reinforcing rib disposed within the recess.

3. The anchoring device of claim 1, wherein the connecting member extends further proximally than the proximal ends of the beams.

4. The anchoring device of claim 1, wherein the first beam, second beam, connecting member, first barb, and second barb comprise a monolithic structure formed of a single unitary piece of material.

5. The anchoring device of claim 1, wherein the first beam extends between a proximal end and a distal end, the proximal end terminating in a first surface having a first shape and the distal end terminating in a second surface having a substantially different shape.

6. The anchoring device of claim 5, wherein the proximal end terminates in a substantially circular surface and the distal end terminates in a substantially teardrop-shaped surface.

7. The anchoring device of claim 6, wherein the proximal end terminates in a surface aligned with a lateral axis and the distal end terminates in a surface oriented at an oblique angle relative to the lateral axis.

8. The anchoring device of claim 7, wherein the first barb is contiguous with the distal end of the first beam.

9. A surgical anchoring device, comprising:
a first beam and a second beam each extending along a longitudinal direction; and
a connecting member bridging a first proximal portion of the first beam to a second proximal portion of the second beam such that the first beam is substantially aligned with the second beam;
a first barb protruding from a medial side of the first beam, wherein the first barb has a length extending diagonally in a generally proximal direction; and
a second barb protruding from a medial side of the second beam, wherein the second barb extends diagonally in a generally proximal direction;
wherein the first barb includes a proximal facing surface that is separated from the first beam by a recess;
the surgical anchoring device further including a reinforcing rib disposed within the recess;
wherein the first barb intersects with the first beam in a location that is further distal than the distal-most portion of the proximal facing surface of the first barb; and
wherein the proximal facing surface of the first barb extends a majority of the length of the first barb.

10. The anchoring device of claim 9, wherein the connecting member extends further proximally than the proximal ends of the beams.

11. The anchoring device of claim 9, wherein the first beam, second beam, connecting member, first barb, and second barb comprise a monolithic structure formed of a single unitary piece of material.

12. The anchoring device of claim 9, wherein the first beam extends between a proximal end and a distal end, the proximal end terminating in a first surface having a first shape and the distal end terminating in a second surface having a substantially different shape.

13. The anchoring device of claim 12, wherein the proximal end terminates in a substantially circular surface and the distal end terminates in a substantially teardrop-shaped surface.

14. The anchoring device of claim 13, wherein the proximal end terminates in a surface aligned with a lateral axis and the distal end terminates in a surface oriented at an oblique angle relative to the lateral axis.

15. The anchoring device of claim 14, wherein the first barb is contiguous with the distal end of the first beam.

16. A surgical anchoring device, comprising:
a first beam and a second beam each having a longitudinal length extending along a longitudinal direction from a proximal end of the device to a distal end of the device; and
a connecting member proximate the proximal end of the device and bridging a first proximal portion of the first beam to a second proximal portion of the second beam such that the first beam is substantially aligned with the second beam;
a first barb protruding from a medial side of the first beam, wherein the first barb has a length extending diagonally in a generally proximal direction; and a second barb protruding from a medial side of the second beam, wherein the second barb extends diagonally in a generally proximal direction;

wherein the first barb includes a proximal facing surface that is separated from the first beam by a recess;

wherein the first beam and the second beam have a substantially constant cross-sectional size over a majority of the longitudinal length of each respective beam;

wherein the first barb intersects with the first beam in a location that is further distal than the distal-most portion of the proximal facing surface of the first barb; and wherein the proximal facing surface of the first barb extends a majority of the length of the first barb.

17. The anchoring device of claim 16, wherein each beam has a proximal region, an intermediate region, and a distal region; and wherein the connecting member is attached to the first beam and the second beam in the proximal region of each beam.

18. The anchoring device of claim 16, wherein the connecting member extends further proximally than the proximal ends of the beams.

19. The anchoring device of claim 16, wherein the first beam extends between a proximal end and a distal end, the proximal end terminating in a first surface having a first shape and the distal end terminating in a second surface having a substantially different shape.

20. The anchoring device of claim 19, wherein the proximal end terminates in a substantially circular surface and the distal end terminates in a substantially teardrop-shaped surface.

* * * * *